(12) United States Patent
Min et al.

(10) Patent No.: US 12,062,422 B2
(45) Date of Patent: Aug. 13, 2024

(54) SYSTEM, METHOD AND COMPUTER-ACCESSIBLE MEDIUM FOR USE OF HEAVY WATER AS A PROBE FOR IMAGING METABOLIC ACTIVITIES

(71) Applicant: The Trustees of Columbia University in the City of New York, New York, NY (US)

(72) Inventors: Wei Min, Fort Lee, NJ (US); Lingyan Shi, Brooklyn, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 682 days.

(21) Appl. No.: 17/159,591

(22) Filed: Jan. 27, 2021

(65) Prior Publication Data
US 2021/0151157 A1    May 20, 2021

Related U.S. Application Data

(63) Continuation of application No. PCT/US2019/043935, filed on Jul. 29, 2019.
(Continued)

(51) Int. Cl.
*G16H 20/10* (2018.01)
*A61K 49/00* (2006.01)
(Continued)

(52) U.S. Cl.
CPC ......... *G16H 20/10* (2018.01); *A61K 49/0002* (2013.01); *A61K 49/0004* (2013.01);
(Continued)

(58) Field of Classification Search
CPC ............... G16H 20/10; A61K 49/0002; A61K 49/0004; A61K 49/00; G01N 21/65;
(Continued)

(56) References Cited

U.S. PATENT DOCUMENTS

2010/0020319 A1 * 1/2010 Demos ................. A61B 5/0075
356/301
2016/0243261 A1 * 8/2016 Min ..................... A61K 49/0013

FOREIGN PATENT DOCUMENTS

WO    WO-2013173446 A1 * 11/2013 ............. G01N 15/14

OTHER PUBLICATIONS

Pirali et al., Applications of Deuterium in Medicinal Chemistry, Journal of Medicinal Chemistry, Jan. 14, 2019 62 (11), 5276-5297, DOI: 10.1021/acs.jmedchem.8b01808 (Year: 2019).*
(Continued)

*Primary Examiner* — Joy Chng
(74) *Attorney, Agent, or Firm* — Amster, Rothstein & Ebenstein LLP

(57) ABSTRACT

Incorporation of deuterium into the lipids, proteins, and/or genetic material in cells, tissues, organs, or organisms, including animals, such as humans, and plants, by administration of heavy water, allows for the spectral determination of levels of lipids, proteins, and/or genetic material using Raman spectroscopy, such as stimulated Raman spectroscopy. Following administration of a drug, changes in the relative amounts of lipid, protein, and/or genetic materials can be determined, and the efficacy, or lack thereof, of the administered drug can be determined.

10 Claims, 48 Drawing Sheets

Related U.S. Application Data

(60) Provisional application No. 62/711,197, filed on Jul. 27, 2018, provisional application No. 62/819,192, filed on Mar. 15, 2019.

(51) Int. Cl.
*G01N 21/65* (2006.01)
*G01N 33/68* (2006.01)

(52) U.S. Cl.
CPC ......... *G01N 21/65* (2013.01); *G01N 33/6848* (2013.01); *G01N 2021/656* (2013.01); *G01N 2458/15* (2013.01); *G01N 2500/10* (2013.01); *G01N 2570/00* (2013.01)

(58) Field of Classification Search
CPC ......... G01N 33/6848; G01N 2021/656; G01N 2458/15; G01N 2500/10; G01N 2570/00; G01N 33/483; Y02A 90/10
USPC ....................................................... 705/2–3
See application file for complete search history.

(56) References Cited

OTHER PUBLICATIONS

International Search Report and Written Opinion for International Patent Application No. PCT/US2019/043935 mailed on Nov. 22, 2019.

* cited by examiner

EXHIBIT B

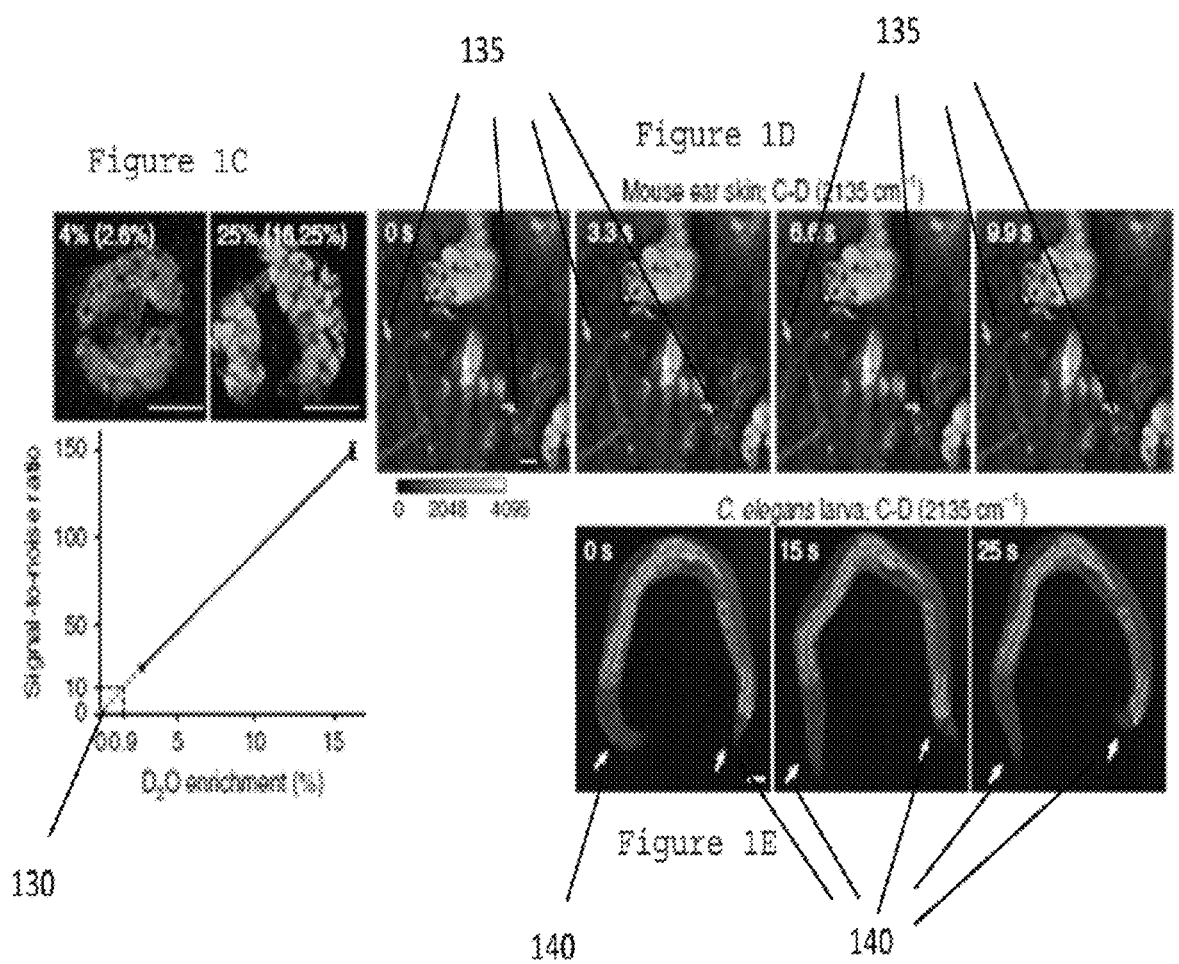

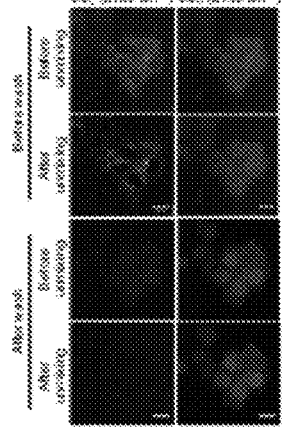
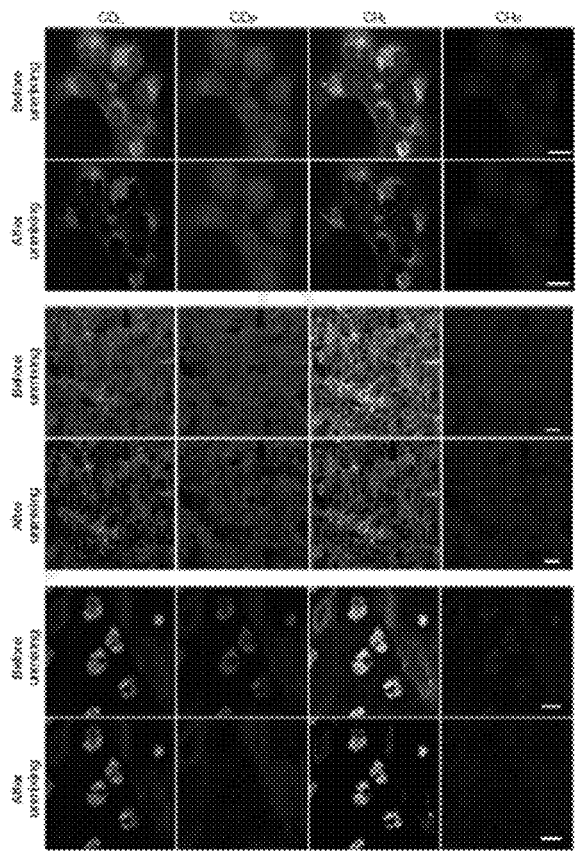
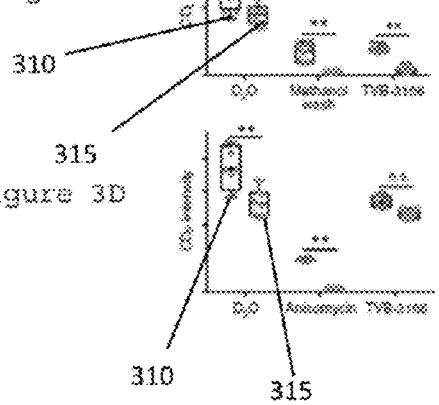
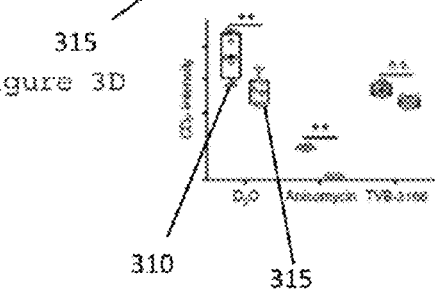
Figure 3F
Figure 3G

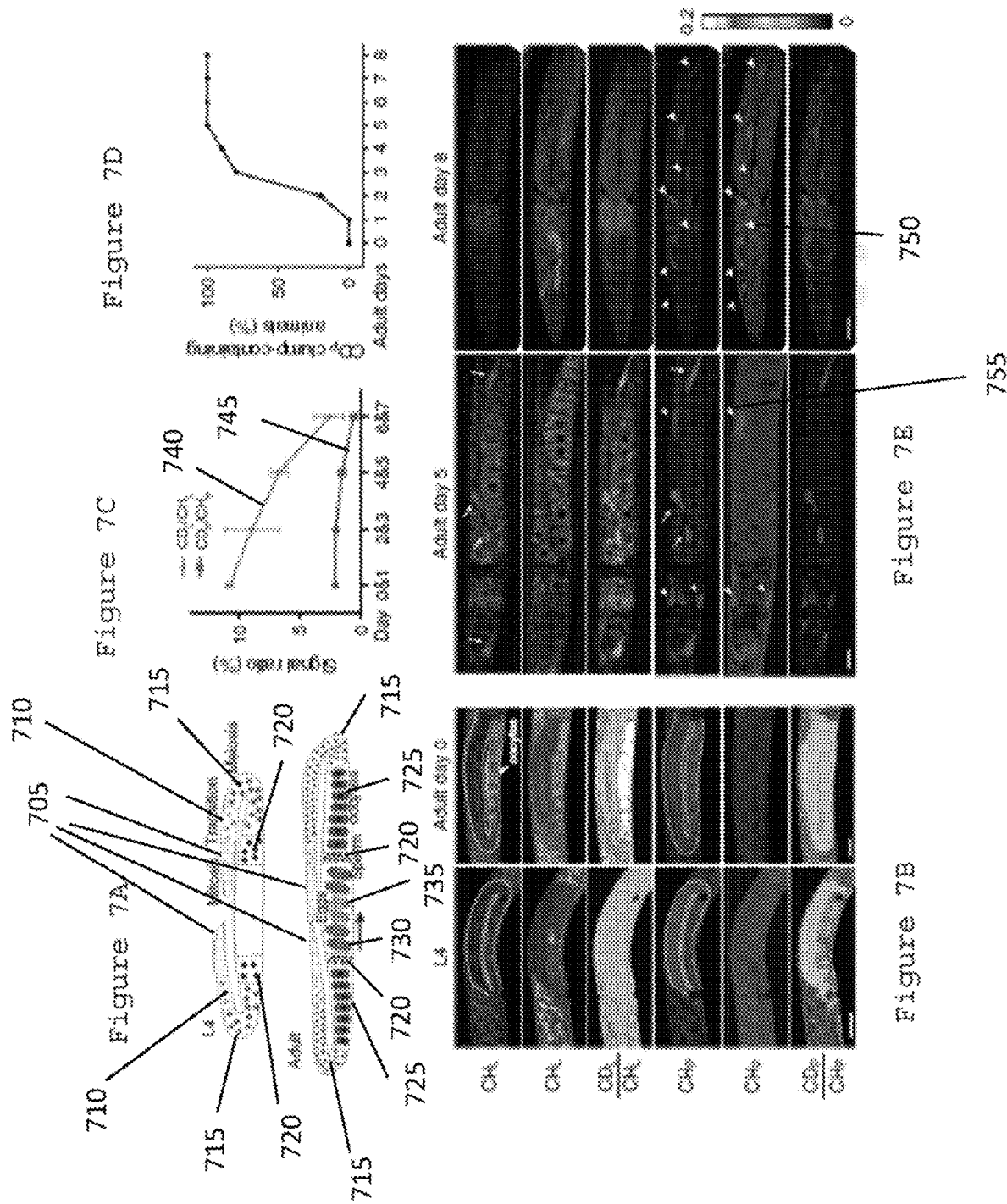

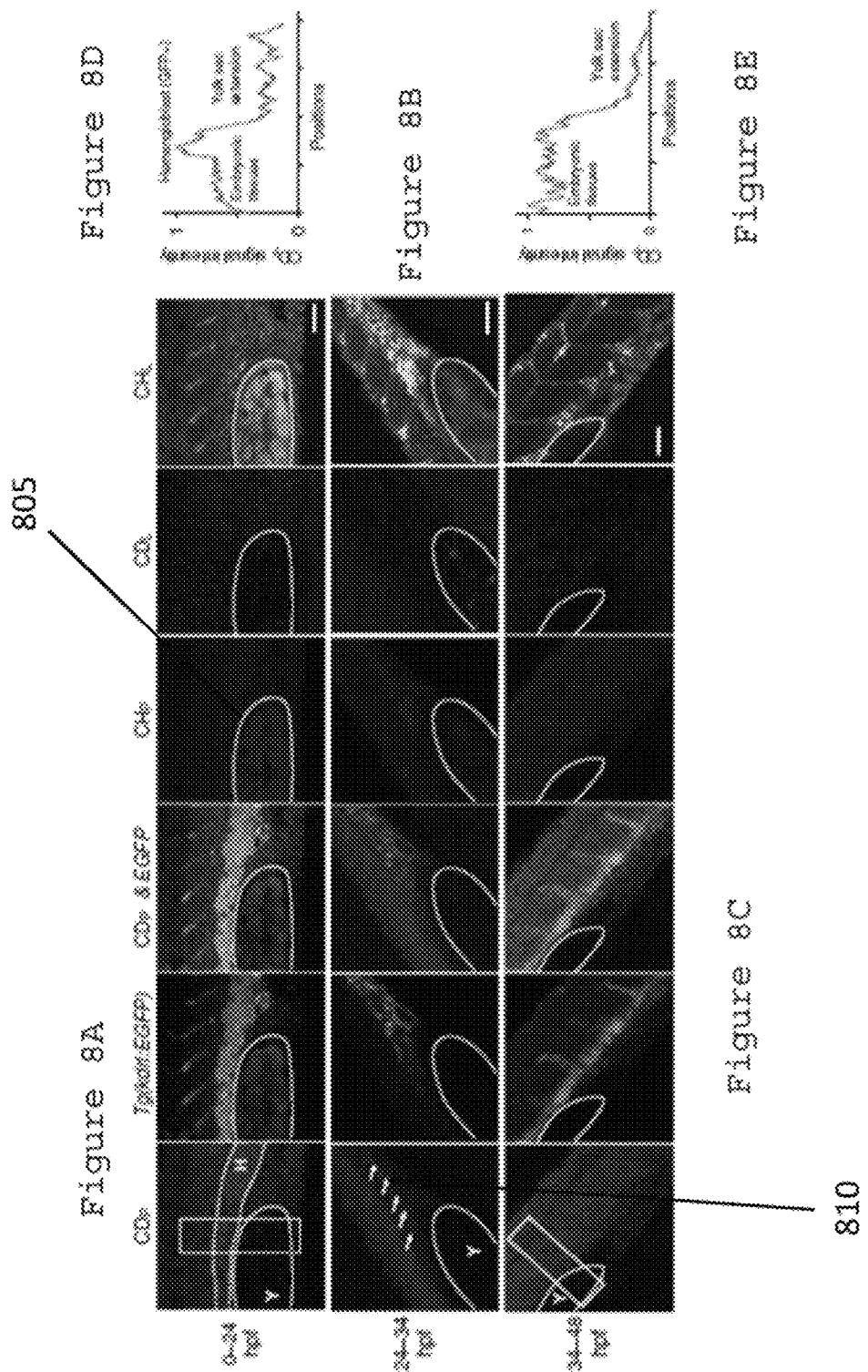

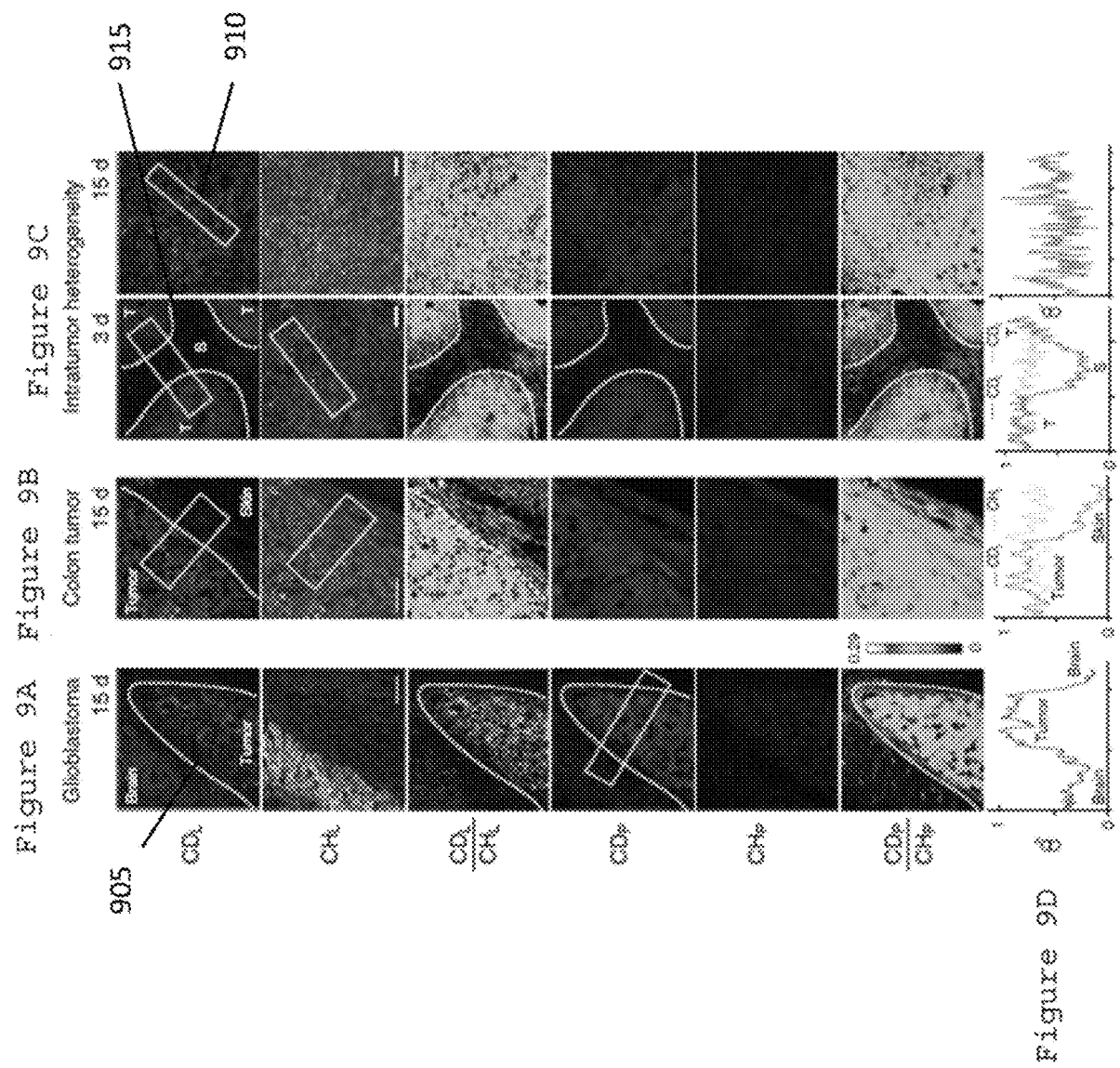

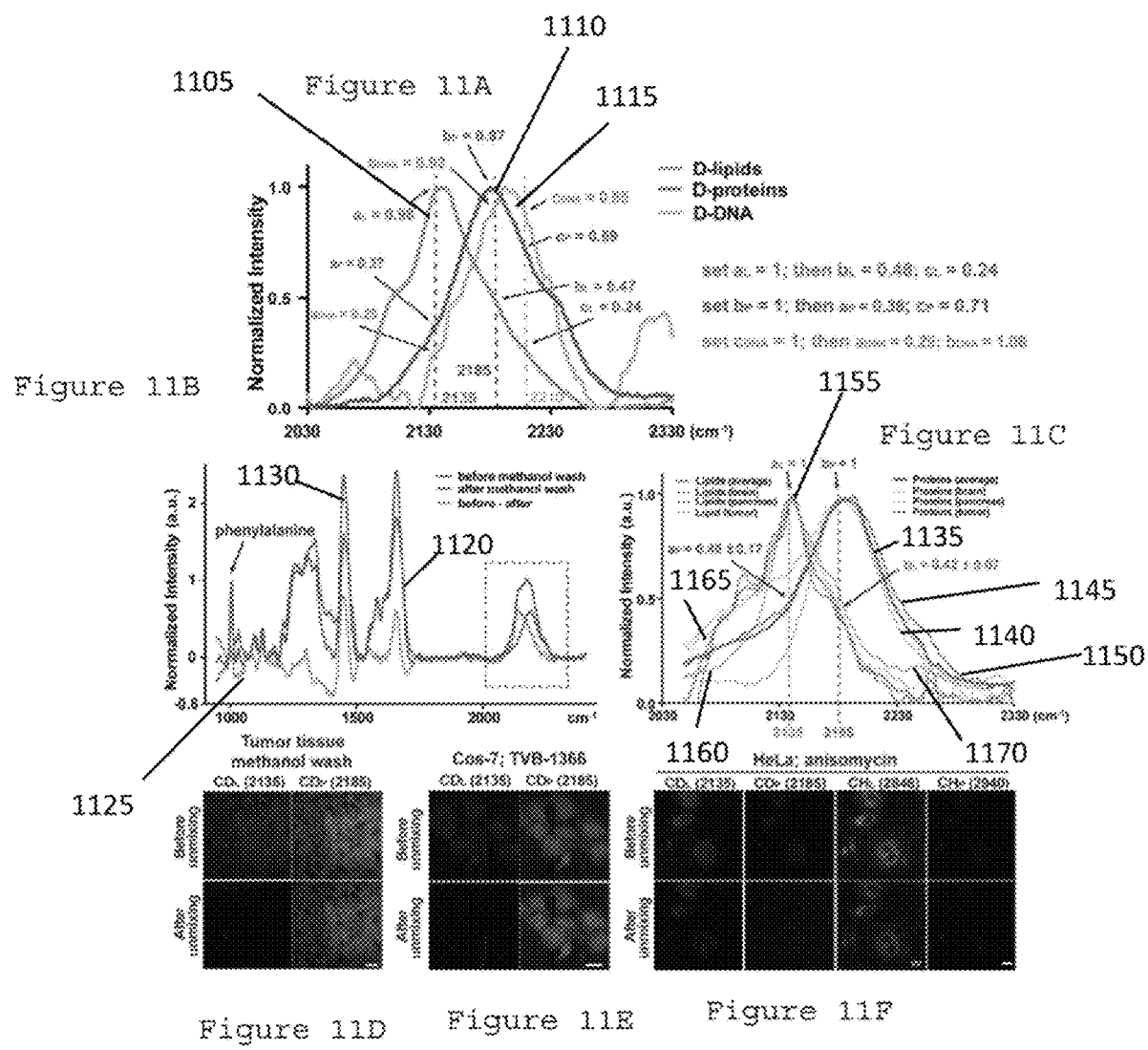

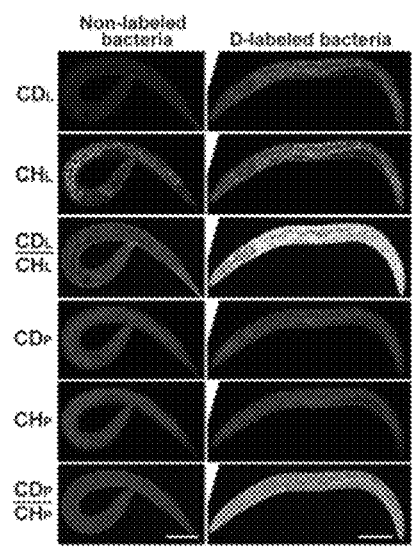
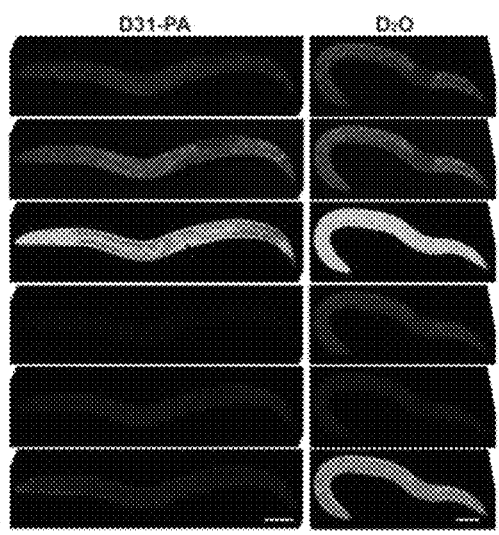
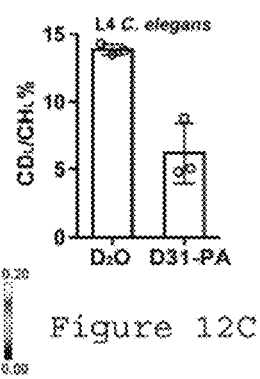
Figure 12A
Figure 12B
Figure 12C

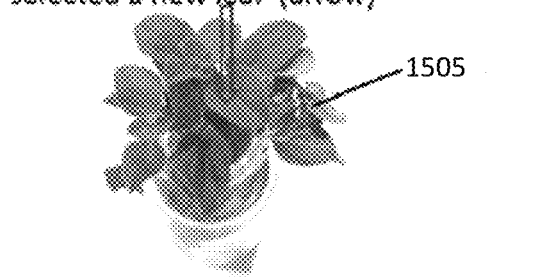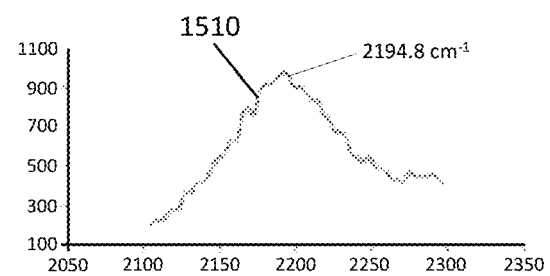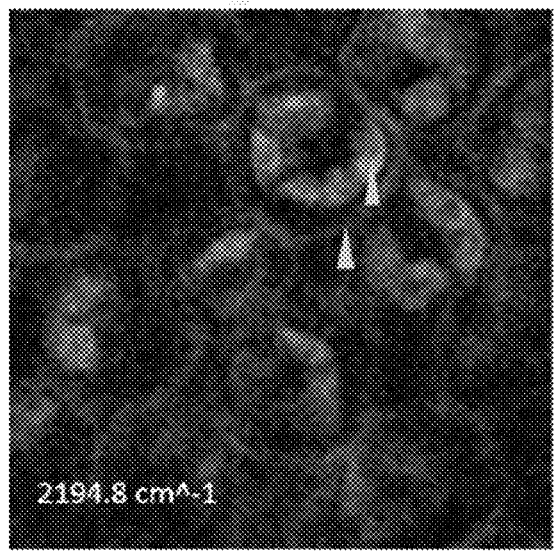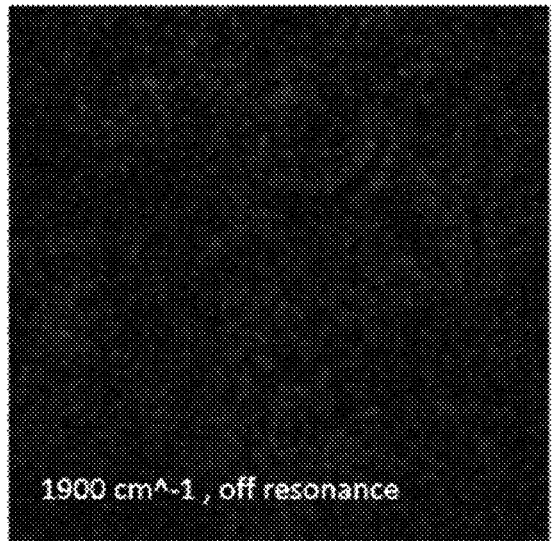
Figure 15

1705    1710

```
2900   ┌─────────────────────────────────────────────────┐
       │         Administering Heavy Water To Plants      │──── 2905
       └─────────────────────────────────────────────────┘
                             │
                             ▼
       ┌─────────────────────────────────────────────────┐
       │  Facilitating Sufficient Time For The Plant Leaves To  │──── 2910
       │  Incorporate D2O Into Proteins And/or Lipids In Plant Leaves │
       └─────────────────────────────────────────────────┘
                             │
                             ▼
       ┌─────────────────────────────────────────────────┐
       │  Obtaining First SRS Raman Spectrum Of Plant Leaves To │──── 2915
       │  Obtain Baseline Values For Protein And/or Lipid Levels │
       └─────────────────────────────────────────────────┘
                             │
                             ▼
       ┌─────────────────────────────────────────────────┐
       │  Administering To Plant Compound Which May Inhibit Or │──── 2920
       │               Promote Plant Growth               │
       └─────────────────────────────────────────────────┘
                             │
                             ▼
       ┌─────────────────────────────────────────────────┐
       │  Obtaining Second SRS Raman Spectrum Of Plant Leaves To │──── 2925
       │  Obtain Subsequent Values For Protein And/or Lipid Levels │
       └─────────────────────────────────────────────────┘
```

Figure 29

SYSTEM, METHOD AND COMPUTER-ACCESSIBLE MEDIUM FOR USE OF HEAVY WATER AS A PROBE FOR IMAGING METABOLIC ACTIVITIES

CROSS-REFERENCE TO RELATED APPLICATION(S)

This application is a continuation of International Patent Application No. PCT/US2019/043935, filed on Jul. 29, 2019 that published as International Patent Publication No. WO 2020/023966 on Jan. 30, 2020, and also relates to and claims priority from U.S. Patent Application Nos. 62/711,197, filed on Jul. 27, 2018 and 62/819,192, filed on Mar. 15, 2019, the entire disclosures of which are incorporated herein by reference.

STATEMENT REGARDING FEDERALLY SPONSORED RESEARCH

This invention was made with government support under Grant No. EB020892 and EB016573, awarded by the National Institutes of Health. The government has certain rights in the invention.

FIELD OF THE DISCLOSURE

In one aspect, the present disclosure relates generally to heavy water, and more specifically, to exemplary embodiments of an exemplary system, method and computer-accessible medium for use of heavy water as a probe for imaging metabolic activities, both in vivo and in vitro.

BACKGROUND INFORMATION

Understanding the dynamics of metabolism in multicellular organisms can be beneficial to unraveling the mechanistic basis of many biological processes. Although metabolomic technologies can catalog thousands of metabolites residing in cells, nondestructive tools are limited for in situ visualization of metabolic activities, such as protein and lipid synthesis and degradation, at subcellular resolution in living organisms. Magnetic resonance spectroscopic imaging ("MRSI") and positron emission tomography ("PET") can provide metabolic information noninvasively and have wide oncological application but lack sufficient spatial resolution. (See, e.g., Reference 1). Microautoradiography and fluorescence microscopy can visualize metabolism at the single-cell level but utilizes radioactive and fluorescent labeling of the substrate, respectively; these labeling are often toxic to cells and often perturb the native metabolic processes. (See. e.g., Reference2). Nanoscale Secondary Ion Mass Spectrometry ("NanoSIMS") and the more recent multi-isotope imaging mass spectrometry ("MIMS") can measure the incorporation of nontoxic stable isotopes, like $^{15}N$ and $^{13}C$, at submicrometer resolution and spatially track the labeling of biomolecules; but both methods are destructive to living tissues and have limited resolvability for macromolecules. (See, e.g., References 3 and 4).

Thus, it may also be beneficial to provide an exemplary system, method and computer-accessible medium for use of heavy water as a probe, for use in Raman spectroscopy, bioorthoganol IR imaging, or other analytical methods, for imaging metabolic activities, which can overcome at least some of the deficiencies described herein above.

SUMMARY OF EXEMPLARY EMBODIMENTS

To that end, exemplary system, method and computer-accessible medium for using heavy water (i.e., $D_2O$) as a probe for imaging metabolic activities, both in vivo and in vitro, can be provided.

For example, when heavy water is administered to cells (e.g., whether in vivo, or in vitro), it can be incorporated into lipids, proteins, and/or genetic material produced by the cells during their normal life cycle.

The new proteins, lipids, DNA, and other macromolecules which incorporate heavy water-derived deuterium can have their own unique Raman spectrum, and the Raman spectrum can be detected and clustered in order to generate a "map" of newly synthesized macromolecules.

When subjected to Raman spectroscopic procedures, and using appropriate mathematical formulas, as disclosed herein, it can be possible to produce spectra where peaks associated, with lipids, proteins, and genetic material can be separated. The relative volume in each peak (measured, for example, by calculating the area under the curve) can be determined.

In some aspects, lipid molecules can be separated into different subtypes of lipids, such as saturated and unsaturated lipids, or further identify the exact type of lipids, for example, cholesterol and phospholipids.

In one exemplary embodiment of the present disclosure, a computer-implemented procedure can be used, in some aspects, with software and/or computer programs, for clustering out various macromolecules (e.g., lipids, proteins, and/or genetic material) in living organisms, including virus, bacteria, nematodes, fungus, yeast, plants, animals, and human beings, including whole organisms, and isolated cells/tissue derived from these organisms.

For example, when organisms, or cells/tissue derived from the organisms, can be first administered heavy water, so as to produce lipids, proteins, and/or genetic material which incorporate deuterium, baseline measurement of the amounts of lipids, proteins, and/or genetic material can be determined.

Following exposure of the organisms, or cells/tissue derived from the organisms, to one or more compounds (e.g., while continuing to administer heavy water), a second measurement can be taken to determine whether the relative amounts of lipids, proteins and/or genetic material have changed relative to the baseline amounts. Differences in the amount of lipids, proteins, and/or genetic material can be used in a variety of diagnostic and/or theranostic methods.

In some exemplary embodiments, additional measurements can be measured over time, for example, after repeated exposure, as might be the case when a patient can be treated for a disease using one or more compounds. In other exemplary embodiments, rising dosage studies can be performed to determine, for example, an optimal range of drug concentrations to bring about a desired therapeutic effect, while avoiding toxicity.

According to certain additional exemplary embodiments of the present disclosure, the information on differences in the relative amounts of lipids, proteins, and/or genetic material before and after administration of the one or more compounds can be used to determine whether a particular therapeutic regimen can be effective in treating an individual patient, and/or whether a putative drug candidate has efficacy and/or toxicity.

In some exemplary embodiments of the present disclosure, the effectiveness of a putative treatment for a given disease can be determined. Representative diseases include cancer, heart disease, stroke, neurodegenerative diseases such as Alzheimer's disease and Parkinson's disease, neurotropic viral infections, stroke, paraneoplastic disorders, traumatic brain injury and multiple sclerosis, and infections by viruses, bacteria, fungi, prions or nematodes, endocrinology and metabolic diseases such as diabetes and diabetic complications, gout, type 1 & type 2 diabetes, obesity, metabolic syndrome, growth disorders, dyslipidemia hypogonadism, rare metabolic diseases. For example, biological samples containing bacteria, fungi, virus, or nematode can be subjected to one or a plurality of putative treatment regimens, and, where the levels of lipids, proteins and/or genetic material after treatment can be substantially different than baseline, an effective treatment regimen can be identified, and, in some embodiments, administered to a patient. The determination can be performed stepwise, or in parallel, for example, using high-throughput screening methods.

According to a further exemplary embodiment of the present disclosure, a method can be used to determine whether a patient has viral or bacterial meningitis. Administration of an antibiotic to a patient with viral meningitis may not be expected to result in any significant change in relative amounts of lipid, protein, or genetic material in a biological sample, such as a sample of cerebrospinal fluid, in a patient. However, if the patient has bacterial meningitis, a significant change can be expected to be observed. In this manner, the method provides a rapid screening method to determine whether a patient has viral or bacterial meningitis, and facilitates timely and effective treatment to be administered.

In another exemplary embodiments of the present disclosure, for example, with respect to drug resistant microbial infections, it can be possible to follow various treatment regimens real-time, and determine whether they can be effective in treating the infections. This can provide an alternative, for example, to genetically screening a virus, such as HIV HBV or HCV, present in a patient's blood or other biological fluid, to determine specific mutations associated with drug resistance, or to administering an antibiotic to a patient hoping it can be effective, only to find out the bacteria can be resistant to this particular antibiotic.

In another aspect, when used in cancer diagnostics, an evaluation can be performed to determine whether a given therapy can be effective against a tumor by administering heavy water to a patient, facilitating time for deuterium in the heavy water to become incorporated in lipids, proteins, and/or genetic material, and taking a baseline Raman spectra of the tumor. Following treatment with a putative chemotherapeutic agent, or combination of agents, further spectra can be utilized, and determination can be made as to whether the relative amounts of one or more of the lipid, protein and/or genetic material have changed. Changes in these relative amounts of one of more of the lipid, protein, and/or genetic material can be indicative that the chemotherapeutic method can be working. Repeated additional spectra can be obtained over the course of the treatment.

In still another exemplary embodiments of the present disclosure, the measurements of the relative levels of lipid, protein and/or genetic material can be obtained using surface enhanced Raman spectroscopy ("SERS"). In some aspects of this embodiment, the spectra can be obtained in vivo. In other aspects of this embodiment, the spectra can be obtained in vitro, by taking samples of one or more biological fluids after administration of heavy water to the patient, and both before and after exposure to a putative chemotherapeutic agent or combination of agents.

For example, drugs can be evaluated for their ability to inhibit tumor growth. Using heavy water and vibrational imaging and spectroscopy, the metabolic changes of tumor cells can be detected before and after the treatment and find out which drug can be the most effective one for inhibiting tumor growth.

In one exemplary embodiment of the present disclosure, such exemplary evaluation can be performed in vivo, where it can be possible to also use the spectroscopic method to determine the size of the tumor, and note whether the tumor can be growing, shrinking, or staying approximately the same size, throughout the duration of the chemotherapy.

This exemplary method can also be applied for detecting and diagnosing various types of cancers and separating subtypes of a certain cancer, based on its capability of detecting the metabolism differences between various cancer and normal cells and tissues. For example: breast cancer has many subtypes such as luminal A breast cancer (e.g., estrogen-receptor and/or progesterone-receptor positive, HER2 negative), and luminal B breast cancer (e.g., estrogen-receptor and/or progesterone-receptor positive, either HER2 positive or HER2 negative with high levels of Ki-67, generally grow slightly faster than luminal A), and triple negative breast cancer (e.g., all estrogen-receptor, progesterone receptor, and HER2 can be negative), etc.

According to a further exemplary embodiments of the present disclosure, the method can be used to detect differences in metabolism between cancer and normal healthy cells and tissues. In another exemplary aspect, a patient has more than one type of breast cancer cell types, where the metabolic activities of the different types of cancer can also be different, and the effectiveness of therapy against each of these breast cancer cell types can be determined.

In some embodiments, physicians can select appropriate treatment methods based on detecting a subtype of breast cancer, or other cancers. Applying the heavy water labeling and vibrational imaging of the cancer patient's tissue sample, it can be possible to determine which subtypes of cancer can be present. This can assist a physician to perform a proper diagnosis, and determine which treatment method to administer.

In other exemplary embodiments of the present disclosure, the safety of a compound can be determined. For example, it can be possible to expose a patient, such as, a human or non-human animal patient, cells/tissue obtained from a patient, a plant, or plant matter obtained from the plant, or a microbial organism, such as bacteria, fungi, or virus, to heavy water for a sufficient time that heavy water can be incorporated into the lipids, protein, and/or genetic material.

Some initial spectra can be obtained to determine a baseline value of the relative amounts of lipids, proteins and/or genetic material, either in vivo or in vitro. Following administration of a compound of interest, a second spectra can be obtained, and a second value of the relative amounts of lipids, proteins and/or genetic material, either in vivo or in vitro, can be obtained. There can be a correlation between the levels of lipids, proteins and/or genetic material and the toxicity of the compound to the patient, cells/tissue obtained from the patient, plant, plant matter, or microbial organisms.

Compounds which do not appear to adversely affect the relative amounts of lipids, proteins and/or genetic material can be deemed relatively non-toxic. In some aspects, the tests can be continued for a predetermined period of time while the compound can be continuously administered, either at the same dose, or at different doses (e.g., rising dosage studies). In other aspects, once an initial screen has identified compounds which appear to be non-toxic, and, optionally, other compounds which appear to be toxic, confirmatory toxicology studies can be performed on those compounds which appear to be non-toxic.

Toxicology studies can be performed, for example, in in vivo or in vino models, plant models, animal models, and human studies, such as Phase I, II, and III clinical trials.

Where a patient may not be suffering from a disease, and the interest in the evaluation can be to determine drug toxicity, changes from baseline can indicate that the drug has some toxicity. Where the second sample has minimal changes from baseline, such can indicate that the drug can be relatively non-toxic.

A formal toxicology study using other methods of determining drug toxicity can optionally then be performed on one or more drugs that appear to be relatively non-toxic based on this preliminary screen. This approach can be relatively beneficial when screening combinatorial libraries of compounds, as it can facilitate a quick identification of compounds which can be relatively non-toxic.

According to still other exemplary embodiments of the present disclosure, this approach can be combined with a binding assay, where the drug can be screened for its ability to bind, as a ligand, to a particular biological target, such as a receptor. If a compound can be relatively non-toxic, but has poor binding to a desired biological target, or vice versa, a determination can be made as to whether the compound can be a good candidate to advance to further studies.

In another exemplary embodiment of the present disclosure, such approach can be combined with an assay to determine whether the compound has desired activity once bound to the receptor. For example, a compound can bind to a receptor and function as an agonist, a partial agonist, an inverse agonist, an antagonist, or an allosteric inhibitor. Using a combination of assays, it can be possible to identify compounds which have relatively low toxicity, bind to the proper receptors, and have the desired activity once bound to the receptors.

According to a still further exemplary embodiments of the present disclosure, it can also be to perform an additional assay to determine a compound's selectivity for a desired receptor over other less desired receptors. This combination of assays can determine relative toxicity of putative therapeutic compounds, the ability of the compounds to bind to desired receptors, the activity of the compounds once bound, and the selectivity of the compound for the desired receptor versus other receptors, such as those which can cause unwanted side effects.

One or more of these aspects can be applied for drug screening. For various diseases, the drug treatment can alter the metabolic activities of cells and tissues. The heavy water labeling with vibrational imaging and spectroscopy can tell the metabolic activities of newly synthesized deuterium labeled lipids, protein, DNA and carbohydrates. It can be used in both in vitro cell culture and in vivo experiments on animals, even human beings, cells or tissue derived from the animals or human beings, or biological fluids derived from the animals or human beings.

Where the biological organism can be a bacteria, one aspect of this method involves screening putative antibiotics to determine whether the bacteria has antibiotic tolerance/resistance to a particular antibiotic, and can be used to help a treating physician determine the most effective antibiotic, or combination of antibiotics, to treat a bacterial infection.

A biofilm can be any group of microorganisms in which cells stick to each other, and these cells often adhere to a surface, which can be a biological surface, such as the inside of a patient's lungs. Lung infection can be the main cause of morbidity and mortality in patients with cystic fibrosis and can be mainly dominated by *Pseudomonas aeruginosa*. The biofilm mode of growth makes eradication of the infection extremely difficult, and it causes a chronic inflammation in the airways. In addition to the difficulty of treating biofilms with conventional antibiotic therapy, treating biofilms can also be hindered by the rising antibiotic resistance among pathogens. The methods described herein can be useful in studying the metabolic heterogeneity in biofilms, or other microbiota, for example, as a way to determine effective treatment methods.

In an exemplary embodiments of the present disclosure, photosynthesis can be evaluated by following the relative amounts of lipids, proteins, and/or genetic material in various plants and algae. For example, plants and/or algae can be exposed to heavy water for a sufficient amount of time for deuterium to be incorporated into plant or algal lipids, proteins, and/or genetic material. A baseline value of the relative amounts of lipids, proteins and/or genetic material in the plants and/or algae can be measured. Then, the plants and/or algae can be exposed to one or more conditions, such as exposure to different light sources and/or different light duration, and/or plant growth regulators which either accelerate plant growth, or can be herbicidal in nature. Following exposure to these conditions, a second value of the relative amounts of lipids, proteins, and/or genetic material in the plants and/or algae can be measured. Differences in the levels of lipids, proteins, and/or genetic material before and after exposure to the one or more conditions can show, for example, whether plant or algal growth can be accelerated or diminished.

By separately visualizing the newly synthesized protein, lipids, and carbohydrates, the conditions for photosynthesis can be optimized. This information can be used to optimize production of algal oil, which can be used directly as a fuel, or converted to biodiesel fuel, an alternative to liquid fossil fuels, and/or to commonly known biofuel sources such as corn and sugarcane. In one exemplary embodiment of the present disclosure, the method can be performed in a high throughput manner, and can be used to study which compartment of an algae cell can be producing lipids (e.g., oil), and under what conditions oil production can be optimized. In another exemplary embodiment of the present disclosure, in addition to or in place of SERS, photosynthesis can be studied using heavy water combined with vibrational imaging and spectroscopy.

In some exemplary embodiments of the present disclosure, rather than using SERS, the spectra can be obtained using other vibrational imaging procedures, including, but not limited to, tip-enhanced Raman microscopy ("TERS"), Fourier-Transform Infrared Imaging, AFM-IR, Optical Photothermal IR microscopy, Infrared Photo Induced Force Microscopy, and Peak Force Infrared Microscopy, particularly where the procedure can be used to study metabolic activity.

Additionally, with an exemplary system, method and computer-accessible medium according to an exemplary embodiment of the present disclosure, it is possible to, for example, receive a Raman imaging signal obtained from the skin of a patient(s), separating the Raman imaging signal into a lipid signal and a protein signal, and determine a metabolic activity of the skin based on the lipid signal and the protein signal. The Raman imaging signal can be a stimulated Raman scattering imaging signal. The Raman imaging signal from the skin can be based on a consumption of heavy water by the patient(s). The Raman imaging signal can be based on a vibrational tag(s).

Further, with a further exemplary method for determining information regarding a biological structure of a patient(s) according to an exemplary embodiment of the present disclosure, it is possible to, for example, administer a vibrational probe(s) to a patient(s), imaging the biological structure of the patient(s) using a stimulated Raman scattering (SRS) imaging procedure, receive a SRS signal from the biological structure of the patient(s), separate the SRS signal into a lipid signal and a protein signal, and determine the information based on the lipid signal and the protein signal. The imaging of the biological structure can be performed using a handheld SRS device. The vibrational probe(s) can include (i) heavy water or (ii) glucose. The biological structure can be (i) skin of the patient(s), (ii) skin cells of the patient(s), or (iii) a bodily fluid of the patient(s). The bodily fluid can include (i) blood or (ii) plasma. A drug(s) can be administered to the patient(s), and the information can include an efficacy of the drug(s) on the biological structure.

In addition, an exemplary handheld device according to an exemplary embodiment of the present disclosure can be provided, which can include, for example, an optical emitter configured to generate (i) a Raman imaging signal or (ii) an infrared (IR) imaging signal, an optical detector configured to receive a resultant signal that can be based on the Raman imaging signal or the infrared imaging signal, and a hardware computing arrangement configured to split the resultant signal into a protein signal and a lipid signal, and determine information regarding a biological structure(s) based on the protein signal and the lipid signal. The Raman imaging signal can be a stimulated Raman scattering imaging signal.

Further, with yet another exemplary method for determining the efficacy of chemotherapy according to an exemplary embodiment of the present disclosure, it is possible to, for example: a) administer an effective amount of 20 to a patient who has a tumor, where a brain of the patient can be visualizable using SRS Raman imaging procedures, and allow a predetermined period of time for the $D_2O$ to become incorporated into the tumor, b) obtain a first SRS Raman spectrum of the tumor, where first signals associated with the first spectrum can be acquired, at least, from 2135 $cm^{-1}$, 2185 $cm^{-1}$, and 2210 $cm^{-1}$, which signals can correspond to lipids, proteins, and DNA, respectively, c) un-mix the first signals so as to form separate spectral peaks for the lipids, proteins, and DNA in the tumor, d) administer chemotherapy to the patient for a suitable time such that, if the chemotherapy is effective, changes in levels of the lipid, protein or DNA in the tumor can be expected to vary from the respective levels before chemotherapy is administered, e) continuously administer an effective amount of $D_2O$ to the patient while the patient is treated with the chemotherapy, so as to allow deuterium to become incorporated into one or more of the lipid, protein, or DNA found in the tumor, f) obtain a second SRS Raman spectrum of the tumor, where second signals associated with the second spectrum are acquired, at least, from 2135 $cm^{-1}$, 2185 $cm^{-1}$, and 2210 $cm^{-1}$, and where the second signals correspond to the lipids, proteins, and DNA, respectively, and g) compare the first and second SRS Raman spectra, where significant changes in the amount of at least one of the lipid, protein or DNA can be indicative of the success of the chemotherapy, and where insignificant changes in the amount of lipid, protein or DNA can be indicative of the lack of success of the chemotherapy.

In some exemplary embodiments of the present disclosure, the comparison of the first and second SRS Raman spectra show that the chemotherapy is effective, the method further comprises continuing to treat the patient with the chemotherapy, and where the comparison of the first and second SRS Raman spectra show that the chemotherapy is ineffective, the method further comprises discontinuing treatment with the chemotherapy. Treatment with the chemotherapy can be discontinued, steps a-f are repeated with a different chemotherapy. The cancer can be breast cancer.

With an exemplary method for determining the efficacy of a putative therapy for Alzheimer's disease according to an exemplary embodiment of the present disclosure, it is possible to, for example, a) administer an effective amount of $D_2O$ to a patient who has Alzheimer's disease, where a brain of the patient is visualizable using SRS Raman imaging procedures, and allow a predetermined period of time for the $D_2O$ to become incorporated into a tissue of the brain, b) obtain a first SRS Raman spectrum of the brain, where first signals associated with the first spectrum are acquired, at least, from 2135 $cm^{-1}$, 2185 $cm^{-1}$, and 2210 $cm^{-1}$, and wherein the signals correspond to lipids, proteins, and DNA, respectively, c) un-mix the first signals so as to form separate spectral peaks for the lipids, proteins, and DNA in the tissue, d) administer a putative therapy to the patient for a particular time period such that, if the therapy is effective, changes in levels of at least one of the lipid, protein or DNA levels in the brain are expected to vary from the respective levels before therapy is administered, e) continuously administer an effective amount of $D_2O$ to the patient while the patient is treated with the therapy, so as to allow deuterium to become incorporated into one or more of the lipid, protein, and DNA found in the brain tissue, f) obtain a second SRS Raman spectrum of the brain tissue, where second signals associated with the second spectrum are acquired, from 2135 $cm^{-1}$, 2185 $cm^{-1}$, and 2210 $cm^{-1}$, where the second signals correspond to the lipids, proteins, and DNA, respectively, and g) compare the first and second SRS Raman spectra, wherein significant changes in the amount of at least one of the lipid, protein or DNA provide information relative to whether the therapy has decreased the severity of the disease, decelerated or stopped the progression of the disease, or has not slowed down or decreased the severity of the disease.

In some exemplary embodiments of the present disclosure, the protein levels can comprise proteins associated with beta-amyloid plaque, where a decrease in the amount of beta-amyloid plaque is indicative that the therapy is decreasing the severity of the disease, relatively unchanged amounts of beta-amyloid plaque are indicative that the therapy has decelerated or stopped the progression of the disease, and increased amounts of beta-amyloid plaque are indicative that the therapy has not decelerated or decreased the severity of the disease.

Additionally, with still a further exemplary method for determining the efficacy of a putative therapy for a metabolic disease according to an exemplary embodiment of the present disclosure, it is possible to, for example, a) administer an effective amount of $D_2O$ to a patient who has a metabolic disease, where lipid levels of the patient are visualizable over time using SRS Raman imaging procedures, and allow a predetermined amount of time for the $D_2O$ to become incorporated into lipids of the patient, b) obtain a first SRS Raman spectrum of a biological fluid comprising lipids, where first signals associated with the first spectrum are acquired, at least, from 2135 $cm^{-1}$, 185 $cm^{-1}$, and 2210 $cm^{-1}$, which signals correspond to lipids, proteins, and DNA, respectively, c) un-mix the first signals so as to form separate spectral peaks for the lipids, proteins, and DNA in the biological sample, d) administer a putative therapy to the patient for a suitable time such that, if the therapy is effective, changes in levels of at least one of the lipid, protein or DNA levels in one or more biological samples of the patient are expected to vary from the respective levels before therapy is administered, e) continuously administer an effective amount of $D_2O$ to the patient while the patient is treated with the therapy, so as to allow deuterium to become incorporated into one or more of the lipid, protein or DNA found in one or more of the biological samples, f) obtain a second SRS Raman spectrum of the brain tissue, where second signals associated with the second spectrum are acquired, at least, from 2135 $cm^{-1}$, 2185 $cm^{-1}$, and 2210 $cm^{-1}$, and where the second signals correspond to lipids, proteins, and DNA, respectively, and g) compare the first and second SRS Raman spectra, where significant changes in the amount of lipid, protein and/or DNA provide information relative to whether the therapy has decreased the severity of the disease, decelerated or stopped the progression of the disease, or has not decelerated or decreased the severity of the disease.

In certain exemplary embodiments of the present disclosure, the treatment, if successful, increases HDL levels, decreases LDL levels, or both, and differences in the baseline values of HDL and LDL in the SRS Raman spectra are compared with values of HDL and LDL in one or more of the biological sample taken after a treatment is administered. The biological fluid can be blood plasma.

Further, with yet another exemplary method for determining the efficacy of an antimicrobial compound according to an exemplary embodiment of the present disclosure, it is possible to, for example, a) administer an effective amount of $D_2O$ to a patient who has a microbial infection, and allowing a predetermined amount of time for the $D_2O$ to become incorporated into the biological organism, b) obtain a sample of a biological fluid comprising a microbe responsible for the microbial infection, and obtain a first SRS Raman spectrum of the fluid, where first signals associated with the first spectrum are acquired, at least, from 2135 $cm^{-1}$, 2185 $cm^{-1}$, and 2210 $cm^{-1}$, and where the first signals correspond to lipids, proteins, and DNA, respectively, c) un-mix the second signals so as to form separate spectral peaks for the lipids, proteins, and DNA in the biological fluid, d) administer a putative antimicrobial therapy to the patient for a particular time such that, if the therapy is effective, changes in levels of at least one of the lipid protein or DNA in the microbe in the biological fluid are expected to vary from the respective levels before therapy is administered, e) continuously administer an effective amount of $D_2O$ to the patient while the patient is treated with the therapy, so as to allow deuterium to become incorporated into one or more of the lipid, protein or DNA found in the microbe present in the fluid, f) obtain a second sample of the biological fluid from the patient, g) obtain a second SRS Raman spectrum of the fluid, where second signals associated with the second spectrum are acquired, at least, from 2135 $cm^{-1}$, 2185 $cm^{-1}$, and 2210 $cm^{-1}$, and where the second signals correspond to the lipids, proteins, and DNA, respectively, and h) comparing the first and second SRS Raman spectra, where significant changes in the amount of at least one of the lipid, protein or DNA are indicative of the success of the therapy, and where insignificant changes in the amount of at least one of the lipid, protein or DNA are indicative of the lack of success of the therapy.

In some exemplary embodiments of the present disclosure, the microbe can be a virus selected from the group consisting of HIV, HBV, and HCV. The microbe can be a bacteria. The bacteria can be a drug-resistant bacteria. Two or more putative antimicrobial therapies can be evaluated in parallel. It can be unclear whether the microbe is a virus, bacteria, or fungus, and one or more putative therapies selected from the group consisting of antivirals, antibacterials, and antifungals are administered to determine the type of infection, and wherein the type of infection is bacterial when an antibacterial therapy is successful, the type of infection is viral when an antiviral therapy is successful, and the type of infection is fungal when an antifungal therapy is successful. A patient being evaluated has either viral or bacterial meningitis, and an antibacterial therapy is administered, where if the therapy is successful, the patient is diagnosed as having bacterial meningitis and is treated with the antibacterial therapy, and if the therapy is unsuccessful, the patient is diagnosed as having viral meningitis.

In addition, using another exemplary method for determining the efficacy of a putative therapy for multiple sclerosis according to an exemplary embodiment of the present disclosure, it is possible to, for example, a) administer an effective amount of $D_2O$ to a patient who has multiple sclerosis, where myelin levels of the patient are visualizable over time using SRS Raman imaging procedures, and allow a predetermined amount of time for the $D_2O$ to become incorporated into myelin of the patient, b) obtain a first SRS Raman spectrum of the patient's brain or nerve tissue, where first signals associated with the first spectrum are acquired, at least, from 2135 $cm^{-1}$, 0.2185 $cm^{-1}$, and 2210 $cm^{-1}$, and wherein the first signals correspond to lipids, proteins, and DNA, respectively, c) un-mix the first signals so as to form separate spectral peaks for the lipids, proteins, and DNA in the biological sample, d) administer a putative therapy to the patient for a predetermined time such that, if the therapy is effective, changes in levels of at least one of the lipid, protein or DNA in a brain or nerve tissue of the patient are expected to vary from the respective levels before therapy is administered, e) continuously administer an effective amount of $D_2O$ to the patient while the patient is treated with the therapy, so as to allow deuterium to become incorporated into one or more of the lipid, protein, and DNA found in the brain or nerve tissue, f) obtaining a second SRS Raman spectrum of the brain or nerve tissue, where second signals associated with the second spectrum are acquired, at least, from 2135 $cm^{-1}$, 2185 $cm^{-1}$, and 2210 $cm^{-1}$, and where the second signals correspond to lipids, proteins, and DNA, respectively, and g) compare the first and second SRS Raman spectra, where significant changes in the amount of at least one of the lipid, protein or DNA provide information relative to whether the therapy has decreased the severity of the disease, decelerated or stopped the progression of the disease, or has not decelerated or decreased the severity of the disease.

In addition, with a further exemplary method for evaluating the effectiveness of a compound on a plant according to an exemplary embodiment of the present disclosure, it is possible to, for example, a) administer an effective amount of $D_2O$ to a plant which has levels of at least one of lipids, proteins or genetic material which is visualizable using one or more SRS Raman imaging procedures, and allow a predetermined amount of time for the $D_2O$ to become incorporated into the plant, b) obtain a first SRS Raman spectrum of the plant, where first signals associated with the first spectrum are acquired, at least, from 2135 $cm^4$, 2185 $cm^{-1}$, and 2210 $cm^{-1}$, and wherein the first signals correspond to lipids, proteins, and DNA, respectively, c) un-mix the first signals so as to form separate spectral peaks for the ipids, proteins, and DNA in the plant, d) administer a compound to the plant which can assist the plant grow, or inhibit the plant growth, for a particular period of time such that, if the compound is effective, changes in levels of at least one of the lipid, protein or DNA in the tumor are expected to vary from their levels before the compound is administered, e) continuously administer an effective amount of $D_2O$ to the plant while the plant is treated with the compound, so as to allow deuterium to become incorporated into one or more of the lipid, protein, and DNA found in the plant, f) obtain a second SRS Raman spectrum of the plant, where second signals associated with the second spectrum are acquired, at least, from 2135 $cm^{-1}$, 2185 $cm^{-1}$, and 2210 $cm^{-1}$, and wherein the second signals correspond to lipids, proteins, and DNA, respectively, and g) compare the first and second SRS Raman spectra, where significant changes in the amount of at least one of the lipid, protein or DNA are indicative of the success of the compound in helping the plant grow, or inhibiting plant growth, and where insignificant changes in the amount of at least one of the lipid, protein or DNA are indicative of the lack of success of the compound in inhibiting or promoting plant growth.

Further, using still another exemplary method for monitoring plant growth or inhibition with monitoring the protein and/or lipids content, and their turnover, in plant leaves, where the protein and/or lipids content is monitored by procedures according to an exemplary embodiment of the present disclosure, it is possible to, for example, a) administer heavy water to the plants; b) facilitate sufficient time for the plant leaves to incorporate $D_2O$ into proteins and/or lipids in the plant leaves; c) obtain a first SRS Raman spectrum of the plant leaves to obtain baseline values for protein and/or lipid levels; d) administer to the plant a compound which may inhibit or promote plant growth, while continuously administering heavy water to the plant; and e) obtain a second SRS Raman spectrum of the plant leaves to obtain subsequent values for protein and/or lipid levels, where a negative change in the levels of at least one of proteins or lipids is indicative that the plant growth is being inhibited, and where a positive change in the levels of at least one of proteins or lipids is indicative that the plant growth is being promoted.

Additionally, with additional exemplary system, method and computer-accessible medium for generating (i) an image(s) of a target molecule(s), or (ii) a plurality of spectra related to the target molecule(s) according to an exemplary embodiment of the present disclosure, it is possible to, for example, receive digital information related to a labelling of the target molecule(s), and generate the (i) the image(s) of the labelled target molecule(s) or (ii) the spectra related to the labelled target(s) molecule using (i) an infrared (IR) imaging procedure, or (ii) an IR spectroscopic procedure. A further image(s) of the labelled target molecule(s) can be generated using a stimulated Raman imaging procedure, or (ii) a further plurality of spectra related to the labelled target molecule(s) can be generated using the stimulated Raman imaging procedure.

In some exemplary embodiments of the present disclosure, the digital information can relate to a labelling of the target molecule(s) using (i) carbon-deuterium, (ii) carbon 13, (iii) nitrile, (iv) azide, or (iv) fluorine. The image(s) can include an image of a tumor. A metabolic contrast associated with the target molecule(s) can be determined based on the image(s) or the spectra. The digital information can include information related to the target molecule(s) vibrating in a cell-silent spectral region. The cell-silent spectral region can be about 1800-2500 $cm^{-1}$.

Further, with another exemplary method for generating an image(s) of a molecule(s) or a plurality of spectra related to the target molecule(s) according to an exemplary embodiment of the present disclosure, it is possible to, for example, administer a composition(s) to a patient(s), where the composition(s) can include a vibrational chemical tag(s) configured to label the target molecule(s), and generate the image(s) of the labelled target molecule(s) or the spectra related to the labelled target molecule(s) using an infrared (IR) imaging procedure based on the vibrational chemical tag(s) or an IR spectroscopic procedure based on the vibrational chemical tag(s).

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which:

FIG. 1C is a set of exemplary images and an associated graph illustrating the signal-to-noise ratio for SRS microscopic signals according to an exemplary embodiment of the present disclosure;

FIG. 1D is a set of exemplary images of live sebaceous glands from under the ear skin of intact mice according to an exemplary embodiment of the present disclosure;

FIG. 1E is a set of exemplary images of live *C. elegans* larvae according to an exemplary embodiment of the present disclosure.

FIG. 3B is a set of exemplary SRS microscopic images collected from the CDL and CDP channel of COS-7 cells according to an exemplary embodiment of the present disclosure;

FIG. 3C is an exemplary chart of CDL intensity before and after un-mixing according to an exemplary embodiment of the present disclosure;

FIG. 3D is an exemplary chart of CDP intensity before and after un-mixing according to an exemplary embodiment of the present disclosure;

FIG. 3E is a set of exemplary images of xenograft colon tumor tissues from mice drinking $D_2O$ according to an exemplary embodiment of the present disclosure;

FIG. 3F is a set of exemplary images of sebaceous gland tissues from mice drinking $D_2O$ according to an exemplary embodiment of the present disclosure;

FIG. 3G is a set of exemplary images of CHL/CHP un-mixing according to an exemplary embodiment of the present disclosure;

FIG. 4D is an exemplary chart of the quantification of the mean intensity over the entire worm body according to an exemplary embodiment of the present disclosure;

FIG. 5A is a set of exemplary images of car skin harvested from adult mice according to an exemplary embodiment of the present disclosure;

FIG. 5B is an exemplary chart of CDL/CHL % for FIG. 5A according to an exemplary embodiment of the present disclosure;

FIG. 5C is a set of exemplary images of the internal capsule of a mouse brain according to an exemplary embodiment of the present disclosure;

FIG. 5D is an exemplary chart illustrating the quantification of myelination activities in different brain regions according to an exemplary embodiment of the present disclosure;

FIG. 5E is a set of exemplary images of white and brown adipose tissue from juvenile SD and adult SD mice according to an exemplary embodiment of the present disclosure.

FIG. 5F is an exemplary chart of the CDL/CHL % for FIG. 5E according to an exemplary embodiment of the present disclosure;

FIG. 5G is a set of exemplary images of adipose tissue from wild-type and ob/ob adult mice according to an exemplary embodiment of the present disclosure;

FIG. 5H is an exemplary chart of the CDL/CHL % for FIG. 5G according to an exemplary embodiment of the present disclosure;

FIG. 7A is an exemplary diagram illustrating germine development according to an exemplary embodiment of the present disclosure;

FIG. 7B is a set of exemplary images of L4 animals and day 0 adults grown on $D_2O$ plates according to an exemplary embodiment of the present disclosure;

FIG. 7C is an exemplary chart of mean intensity ratios according to an exemplary embodiment of the present disclosure;

FIG. 7D is an exemplary chart of CD signals according to an exemplary embodiment of the present disclosure;

FIG. 7E is a set of exemplary SRS microscopic images of adults after $D_2O$ probing according to an exemplary embodiment of the present disclosure;

FIGS. 8A-8C is a set of exemplary SRS microscopic signal images and the colocalization with a fluorescence reporter according to an exemplary embodiment of the present disclosure;

FIGS. 8D and 8E are exemplary charts of intensity profiles according to an exemplary embodiment of the present disclosure;

FIG. 9A is a set of exemplary images of intracranial xenograft glioblastoma in a mouse brain according to an exemplary embodiment of the present disclosure;

FIG. 9B is a set of exemplary images of the tumor-skin boundary according to an exemplary embodiment of the present disclosure;

FIG. 9C is a set of exemplary images of the interior of the colon tumor xenograft according to an exemplary embodiment of the present disclosure;

FIG. 9D is a set of charts illustrating intensity profile quantities according to an exemplary embodiment of the present disclosure;

FIG. 10A is an exemplary chart of CellTiter-Glo Luminescent Cell Viability Assay according to an exemplary embodiment of the present disclosure;

FIG. 10B is an exemplary chart of the lethality of ochlorite-prepared eggs onto NGM plates made of different concentration of $D_2O$ according to an exemplary embodiment of the present disclosure;

FIG. 10C is an exemplary chart of the sterility as the percentage of fourth stage larva ("L4") that became sterile after being transferred to $D_2O$ plates according to an exemplary embodiment of the present disclosure;

FIG. 10D is an exemplary chart of the brood size which shows the effects on meiosis determined by counting the total number of viable progeny one animal produced according to an exemplary embodiment of the present disclosure;

FIG. 11A is an exemplary chart of spontaneous Raman signal of extracted lipids, proteins, and DNA from $D_2O$-treated HeLa cells according to an exemplary embodiment of the present disclosure;

FIG. 11B is an exemplary chart of normalized intensity of colon tumor tissues (e.g., from mice that drank 25% $D_2O$ for 15 days) before and after methanol wash according to an exemplary embodiment of the present disclosure;

FIG. 11C is an exemplary chart of normalized intensity for a methanol wash and signal normalization applied to mouse brain and pancreas tissues, in addition to tumor tissues according to an exemplary embodiment of the present disclosure;

FIG. 11D is a set of exemplary SRS images of methanol-washed colon tumor tissues according to an exemplary embodiment of the present disclosure;

FIG. 11E is a set of exemplary images of HeLa cells grown in 70% $D_2O$ DMEM according to an exemplary embodiment of the present disclosure;

FIG. 11F is a set of exemplary images of HeLa anisomycin according to an exemplary embodiment of the present disclosure;

FIG. 12A is a set of exemplary images of hypochlorite-prepared eggs of C. elegans according to an exemplary embodiment of the present disclosure;

FIG. 12B is a set of exemplary images of OP50 bacterial culture mixed with 4 mM D31-palmitic acid and then seeded onto NGM plates that contains 100% $H_2O$ according to an exemplary embodiment of the present disclosure;

FIG. 12C is an exemplary chart of the comparison of the CDL/CHL ratio for animals fed with D31-PA and the ones grown on $D_2O$ plates according to an exemplary embodiment of the present disclosure;

FIG. 15 is a set of exemplary images of CD signals of plant leaves from Origanum vulgare that were growing with 50% heavy water in nonmal water for 5 days and the Raman spectrum of the newly synthesized metabolites in the plant leaf according to an exemplary embodiment of the present disclosure;

FIG. 29 is an exemplary flow diagram of an exemplary method 2400 for monitoring plant growth or inhibition according to an exemplary embodiment of the present disclosure;

Figure 1A:
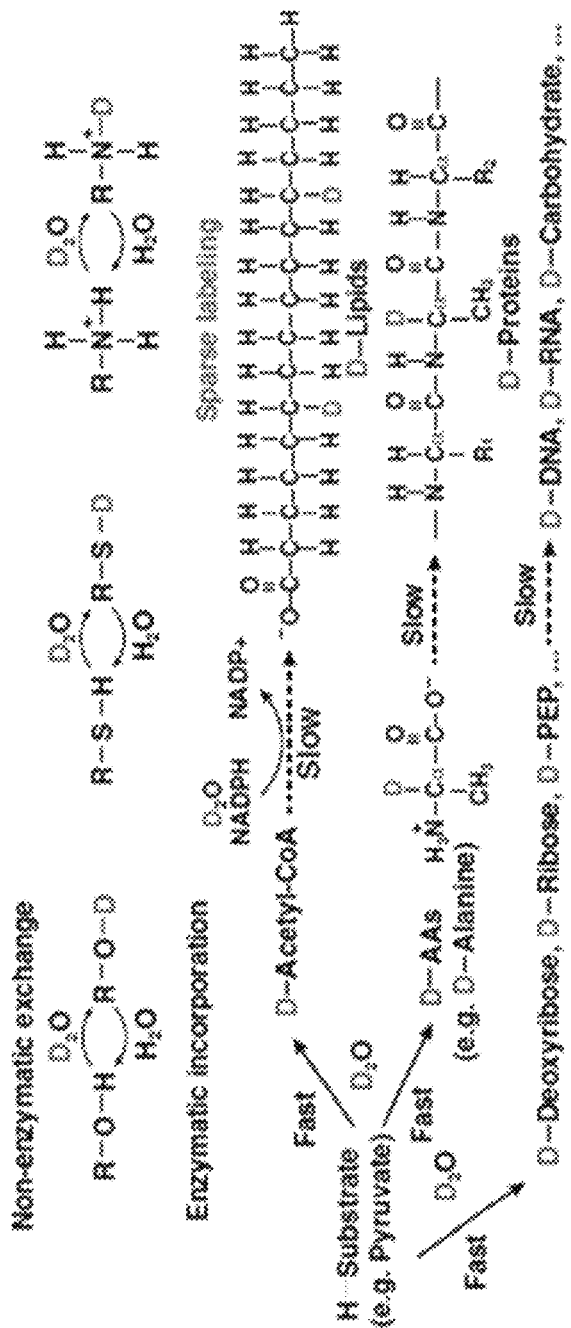
FIG. 1A is an exemplary molecular diagram according to an exemplary embodiment of the present disclosure.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures and the appended claims.

DETAILED DESCRIPTION OF EXEMPLARY EMBODIMENTS

The exemplary system, method, and computer-accessible medium, according to an exemplary embodiment of the present disclosure, can combine deuterium oxide probing and stimulated Raman scattering microscopy ("DO-SRS") to provide imaging contrast for visualizing metabolic dynamics in situ.

Through systematic investigation of the carbon-deuterium ("C-D") vibrational spectrum, Raman shifts associated with C-D bond-containing lipids, proteins, and genetic material, such as DNA and RNA, respectively, can be determined. By applying DO-SRS to living cells, tissue, animals, and plants, it can be possible to provide high sensitivity, noninvasiveness, subcellular resolution, compatibility with other imaging modality, and suitability for in vivo live imaging in mammals, plants, and microorganism, as well as in vitro imaging.

The exemplary DO-SRS can therefore offer a nondestructive, noninvasive, and background-free imaging method that can be used to visualize metabolic dynamics of proteins, lipids, and DNA simultaneously in a variety of model organisms and animals, without tissue bias.

Representative advantages can include its broad utility, high sensitivity, noninvasiveness, subcellular resolution, compatibility with other imaging modality, and suitability for in vivo live imaging in live cells, plants, microbes, animals, and humans, as well as in vitro imaging.

The exemplary DO-SRS can facilitate in situ visualization of de novo lipogenesis and protein synthesis in animals without tissue bias, representing a beneficial technical advance. In particular, the ability to simultaneously image newly synthesized lipids and proteins can facilitate new insights into the metabolic basis of several biological processes.

The exemplary system, method, and computer-accessible medium, according to an exemplary embodiment of the present disclosure, can utilize $D_2O$, which can be a superior probe to deuterium-labeled carbon substrates, in monitoring and imaging metabolic activities, because $D_2O$ does not perturb native metabolism, can freely diffuse into cells, and can be a non-carbon tracer that can probe de novo biosynthesis. For visualizing lipogenic activities, $D_2O$ can be superior than deuterated fatty acids ("D-FAs") as well as D-glucose (see, e.g., Reference 52), which can create hyperglycemia when used at high concentration and may not label newly synthesized lipids as efficient as $D_2O$ treatment.

The exemplary DO-SRS can be used to address a variety of biological questions. For example, when applied to heterogeneous tumor tissues, the exemplary DO-SRS can aid in identifying cancer stem cells that have particular patterns of metabolic activities, such as high lipogenic activities.

Label-free SRS was previously used to find that ovarian cancer stem cells had significantly increased levels of unsaturated lipids than non-stem cancer cells (see, e.g., Reference 53), and the exemplary DO-SRS provides higher sensitivity, and the ability to track metabolic dynamics.

The exemplary DO-SRS can be used with fluorescent labeling to monitor the metabolic activity of specific cells and lineages in situ. One particularly interesting problem can be the metabolic cooperation between glial cells and neurons. (See, e.g., Reference 54). In addition to the synthesis of lipids and proteins, the exemplary DO-SRS can also be used to monitor protein turnover, lipid consumption, and macromolecule degradation.

Although the exemplary DO-SRS can have relatively lower molecular specificity and sensitivity compared to mass spectrometry imaging ("MSI") methods (see. e.g., References 55-57), it can be used in conjunction with MSI methods because it can offer several advantages. The exemplary DO-SRS can provide straightforward and quantitative interpretation of total metabolic activities in three-dimensional living tissues, whereas MSI procedures can include destructive surface analysis, can involve more complicated computation than SRS imaging, and may not capture all D-labeled molecules equally due to certain bias towards easily ionized and desorbed analytes.

A major challenge for in vivo metabolic imaging can be the accessibility of tissues deep inside the body. Using devices similar to the coherent Raman scattering endoscopes (see e.g., Reference 58), the exemplary DO-SRS can be applied to visualize metabolic patterns of internal organs and to evaluate tumor metabolism through optical biopsy. Additionally, volumetric stimulated Raman projection ("SRP") microscopy and tomography (see, e.g., Reference 59) can facilitate in deep-tissue, large-volume, in vivo imaging (e.g., imaging cortical metabolism). The sensitivity of the exemplary system, method and computer-accessible medium can be high enough to operate in the range of low $D_2O$ enrichment that can be safe for humans. Given that SRS imaging has been demonstrated in humans before (see, e.g., Reference 60) the exemplary DO-SRS can have clinical application in tracking metabolic activities in humans.

The following detailed description is presented to enable any person skilled in the art to make and use the present disclosure. For purposes of explanation, specific nomenclature is set forth to provide a thorough understanding of the present invention. However, it can be apparent to one skilled in the art that these specific details are not required to practice the invention—Descriptions of specific applications are provided only as representative examples. The present disclosure is not intended to be limited to the exemplary embodiments shown, but is to be accorded the widest possible scope consistent with the principles and features disclosed herein.

Exemplary Raman Spectroscopy

Raman spectroscopy is a spectroscopic procedure used to study vibrational, rotational, and other low-frequency modes in molecular systems. In Raman spectroscopy, an approximately monochromatic beam of light of a particular wavelength range passes through a sample of molecules and a spectrum of scattered light can be emitted. The spectrum of wavelengths emitted from the molecule is called a "Raman spectrum" and the emitted light is called "Raman scattered light." A Raman spectrum can reveal electronic, vibrational, and rotational energy levels of a molecule. Different molecules can produce different Raman spectrums that can be used like a fingerprint to identify molecules and even determine the structure of the molecules.

As used herein, the term "Raman scattering" refers to a spectroscopic procedure used to observe vibrational, rotational, and other low-frequency modes in a system. It relies on inelastic scattering, or Raman scattering, of monochromatic light, for example, from a laser in the visible, near infrared, or near ultraviolet range. The laser light can interact with molecular vibrations, phonons or other excitations in the system, which can result in the energy of the laser photons being shifted up or down. The shift in energy can provide information about the vibrational modes in the system. A variety of optical processes, both linear and nonlinear in light intensity dependence, can be fundamentally related to Raman scattering. As used herein, the term "Raman scattering" includes, but is not limited to, "stimulated Raman scattering" ("SRS"), "spontaneous Raman scattering", "coherent anti-Stakes Raman scattering" ("CARS"), SERS, TERS or "vibrational photoacoustic tomography".

The exemplary SRS can be a sensitive vibrational imaging microscopy. By harnessing Einstein's stimulated emission process, the exemplary SRS can employ two-laser excitation (e.g., temporally and spatially overlapped Pump and Stokes lasers), boosting up the transition rate about 7 orders of magnitude as compared to the traditional spontaneous Raman microscopy, the transition process of which can be intrinsically weak (e.g., about 1.0 to about 12 orders of magnitude slower than fluorescence). The exemplary SRS can be a bond-selective procedure with high specificity, in contrast with the spontaneous Raman imaging which can be a spectrum-based method, instead of spreading the energy to the whole spectrum as in the spontaneous Raman imaging, the exemplary narrow-bond SRS can focus its energy to the vibrational transition of a specific bond. The exemplary SRS signal can provide linear concentration dependence to the analyte without non-specific background. Compared to a previously known nonlinear vibrational imaging procedure such CARS microscopy, which can suffer from spectral distortion, unwanted non-resonant background, non-straightforward concentration dependence and coherent image artifact, the exemplary SRS can exhibit straightforward image interpretation and quantification without complications from non-resonant background and phase-matching conditions. Besides the above-mentioned advantages, SRS can also have its own distinctive characters as an imaging procedure. For example, SRS can be immune to fluorescence background as compared to spontaneous Raman microscopy that can suffer from large fluorescence background. In addition, SRS, as a nonlinear process, can offer intrinsic 3D sectioning capability. Moreover, by adopting near-infrared excitation, SRS can offer deeper penetration depth and less phototoxicity, which can be well suited for imaging live cells, tissues and animals. Recently, narrow-band SRS has achieved unprecedented sensitivity down to approximately 1000 retinoic acid molecules and up to video rate imaging speed in vivo.

All of the above applications can show the universal and distinct advantage of the exemplary SRS to image lipids, proteins and genetic material in live cells, tissues, organisms and animals with minimum perturbation and high specificity and sensitivity, extending the repertoire of reporters for biological imaging beyond fluorophores.

To that end, an exemplary system, method and computer-accessible medium for using heavy water (i.e., $D_2O$) as a probe for imaging metabolic activities, both in vivo and in vitro, can be provided.

Exemplary Incorporation of $D_2O$ into Cells

When heavy water is administered to cells (whether in vivo or in vitro), it can be incorporated into lipids, proteins, and/or genetic material produced by the cells during their normal life cycle. In various embodiments described herein, heavy water can be administered either to cells, ex vivo and/or in vitro, or administered in vivo to an organism, such as a human or other animal.

In order to monitor the levels of lipids, proteins and/or genetic material, such as DNA or RNA over time, it can be beneficial to have a baseline measurement of the lipids, proteins and/or genetic material in the cells, tissue, organ, or organism being monitored. To obtain a baseline value, an effective amount of heavy water can be administered to the cells, tissue, organ, or organism, for a sufficient amount of time to facilitate incorporation of deuterium into the lipids, proteins, and/or genetic material produced during the normal lifecycle of the cell, tissue, organ, or organism. Those of skill in the art understand the lifecycle of the cell, tissue, organ, and/or organisms they can be monitoring, so understand how much time can be utilized, after administration of heavy water has begun, to establish a baseline measurement.

By way of example, adding between about 2% and 100% (v/v) heavy water into the water consumed by the cells, tissue, organ, or organism, for a time ranging from between about 20 min and 192 hours can typically be suitable to establish baseline levels of lipid, protein and/or genetic material.

The new proteins, lipids, DNA, and other macromolecules which incorporate heavy water-derived deuterium can have their own unique Raman spectrum, and the Raman spectrum can be detected and clustered in order to generate a "map" of newly synthesized macromolecules.

When subjected to Raman spectroscopic procedures, such as SRS and using appropriate mathematical formulas, as disclosed herein, it can be possible to produce spectra where peaks associated with lipids, proteins, and genetic material can be separated. The relative volume in each peak (e.g., measured by calculating the area under the curve) can be determined.

In some aspects, lipid molecules can be separated into different subtypes of lipids, such as saturated and unsaturated lipids, or further identify the exact type of lipids, for example, cholesterol and phospholipids.

Exemplary Procedure for Detecting Lipids, Proteins and/or Genetic Material

In one exemplary embodiment of the present disclosure, a computer-implemented procedure can be used, in some aspects, with software and/or computer programs, for clustering out various macromolecules (e.g., lipids, proteins, and/or genetic material) in living organisms, including virus, bacteria, nematodes, fungus, yeast, plants, animals, and human beings, including whole organisms, and isolated cells/tissue derived from these organisms.

Three-component un-mixing of $CH_L/CH_P/CH_{DNA}$ signals were previously reported. (See, e.g., Reference 24). SRS signals can be acquired from cells, tissue, organs, or organisms in the regions of 2135 $cm^{-1}$, 2185 $cm^{-1}$, and 2210 $cm^{-1}$, which regions bear the intrinsic features of lipids, proteins, and DNA, respectively.

A linear combination of the three signals can be used with coefficients to determine the relative amounts of the three macromolecules. The signals at 2135 $cm^{-1}$ ($I_{2135}$), 2185 $cm^{-1}$ ($I_{2185}$), and 2210 $cm^{-1}$ ($I_{2210}$) can be a linear combination of lipid, protein, and DNA concentrations ($CD_L$, $CD_P$, and $CD_{DNA}$) with coefficients $a_L$, $a_P$, $a_{DNA}$, $b_L$, $b_P$, $b_{DNA}$, $c_L$, $c_P$, and $C_{DNA}$ as shown, for example, in Eq. 1.

$$\begin{pmatrix} I_{2135} \\ I_{2185} \\ I_{2210} \end{pmatrix} = \begin{pmatrix} a_L & a_P & a_{DNA} \\ b_L & b_P & b_{DNA} \\ c_L & c_P & c_{DNA} \end{pmatrix} \begin{pmatrix} CD_L \\ CD_P \\ CD_{DNA} \end{pmatrix} \quad (1)$$

Un-mixing coefficients can be obtained from the spectra of D-labeled cellular extracts from $D_2O$-treated HeLa cells. (See e.g., graph shown in FIG. 11A). $a_L$, $b_P$, and $c_{DNA}$ can be set to 1, and the rest coefficients can be scaled to their relative values. The coefficients can be substituted with their values, Eq. 2, for example, as the following.

$$\begin{pmatrix} I_{2135} \\ I_{2185} \\ I_{2210} \end{pmatrix} = \begin{pmatrix} 1 & 0.38 & 0.29 \\ 0.48 & 1 & 1.08 \\ 0.24 & 0.71 & 1 \end{pmatrix} \begin{pmatrix} CD_L \\ CD_P \\ CD_{DNA} \end{pmatrix} \quad (2)$$

From Eq. 2, $CD_L$, $CD_P$, and $C_{DNA}$ can be derived as the unmixed D-labeled lipid, protein, and DNA signal intensity, respectively, using, for example, Eq. 3.

$$\begin{pmatrix} CD_L \\ CD_P \\ CD_{DNA} \end{pmatrix} = \begin{pmatrix} 1.31 & -0.98 & 0.67 \\ -1.24 & 5.21 & -5.27 \\ 0.56 & -3.47 & 4.58 \end{pmatrix} \begin{pmatrix} I_{2135} \\ I_{2185} \\ I_{2210} \end{pmatrix} \quad (3)$$

The unmixed CDDNA signal can be very weak in non-dividing cells. When monitoring non-dividing cells, or in other conditions when sufficient information can be obtained by evaluating only lipid and protein signals, a relatively simplified un-mixing procedure can be used which can focus primarily on separating $CD_L$ and $CD_P$ signals. The three-component un-mixing equation can thus be simplified, and the $CD_{DNA}$ variable removed to obtain Eqs. 4 and 5, from which the unmixed D-labeled lipid and protein signals can be derived using Eqs. 6 and 7. Thus, for example:

$$I_{2135} = a_L \cdot CD_L + a_P \cdot CD_P \quad (4)$$

$$I_{2185} = b_L \cdot CD_L + b_P \cdot CD_P \quad (5)$$

$$CD_L = \frac{a_P \cdot I_{2185} - b_P \cdot I_{2135}}{a_P \cdot b_L - a_L \cdot b_P} \quad (6)$$

-continued $$CD_P = \frac{b_L \cdot I_{2135} - a_L \cdot I_{2185}}{a_P \cdot b_L - a_L \cdot b_P} \quad (7)$$

For $CD_L/CD_P$ un-mixing, the spectra of in situ CD lipid and protein signals can be used to measure the coefficients. From the spontaneous Raman spectra of pure D-labeled protein signal (e.g., signals after a methanol wash, such as a 24-hour methanol wash) and pure D-labeled lipid signal (e.g., signals removed by methanol wash—subtracting methanol-resistant signal from total signal).

All signals can first be normalized to the phenylalanine peak at 1004 cm$^{-1}$, which stays constant during a methanol wash, and then normalized to the peaks of pure protein and lipid signals, respectively. (See e.g., FIGS. 11A-11F).

Thus, $a_L$ and $b_P$ were set to 1; the relative intensity of protein bleed-through signal in the lipid channel ($a_P$) and the relative intensity of lipid bleed-through signal in the protein channel ($b_L$) can be measured on the spectra. For example, in xenograft tumor tissues (see e.g., graph shown in FIG. 11C), $a_L=1$, $a_P=0.40$, $b_L=0.51$, and $b_P=1$.

Using this information, the following exemplary un-mixing equations (Eqs. 8 and 9) can be used for tumor tissues.

$$CD_L = 1.25 \cdot I_{2135} - 0.50 \cdot I_{2185} \quad (8)$$

$$CD_P = 1.25 \cdot I_{2185} - 0.64 \cdot I_{2135} \quad (9)$$

Using the same method, pure D-labeled protein and lipid signals can be obtained from the mouse pancreas and brain tissues and calculated their specific un-mixing coefficients. Data from the three types of tissues were combined to generate a set of average coefficients: $a_L=1$, $a_P=0.48\pm0.17$, $b_L=0.42\pm0.07$, and $b_P=1$.

The CD lipid spectrum shows a consistent shape, but CD protein can have varying levels of bleed-through into $CD_L$ channel across different tissue types. (See e.g. images shown in FIG. 13C). Additionally, it can be possible that this results from tissue-specific incorporation of deuterium into various non-essential amino acids ("NEAAs") and/or different NEAA composition of D-labeled proteins.

One representative example can be the pyramidal neurons: their cell body shows almost no SRS signal at about 2135 cm$^{-1}$, but shows a strong signal at 2185 cm$^{-1}$, suggesting almost no protein bleed-through into $CD_L$ channel. Thus, when applying the un-mixing procedure to cells and tissues previously uncharacterized, $a_P$ can be tested from 0.31-0.65 until the nucleus can be deprived of $CD_L$ signal after un-mixing.

The following equations can be used for $CD_L/CD_P$ signal un-mixing of different tissues.

|  | $CD_L$ un-mixing | $CD_P$ un-mixing |
| --- | --- | --- |
| Cos-7 and HeLa cells | $CD_L = 1.25 \cdot I_{2135} - 0.39 \cdot I_{2185}$ | $CD_P = 1.25 \cdot I_{2185} - 0.52 \cdot I_{2135}$ |
| Glioblastoma and Colon tumor xenograft | $CD_L = 1.25 \cdot I_{2135} - 0.50 \cdot I_{2185}$ | $CD_P = 1.25 \cdot I_{2185} - 0.64 \cdot I_{2135}$ |
| Zebrafish tissues | $CD_L = 1.25 \cdot I_{2135} - 0.50 \cdot I_{2185}$ | $CD_P = 1.25 \cdot I_{2185} - 0.52 \cdot I_{2135}$ |
| *C. elegans* | $CD_L = 1.25 \cdot I_{2135} - 0.70 \cdot I_{2185}$ | $CD_P = 1.25 \cdot I_{2185} - 0.52 \cdot I_{2135}$ |
| Mouse sebaceous glands and adipose tissues | $CD_L = 1.25 \cdot I_{2135} - 0.39 \cdot I_{2185}$ | $CD_P = 1.25 \cdot I_{2185} - 0.81 \cdot I_{2135}$ |
| Mouse internal capsule and cortex | $CD_L = 1.25 \cdot I_{2135} - 0.39 \cdot I_{2185}$ | $CD_P = 1.25 \cdot I_{2185} - 0.70 \cdot I_{2135}$ |
| Mouse liver, pancreas, and muscle tissues | $CD_L = 1.25 \cdot I_{2135} - 0.35 \cdot I_{2185}$ | $CD_P = 1.25 \cdot I_{2185} - 0.60 \cdot I_{2135}$ |

To unmix $CH_L$ lipids and $CH_P$ protein signals, a previously reported spectral linear combination procedure can be adapted. (See, e.g., Reference 22). The SRS signals can be acquired at 2845 cm$^{-1}$ and 2940 cm$^{-1}$, which bear the vibrational features of C—H bonds in lipids and proteins, respectively.

The amount of lipids and proteins can then be determined by a linear combination of the signals at those two wavenumbers, with coefficients predetermined by pure substances. (See, e.g., Reference 22). Eqs. 10 and 11 can be used to calculate unmixed $CH_L$ and $CH_P$ signals. $I_{2845}$ and $I_{2940}$ can be SRS signal intensities at 2845 cm$^{-1}$ and 2940 cm$^{-1}$, respectively. Thus, for example:

$$CH_L = I_{2940} - I_{2845} \quad (10)$$

$$CH_P = 5 \cdot I_{2845} - 0.4 \cdot I_{2940} \quad (11)$$

Suitable scanning software, such as Olympus FluoView 4.1, can be used to acquire images to assign color, calculate ratiometric values, and overlay images. SRS image can be generated by subtracting non-resonance background from the resonance signal.

In one embodiment, where sebaceous glands in living mice can be imaged in vivo, (see e.g., images shown in FIG. 1D), the two-photon absorption by blood cells can be independent of the resonance state, and the fast dynamics of the signal in the blood flow distinguishes it from the more static SRS signal.

$CD_L/CH_L$ and $CD_P/CH_P$ ratios can be used to show the proportion of newly synthesized lipids and proteins to total macromolecules, as an indication of relative metabolic rate. For example, $CD_L/CH_L$ ratio can be calculated using Eq. 12.

$$\frac{CD_L}{CH_L} = \frac{a*[C-D]}{b*[C-H]} = \frac{a*[\text{new lipid}]*G}{b*\left(\begin{array}{c}[\text{new lipid}]* \\ (1-G) + [\text{old lipid}]\end{array}\right)} \quad (12)$$

[C-D] and [C—H] can be the concentration of D-labeled and H-labeled lipids, respectively; a and b can be convening factors from lipid concentrations to SRS signals intensity; [old lipid] can be the amount of lipids that pre-existed before $D_2O$ probing and remained at the time of imaging (e.g., not being degraded); [new lipid] can be the amount of newly synthesized lipids and G can be the proportion of D-labeled lipids to the newly synthesized lipids.

By defining [total lipid] as the amount of total lipid after the probing period and at the time of imaging, [total lipid]= [new lipid]+[old lipid]. Then Eq. 10 can be rewritten as Eq. 13. Thus, for example:

$$\frac{CD_L}{CH_L} = \frac{a}{b} \cdot \frac{G}{\frac{[\text{total lipid}]}{[\text{new lipid}]} - G} \quad (13)$$

Since the upper limit of G can be approximately 0.2 ($D_2O$ enrichment) in all the exemplary experiments described herein, much smaller than [total lipid]/[new lipid], the $CD_L/CH_L$ can be approximated using Eq. 14. Thus, for example:

$$\frac{CD_L}{CH_L} = \frac{a}{b} \cdot G \cdot \frac{[\text{new lipid}]}{[\text{total lipid}]} \quad (14)$$

Thus, $CD_L/CH_L$ can be linear to the proportion of the amount of newly synthesized lipids to total lipids and therefore a ratiometric measurement of lipid synthesis rate.

Using the equations discussed above, in one aspect, spectra of cells, tissue, organs, or organisms, can be utilized in order to calculate the relative amounts of proteins, lipids and genetic material. In another aspect, for example, where cells may not be rapidly dividing, the relative amounts of proteins and lipids can be calculated.

The equations described herein can be used in a procedure, where data from the spectra can be obtained, calculations can be performed, and signals can be unmixed to provide information on the relative amounts of protein, lipid, and genetic materials in a sample.

Exemplary procedures for un-mixing newly synthesized C-D protein, C-D lipids and C-D DNA can be used in computer programs (software)—which can be executed on a computer or another processor, and stored on a hard drive, floppy drive, memory stick, RAM, ROM or any other computer-accessible storage medium—to determine and quantify metabolism in live cells, plants, microbes, animals, and humans.

The data can then be stored, for example, in a computer database. By storing baseline values, as well as additional values taken over time, the relative levels of protein, lipid and genetic materials can be monitored, or, in one aspect, the relative levels of protein and lipid, over time.

Exemplary In Vivo Versus In Vitro Assays

In some embodiments, assays can be performed in vivo on a living animal, such as a human. In some aspects of these embodiments, it can be desirable to follow the growth of a tumor, to follow the levels of amyloid plaque formation in a brain, to monitor the thickening of a lumen, for example, to evaluate the risk of stroke or atherosclerosis, to monitor the body fluids on body such as blood, plasma for metabolic diseases progression, for example, to evaluate the risk of diabetes, gout, and dyslipidemia to monitor the lipids and protein on the retina tissue and blood vessel for neurodegenerative diseases such as Alzheimer's disease. In some aspects of these embodiments, an animal, such as a human, can be monitored without administering therapy, merely to follow the progression of the disease. In other aspect of these embodiments, an animal, such as a human, can be monitored while administering therapy, to follow the progression of the disease, and determine whether the therapy is or is not working adequately.

In other embodiments, rather than being performed in vivo on tissues or organs within a living organism, the method involves the in vitro evaluation of one or more body fluids to detect metabolic changes in the body of the human or animal from which the body fluids can be derived. Representative body fluids include, but are not limited to, amniotic fluid, aqueous humor, vitreous humor, bile, blood, blood plasma, blood scrum, cerebrospinal fluid, cerumen (e.g., earwax), chyle, chyme, endolymph, perilymph, exudates, feces, female ejaculate, gastric acid, gastric juice, lymph, mucus (e.g., including nasal drainage and phlegm), pericardial fluid, peritoneal fluid, pleural fluid, pus, rectal discharge, rheum, saliva, sebum (e.g., skin oil), serous fluid, semen, serum, smegma, sputum, synovial fluid, sweat, tears, urine, vaginal secretions, vaginal discharge, vomit, and exosomes contained in one or more of these fluids. Drugs can be screened for their efficacy and/or toxicity by measuring metabolic changes in a patient to whom the drug can be administered, where the metabolic changes involve changes in the relatively amounts of lipids, proteins, and/or genetic materials present in samples of one or more of these body fluids, before and after the drug can be administered.

In one aspect, a first sample of a body fluid can be taken from a patient, and evaluated to create a baseline value. A drug can then be administered to the patient, and after waiting until the drug can be expected to exert a physiological effect, a second sample of a body fluid can be obtained from the patient. The sample can be evaluated to create a second value, and the second value can be compared to the baseline value. Changes in the concentration of lipids, proteins and/or genetic material from the baseline values can be presumed to relate to the administration of the drug.

Biological assays using the in vivo and in vitro methods described above are discussed in more detail below.

Exemplary Use of Information on the Relative Level of Protein, Lipid and/or Genetic Material in Biological Assay When organisms, or cells/tissue derived from the organisms, can be first administered heavy water, so as to produce lipids, proteins, and/or genetic material which incorporate deuterium, baseline measurement of the amounts of lipids, proteins, and/or genetic material can be determined.

Accordingly, in still other exemplary embodiments of the present disclosure, the measurements of the relative levels of lipid, protein and/or genetic material can be obtained using SRS microscopy.

One or more of these exemplary aspects can be applied for drug screening. For various diseases, the drug treatment can alter the metabolic activities of cells and tissues. The heavy water labeling with vibrational imaging and spectroscopy can tell the metabolic activities of newly synthesized deuterium-labeled lipids, protein, DNA and/or carbohydrates. For carbohydrates measurement on animals and human beings, one organ is the liver, since the liver is the place where glycogen, a carbohydrate polymer, is synthesized. In one exemplary embodiment, newly synthesized carbohydrates can be extracted, and the Raman peak can be measured on purified glycogen. The liver synthesizes glycogens in a relatively short period of time after fasting, while lipids, protein and genetic materials typically take longer to form. Accordingly, glycogen can be measured directly without using any procedures for separation. For example, in mice, the fasting time can be about 18 hours, at which time heavy water and food can be provided for about 8 hours, at which time the newly formed liver glycogen can be measured at a Raman peak of around 2160 $cm^{-1}$. Carbohydrate measurements can be used in both in vitro cell culture and in vivo experiments on animals, even human beings, cells or tissue derived from the animals or human beings, or biological fluids derived from the animals or human beings.

Whether the evaluation can be performed in vivo, or in vitro, by taking samples of one or more biological fluids after administration of heavy water to the patient, and both before and after exposure to a putative chemotherapeutic agent or combination of agents, a baseline determination of the levels of protein, lipid, and/or genetic material can be made.

Following exposure of the organisms, or cells/tissue derived from the organisms, to one or more compounds (e.g., while continuing to administer heavy water), a second measurement can be taken to determine whether the relative amounts of lipids, proteins and/or genetic material have changed relative to the baseline amounts. Differences in the amount of lipids, proteins, and/or genetic material can be used in a variety of diagnostic and/or theranostic methods.

In some exemplary embodiments, additional measurements can be measured over time, for example, after repeated exposure, as might be the case when a patient is treated for a disease using one or more compounds. In other exemplary embodiments, rising dosage studies can be performed to determine, for example, an optimal range of drug concentrations to bring about a desired therapeutic effect, while avoiding toxicity.

According to certain additional exemplary embodiments of the present disclosure, the information on differences in the relative amounts of lipids, proteins, and/or genetic material before and after administration of the one or more compounds can be used to determine whether a particular therapeutic regimen can be effective in treating an individual patient, and/or whether a putative drug candidate has efficacy and/or toxicity.

Exemplary Determining the Efficacy of a Therapeutic Regimen

In some exemplary embodiments of the present disclosure, the effectiveness of a putative treatment for a given disease can be determined. Representative diseases include cancer, heart disease, stroke, neurodegenerative diseases such as Alzheimer's disease and Parkinson's disease, neurotropic viral infections, paraneoplastic disorders, traumatic brain injury and multiple sclerosis, and infections by viruses, bacteria, fungi, prions or nematodes, endocrinology and metabolic diseases such as diabetes and diabetic complications, gout, type 1 & type 2 diabetes, obesity, metabolic syndrome, growth disorders, dyslipidemia hypogonadism, rare metabolic diseases.

Exemplary Determination of Effective Anti-Cancer Treatments

In another exemplary aspect, when used in cancer diagnostics, whether a given therapy can be effective against a tumor can be evaluated by administering heavy water to a patient, facilitating time for deuterium in the heavy water to become incorporated in lipids, proteins, and/or genetic material in the tumor, and taking a baseline Raman spectra of the tumor. The determination of an effective anti-cancer treatment can be performed in vitro, in vivo, or a combination of both approaches.

When a particular therapy can be successful, the cancer cells die. There can be several potential mechanisms by which cancer therapies work, and many of these function by inhibiting various biological pathways that a cancer cell needs to survive. Inhibition of these pathways results in changes in the relative levels of one or more of protein levels, lipid levels, and/or levels of genetic material. Thus, by evaluating the relative levels of protein, lipid and/or genetic material in the tumor over time, the course of a putative therapy can be followed, and a determination can be made as to whether it can be effective in treating a patient's particular type of cancer.

Using the exemplary methods and systems described herein, drugs can be evaluated for their ability to inhibit tumor growth. Using heavy water and vibrational imaging and spectroscopy, the metabolic changes of tumor cells can be detected before and after the treatment and find out which drug can be the most effective one for inhibiting tumor growth. The determination of an effective anti-cancer treatment can be performed in vitro, in vivo, or a combination of both approaches.

This exemplary method and system can also be applied for detecting and diagnosing various types of cancers and separate subtypes of a certain cancer, based on its capability of detecting the metabolism differences between various cancer and normal cells and tissues.

In some aspects, the exemplary method and system can also be applied for tumor detection, tumor boundary detection, degree of tumor aggressiveness, tumor progression, and intra-tumor metabolic heterogeneity study.

Representative types of cancer that can be evaluated using the methods described herein include skin cancer, breast cancer, mouth cancer, throat cancer, bladder cancer, bone cancer, brain tumors, bronchial tumors, burkitty lymphoma, prostate cancer, rectal cancer, lung cancer, ovarian cancer, pancreatic cancer, stomach cancer, esophagus cancer, and cervix cancer.

Using in vitro methods, biological fluids, such as blood, plasma, and the like, can be evaluated for cancers such as blood-related cancers, including leukemia and cancers associated with the lymph, such as lymphoma.

Leukemia is a term used to define a group of cancers that usually begin in the bone marrow and result in high numbers of abnormal white blood cells. These white blood cells may not be fully developed and can be called blasts or leukemia cells. Diagnosis is typically made using blood tests or bone marrow biopsy. There can be four main types of leukemia, including acute lymphoblastic leukemia ("ALL"), acute myeloid leukemia ("AML"), chronic lymphocytic leukemia ("CLL") and chronic myeloid leukemia ("CML"). Leukemias and lymphomas both belong to a broader group of tumors that affect the blood, bone marrow, and lymphoid system, known as tumors of the hematopoictic and lymphoid tissues. Serum cholesterol, HDL & LDL cholesterol can be inversely associated with incidence of leukemias, whereas triglycerides can be significantly elevated in leukemia patients. The inverse association between cancer and serum cholesterol can reflect a physiological response to early-undiagnosed stages of cancer.

Lymphoma is a cancer that begins in infection-fighting cells of the immune system, called lymphocytes, which cells can be in the lymph nodes, spleen, thymus, bone marrow, and other parts of the body. There can be two main types of lymphoma, non-Hodgkin lymphoma, and Hodgkin lymphoma. Lymphatic fluid can be evaluated for the presence of lymphocytes. Many studies suggest a role for cholesterol in lymphoma development. Serum cholesterol levels have been observed to be low in newly diagnosed lymphoma cases. Lymphoma cases can have statistically significantly lower estimated total serum cholesterol, high-density lipoprotein, and low-density lipoprotein levels than controls in the years prior to diagnosis/index date (reference: Alford et al Serum cholesterol trajectories in the ten years prior to lymphoma diagnosis, Cancer Causes Control. 2018 January; 29(1): 143-156). So after the heavy water labeling, newly formed subtypes of C-D labeled lipids can be detected by SRS hyper-spectral imaging combined with clustering procedures.

In some aspects of this exemplary embodiment, genetic information about the type of cancer can be obtained first, to identify potential therapeutic regimens for the patient's particular type of cancer.

For example, in the case of breast cancer, there can be many types of breast cancer. The most common types can be ductal carcinoma in situ, invasive ductal carcinoma, and invasive lobular carcinoma.

The type of breast cancer can be determined by the specific cells in the breast that can be affected. Most breast cancers can be carcinomas, such as adenocarcinomas, and these that start in the epithelial cells that line organs and tissues throughout the body. Less common types of breast cancers include sarcomas, phyllodes, Paget disease, and angiosarcomas. Occasionally, a single breast tumor can include a combination of different types.

Breast cancer also has many subtypes such as luminal A breast cancer (e.g., estrogen-receptor and/or progesterone-receptor positive, HER2 negative), luminal B breast cancer (e.g., estrogen-receptor and/or progesterone-receptor positive, either HER2 positive or HER2 negative with high levels of Ki-67, generally grow slightly faster than luminal A), and triple negative breast cancer (all estrogen-receptor, progesterone receptor, and HER2 can be negative), etc.

In one exemplary aspect of the exemplary embodiments of the present disclosure, putative therapeutic regimens can be determined based on the initial genetic information, and cancer cells can be cultured (e.g., with heavy water being part of the cell culture medium) while a chemotherapy is being administered. By following the levels of protein, lipid, and/or genetic material over time, a determination can be made as to whether the therapy is successful. Using a high-throughput screening approach, the cells can be subjected, in parallel, to a number of putative chemotherapeutic approaches. Once a successful therapy has been determined, for example, as a result of changes in one or more of the levels of protein, lipid, and genetic material, the patient can be administered the therapy most likely to result in effective treatment.

In another exemplary aspect of the exemplary embodiments of the present disclosure, putative therapeutic regimens can be determined without first evaluating the genetic information on the type(s) of cancer, and, rather, a series of putative treatments can be evaluated, and the selection of an appropriate therapeutic regimen can be determined based on the actual efficacy observed in culture.

According to another exemplary embodiment of the present disclosure, such exemplary evaluation can be performed in vitro, where cancer cells, for example, cells taken from a biopsy, can be cultured, and subjected to putative anti-cancer treatments. The anti-cancer treatments can be evaluated one at a time, or in parallel, and when evaluated in parallel, can be evaluated in a high throughput manner.

Instill another exemplary embodiment of the present disclosure, such exemplary evaluation can be performed in vivo, where it can be possible to also use the spectroscopic method to determine the size of the tumor, and note whether the tumor is growing, shrinking, or staying approximately the same size, throughout the duration of the chemotherapy.

According to a further exemplary embodiment of the present disclosure, the method and system can be used to detect differences in metabolism between cancer and normal healthy cells and tissues. In another exemplary aspect, a patient has more than one type of breast cancer cell types, where the metabolic activities of the different types of cancer can also be different, and the effectiveness of therapy against each of these breast cancer cell types can be determined.

In some exemplary embodiments, physicians can select appropriate treatment methods based on detecting a subtype of breast cancer, or other cancers. Applying the heavy water labeling and vibrational imaging of the cancer patient's tissue sample, it can be possible to determine which subtypes of cancer can be present. This can assist a physician to perform a proper diagnosis, and determine which treatment method to administer.

Following the treatment with a putative chemotherapeutic agent, or combination of agents, a further spectrum can be obtained, which can be used to determine whether the relative amounts of one or more of the lipid, protein and/or genetic material have changed. Changes in these relative amounts of one of more of the lipid, protein, and/or genetic material can be indicative that the chemotherapeutic method is working. Repeated additional spectra can be obtained over the course of the treatment.

Exemplary Determining the Efficacy of Therapy for Alzheimer's Disease

Amyloid beta (Aβ or Abeta) denotes peptides of 36-43 amino acids that can be involved in Alzheimer's disease as the main component of the amyloid plaques found in the brains of Alzheimer patients. The peptides can be derived from the amyloid precursor protein (APP), which can be cleaved by beta secretase and gamma secretase to yield Aβ. Aβ molecules can aggregate to form flexible soluble oligomers which can exist in several forms. It is now believed that certain misfolded oligomers (e.g., known as "seeds")

can induce other Aβ molecules to also take the misfolded oligomeric form, leading to a chain reaction akin to a prion infection. The oligomers can be toxic to nerve cells. The other protein implicated in Alzheimer's disease, tau protein, also forms such prion-like misfolded oligomers, and misfolded Aβ can induce tau to misfold.

In one exemplary aspect, an exemplary method and system for determining the efficacy of a putative therapy for Alzheimer's disease can involve administering an effective amount of $D_2O$ to a patient, which patient has Alzheimer's disease, where the patient's brain can be visualized using SRS Raman imaging procedures, and facilitating a sufficient amount of time for the $D_2O$ to become incorporated into the patient's brain tissue. Then, a first Raman spectrum, such as an SRS Raman spectrum of the brain can be obtained, where signals can be acquired, at least, from 2135 $cm^{-1}$, 2185 $cm^{-1}$, and 2210 $cm^{-1}$, which signals correspond to lipids, proteins, and DNA, respectively.

The signals can be un-mixed so as to form separate spectral peaks for the lipids, proteins, and DNA in the brain tissue, and baseline values for the relative amounts of lipids, proteins, and DNA can be measured.

Then, a putative therapy for treating Alzheimer's disease can be administered to the patient for a suitable time such that, if the therapy can be effective, changes in the lipid, protein and/or DNA levels in the brain can be expected to vary from their levels before therapy can be administered.

An effective amount of $D_2O$ can be continuously administered to the patient while the patient is treated with the therapy, so as to facilitate deuterium to become incorporated into one or more of the lipid, protein, and DNA found in the brain tissue. After a suitable time period, a second Raman spectrum, such as an SRS Raman spectrum, of the brain tissue can be obtained, where signals can be acquired, at least, from 2135 $cm^{-1}$, 2185 $cm^{-1}$, and 2210 $cm^{-1}$, which signals correspond to lipids, proteins, and DNA, respectively.

The first and second Raman spectra can be compared. Where significant changes in the amount of lipid, protein and/or DNA can be observed, this can be indicative of the success of the therapy. Insignificant changes in the amount of lipid, protein, and/or DNA can be indicative of the lack of success of the therapy in improving the patient's condition, although it can also be indicative that the patient's Alzheimer's disease is not progressing, which can ordinarily occur in the absence of therapy. However, if peaks associated with beta-amyloid protein increase, this can be indicative that the patient's condition is worsening. For this reason, in one aspect of this embodiment, the method particularly looks for changes in the relative amounts of beta-amyloid plaque in the patient's brain.

Exemplary Determining the Efficacy of Therapy for Metabolic Diseases

Metabolic syndrome is a cluster of conditions, increased blood pressure, high blood sugar, excess body fat around the waist, and abnormal cholesterol or triglyceride levels. One or more of these conditions can increase a patient's risk of heart disease, stroke, diabetes, obesity, and other disorders.

Beneficial fats (lipids) found in the blood include cholesterol and triglycerides. Cholesterol is an essential component of cell membranes, of brain and nerve cells, and of bile, which helps the body absorb fats and fat-soluble vitamins. The body uses cholesterol to make vitamin D and various hormones, such as estrogen, testosterone, and cortisol.

Triglycerides, which can be contained in fat cells, can be broken down, then used to provide energy for the body's metabolic processes, including growth. Triglycerides can be produced in the intestine and liver from smaller fats called fatty acids.

Fats, such as cholesterol and triglycerides, cannot circulate freely in the blood, because blood is mostly water. To be able to circulate in blood, cholesterol and triglycerides can be packaged with proteins and other substances to form particles called lipoproteins. There can be different types of lipoproteins. Each type has a different purpose and is broken down and excreted in a slightly different way. Lipoproteins include chylomicrons, very low density lipoproteins ("VLDL"), low-density lipoproteins ("LDL"), and high-density lipoproteins ("HDL"). Cholesterol transported by LDL is called LDL cholesterol, and cholesterol transported by HDL is called HDL cholesterol.

There can be several complications associated with abnormal lipid levels, atherosclerosis. Generally, a high total cholesterol level (e.g., which includes LDL, HDL, and VLDL cholesterol), particularly a high level of LDL (e.g., the "bad") cholesterol, increases the risk of atherosclerosis and thus the risk of heart attack or stroke. However, not all types of cholesterol increase this risk. A high level of HDL (e.g., the "good") cholesterol can decrease risk, and conversely, a low level of HDL cholesterol can increase risk.

Very high levels of triglycerides (e.g., higher than 500 milligrams per deciliter of blood, or mg/dL) can increase the risk of pancreatitis.

Traditional methods for measuring lipid levels involve taking a "fasting lipid profile," wherein the levels of total cholesterol, triglycerides, LDL cholesterol, and HDL cholesterol measured after a person fasts for 12 hours. Levels of cholesterol and triglycerides typically vary considerably from day to day. For example, cholesterol levels can vary by about 10%, and triglyceride levels can vary by up to 25%. However, trends can be observed by monitoring the relative levels over time.

When lipid levels can be high, this is referred to as dyslipidemia, and when they can be too low, this is referred to as hypolipidemia, and hyperlipidemia is an example of a metabolic disease.

Consuming high-fat food, inherited disorder, medical conditions like hypothyroidism, diabetes, kidney disease, alcoholism, stress, and liver disease can be a few of the reasons behind increasing the lipid levels in the blood. Certain medicines, such as blood pressure medicines, steroids, and birth control pills can also increase lipid levels.

There can be a variety of treatments available for the various disorders associated with metabolic diseases. These include medications to control blood sugar levels, medications to treat liver diseases, medications to lower cholesterol levels, and changes in diet and exercise.

In one aspect of the exemplary embodiments described herein, the effectiveness of these treatments can be evaluated, for example, by measuring the levels of lipids, and, optionally, proteins and/or genetic material, in patients being treated for metabolic disorders. As the levels of lipids change, the relative success of a given therapy can be evaluated. For example, HDL and LDL have separate peaks in Raman spectroscopy, so an increase in HDL, and/or a decrease in LDL following administration of a putative therapy, relative to baseline values, can be indicative that a patient is being successfully treated.

In one aspect of the exemplary embodiments described herein, the effectiveness of these treatments can be evaluated. For example, in overweight patients or obesity patients, triglyceride-to-HDL-cholesterol ratio and metabolic syndrome can be contributors to cardiovascular risk.

Triglyceride to high-density lipoprotein cholesterol ratio (TG/HDL)> or =3.0 (in mg/dl) is a marker of insulin resistance in overweight persons. For instance, if a patient's total cholesterol is 180 and their HDL is 82, the cholesterol ratio is 2.2. According to the American Heart Association (AHA), patients can aim to keep their ratio below 5, with the ideal cholesterol ratio being 3.5.

Exemplary Determination of Effective Antimicrobial Treatments

In another exemplary embodiment of the present disclosure, biological samples containing a bacteria, fungi, virus, or nematode can be subjected to one or a plurality of putative treatment regimens, and, where the levels of lipids, proteins and/or genetic material after treatment can be substantially different than baseline, an effective treatment regimen can be identified, and, in some embodiments, administered to a patient. The determination can be performed stepwise, or in parallel, for example, using high-throughput screening methods.

In another exemplary embodiment of the present disclosure, for example, with respect to drug resistant microbial infections, it can be possible to follow various treatment regimens real-time, and determine whether they can be effective in treating the infections. This can provide an alternative, for example, to genetically screening a virus, such as HIV, HBV or HCV, present in a patient's blood or other biological fluid, to determining specific mutations associated with drug resistance, or to administering an antibiotic to a patient hoping it can be effective, only to find out the bacteria can be resistant to this particular antibiotic.

In one exemplary aspect of the exemplary embodiments of the present disclosure, high-throughput methods can be used to evaluate putative treatments for viral infections. Many viral infections, such as HIV, HBV, and HCV, result from viruses which can be resistant to one or more antiviral treatments, as a result of prior exposure of the virus to these treatments, which results in the development of resistance to the treatments. One way to determine whether a particular therapy can be efficacious in such patients can be to use genetic screening to determine the presence of genetic variations associated with mutations in the virus, which mutations can be associated with resistance to a particular treatment. This information, while useful, is not guaranteed to identify all mutations in all viruses present in the patient. For example, patients often have more than one type of HIV virus, as a result of repeated exposure, so a therapy that works to treat a major HIV variant may not treat a minor HIV variant.

Rather than relying solely on genetic information, patient samples can be obtained, and, in in vitro assays, in a high throughput manner, subject samples containing HIV to a variety of potential treatments. Whether or not the treatment is effective can be determined by taking baseline measurements, as well as further measurements over time, of the relative levels of protein, lipid and genetic material in cells exposed to HIV, and subsequently, to putative therapies for treating the HIV infection.

A determination can be made as to whether a therapy that can otherwise be effective, based on the detection of major HIV variants, also treats minor HIV variants that might not be detected using a genetic screen, by following the course of treatment over time. Thus, rather than subjecting a patient to a single course of therapy for an extended period of time, only to discover that the major variant was treated, but the minor variant was resistant to the treatment, a series of potential treatment regimens can be evaluated to determine a treatment regimen that can be most effective for a given patient.

Where the biological organism is a bacteria, one aspect of this method involves screening putative antibiotics to determine whether the bacteria has antibiotic tolerance/resistance to a particular antibiotic, and can be used to help a treating physician determine the most effective antibiotic, or combination of antibiotics, to treat a bacterial infection. A biological fluid comprising bacteria can be evaluated for putative anti-bacterial therapies, and, based on resistance to one or more of the therapies, and successful anti-bacterial efficacy in one or more therapies, a course of therapy can be decided.

This can be useful, for example, in the treatment of drug-resistant bacterial infections, where one or more treatments can be commonly used in an effort to treat the disorder, and when one treatment is ineffective, the infection can worsen until an effective treatment is discovered.

A biofilm is any group of microorganisms in which cells stick to each other, and these cells often adhere to a surface, which can be a biological surface, such as the inside of a patient's lungs. Lung infection is the main cause of morbidity and mortality in patients with cystic fibrosis and is mainly dominated by *Pseudomonas aeruginosa*. The biofilm mode of growth makes eradication of the infection extremely difficult, and it causes a chronic inflammation in the airways. In addition to the difficulty of treating biofilms with conventional antibiotic therapy, treating biofilms can also be hindered by the rising antibiotic resistance among pathogens. The methods described herein can be useful in studying the metabolic heterogeneity in biofilms, or other microbiota, for example, as a way to determine effective treatment methods.

According to a further exemplary embodiment of the present disclosure, a method can be used to determine what type of infection a patient has, for example, viral, bacterial, or fungal. For example, where it is clear that a patient has an infection, but it is unclear whether the infection has been caused by a virus, bacteria, or fungus, samples can be subjected to one or more anti-viral, anti-bacterial, and/or anti-fungal agents, and determine which can be successful in treating the infection. If an infection is susceptible to an anti-bacterial agent, then the infection is most likely a bacterial infection.

In one aspect of the exemplary embodiment of the present disclosure, a determination can be made as to whether a patient has viral or bacterial meningitis. Administration of an antibiotic to a patient with viral meningitis may not be expected to result in any significant change in relative amounts of lipid, protein, or genetic material in a biological sample, such as a sample of cerebrospinal fluid, in a patient. However, if the patient has bacterial meningitis, a significant change can be expected to be observed. In this manner, the method provides a rapid screening method to determine whether a patient has viral or bacterial meningitis, and facilitates timely and effective treatment to be administered.

Exemplary Determination of the Safety of a Therapeutic Agent

In other exemplary embodiments of the present disclosure, the safety of a compound can be determined. For example, it can be possible to expose a patient, such as, a human or non-human animal patient, cells/tissues obtained from a patient, a plant, or plant matter obtained from the plant, or a microbial organism, such as a bacteria, fungi, or virus, to heavy water for a sufficient time that heavy water can be incorporated into the lipids, protein, and/or genetic material.

It can then be possible to obtain an initial spectrum to obtain a baseline value of the relative amounts of lipids, proteins and/or genetic material, either in vivo or in vitro. Following administration of a compound of interest, a second spectrum can be obtained, and a second value of the relative amounts of lipids, proteins and/or genetic material, either in vivo or in vitro, can be obtained. There can be a correlation between the levels of lipids, proteins and/or genetic material and the toxicity of the compound to the patient, cells/tissue obtained from the patient, plant, plant matter, or microbial organisms.

Compounds which do not appear to adversely affect the relative amounts of lipids, proteins and/or genetic material can be deemed relatively non-toxic. In some aspects, the tests can be continued for a predetermined period of time while the compound is continuously administered, either at the same dose, or at different doses (for example, rising dosage studies). In other aspects, once an initial screen has identified compounds which appear to be non-toxic, and, optionally, other compounds which appear to be toxic, confirmatory toxicology studies can be performed on those compounds which appear to be non-toxic.

Toxicology studies can be performed, for example, in in vivo or in vitro models, plant models, animal models, and human studies, such as Phase I, II, and III clinical trials.

Where a patient is not suffering from a disease, and the interest in the evaluation is to determine drug toxicity, changes from baseline can indicate that the drug has some toxicity. Where the second sample has minimal changes from baseline, such can indicate that the drug is relatively non-toxic.

A formal toxicology study using other methods of determining drug toxicity can optionally then be performed on one or more drugs that appear to be relatively non-toxic based on this preliminary screen. This approach can be relatively beneficial when screening combinatorial libraries of compounds, as it can facilitate a quick identification of compounds which can be relatively non-toxic.

According to still other exemplary embodiments of the present disclosure, this approach can be combined with a binding assay, where the drug can be screened for its ability to bind, as a ligand, to a particular biological target, such as a receptor. If a compound is relatively non-toxic, but has poor binding to a desired biological target, or vice versa, a determination can be made as to whether the compound can be a good candidate to advance to further studies.

In another exemplary embodiment of the present disclosure, such approach can be combined with an assay to determine whether the compound has desired activity once bound to the receptor. For example, a compound can bind to a receptor and function as an agonist, a partial agonist, an inverse agonist, an antagonist, or an allosteric inhibitor. Using a combination of assays, it can be possible to identify compounds which have relatively low toxicity, bind to the proper receptors, and have the desired activity once bound to the receptors.

According to a still further exemplary embodiments of the present disclosure, it can also be to perform an additional assay to determine a compound's selectivity for a desired receptor over other less desired receptors. This combination of assays can determine relative toxicity of putative therapeutic compounds, the ability of the compounds to bind to desired receptors, the activity of the compounds once bound, and the selectivity of the compound for the desired receptor versus other receptors, such as those which can cause unwanted side effects.

Exemplary Evaluation of the Activity of Compounds Against Plana

In an exemplary embodiments of the present disclosure, photosynthesis can be evaluated by following the relative amounts of lipids, proteins, and/or genetic material in various plants and algae. For example, plants and/or algae can be exposed to heavy water for a sufficient amount of time for deuterium to be incorporated into plant or algal lipids, proteins, and/or genetic material. A baseline value of the relative amounts of lipids, proteins and/or genetic material in the plants and/or algae can be measured. Then, the plants and/or algae can be exposed to one or more conditions, such as exposure to different light sources and/or different light duration, and for plant growth regulators which either accelerate plant growth, or can be herbicidal in nature. Following exposure to these conditions, a second value of the relative amounts of lipids, proteins, and/or genetic material in the plants and/or algae can be measured. Differences in the levels of lipids, proteins, and/or genetic material before and after exposure to the one or more conditions can show, for example, whether plant or algal growth can be accelerated or diminished.

By separately visualizing the newly synthesized protein, lipids, and carbohydrates, the conditions for photosynthesis can be optimized. In one aspect of this embodiment, this information can be used to optimize production of algal oil, which can be used directly as a fuel, or converted to biodiesel fuel, an alternative to liquid fossil fuels, and/or to commonly known biofuel sources such as corn and sugarcane. In one exemplary embodiment of the present disclosure, the method can be performed in a high throughput manner, and can be used to study which compartment of an algae cell is producing lipids (oil), and under what conditions oil production can be optimized. In another exemplary embodiment of the present disclosure, in addition to or in place of SERS, photosynthesis can be studied using heavy water combined with vibrational imaging and spectroscopy.

It can also be possible to determine whether compounds can be effective plant growth regulators, for example, compounds which promote or inhibit plant growth. For example, whether a compound promotes or inhibits plant growth can be evaluated by monitoring the proteins and/or lipids content, and their turnover, in plant leaves. In exemplary embodiments of the present disclosure, the protein and/or lipids content can be monitored by administering heavy water to the plants, facilitating sufficient time for the plant leaves to incorporate $D_2O$ into proteins and/or lipids in the plant leaves, taking a first SRS Raman spectrum of the plant leaves to obtain baseline values for protein and/or lipid levels, administering to the plant a compound which can inhibit or promote plant growth, while continuously administering heavy water to the plant, and taking a second SRS Raman spectrum of the plant leaves to obtain subsequent values for protein and/or lipid levels. A negative change in the levels of proteins and/or lipids can be indicative that the plant growth is being inhibited, and a positive change in the levels of proteins and/or lipids can be indicative that the plant growth is being promoted.

Proteins can be a highly evolved and diverse class of molecules performing endless tasks and functions within plants. They can be beneficial in the biosynthses of enzymes, and membrane channels and pumps. The chlorophyll number molecules can be specifically arranged in and around pigment protein complexes called photosystems, which can be embedded in the thylakoid membranes of chloroplasts. If a plant is lacking of protein in its leaves, it can reduce numbers of chlorophyll, and, accordingly, growth slows down.

On the other hand, monitoring the protein to lipids ratio in certain plants can follow a constant to keep the healthy status. Lipids play a beneficial role as membrane components, during signaling, and for the movement of vesicles, lipids' function relates to plant development.

Exemplary Methods of Medical Imaging of Injury and Injury Recovery

In some exemplary embodiments of the present disclosure, the methods can be provided for imaging injuries, and a recovery from injuries.

While patients can be unlikely to know when they can be about to be injured, so a baseline value for protein, lipid, and/or genetic material at the site of the injury may not be available, a proxy for a baseline value can be obtained from the patient from another site that is not injured, where it is likely that the relative levels of protein, lipid and/or genetic material can be the same or similar to the injured site.

While a patient is recovering, the patient can be administered heavy water, the levels of protein, lipid and/or genetic material can be measured over time, and compared to the "proxy" baseline. As the levels of protein, lipid, and/or genetic material approach that of the baseline, the patient can be seen as recovering from the injury. When the levels of protein, lipid, and/or genetic material continue to diverge from that of the baseline, the patient can be seen as not successfully recovering from the injury.

Representative injuries that can be followed using the methods described herein include, but are not limited to, brain trauma, spinal cord injury, small vessel diseases, bone injury, traumatic brain injury, strokes, and brain tumor.

Exemplary Methods for Following Prenatal or Postnatal Development and Cell Lineages Representative postnatal developments that can be followed using the methods described herein include, but are not limited to, myelination. There is a time window for myelination in postnatal development, which is extremely hard to be detected by other procedures. Myelin is lipids enriched tissue, which can be detected background free by choosing C-D labeled lipids peak after heavy water labeling.

Representative cell lineage can be detected using the exemplary DO-SRS microscopy in conjunction with fluorescent microscopy can track the metabolic activity of specific cell lineages during development. For example, hemangioblast cells labeled by Tg(kdrl:EGFP) had the strongest CD protein signal, those cells originate from lateral plate mesoderm and give rise to endothelial and hematopoictic lineages. Their strong $CD_P$ signal indicates active protein biosynthesis, possibly due to fast proliferation, during the 0-24 hpf period.

Exemplary Methods for Detecting Metabolic Heterogeneity of Microbes or Other Living Organisms In yet another exemplary aspect of the present disclosure, exemplary methods or procedures can be used to detect metabolic heterogeneity of microbes or other living organisms, as well as for screening genes, for example, for detecting mutations.

Exemplary Methods for Detecting Myelin Formation

In yet another exemplary aspect of the present disclosure, the exemplary methods and systems can be used to detect changes in myelin, including myelin formation and destruction. This can be particularly relevant in connection with multiple sclerosis, and determining the effectiveness of a particular treatment.

Multiple sclerosis ("MS") is a demyelinating disease in which the insulating covers of nerve cells in the brain and spinal cord can be damaged. This disrupts the ability of parts of the nervous system to communicate, resulting in a range of signs and symptoms, including physical, mental, and sometimes psychiatric problems. MS takes several forms, with new symptoms either occurring in isolated attacks (relapsing forms) or building up over time (progressive forms). Patients can go into remission. Patients can also have permanent neurological problems, particularly as the disease advances.

While the cause is not clear, the underlying mechanism is believed to involve destruction by the immune system or failure of the myelin-producing cells.

There can be a variety of treatments for relapsing-remitting multiple sclerosis ("RRMS"), including interferon beta-1a, interferon beta-1b, glatiramer acetate, mitoxantrone, natalizumab, fingolimod, teriflunomide, dimethyl fumarate, alemtuzumab, and ocrelizumab. These treatments can be modestly effective at decreasing the number of attacks. Progressive multiple sclerosis has been treated with rituximab, ocrelizumab, and mitoxantrone. The goal of MS treatments can be to at least slow the progression of the disease, and decrease rates of relapses.

When evaluating a patient to determine the efficacy of a given treatment regimen, the patient can be administered heavy water, and, after deuterium has been incorporated into the patient's protein, lipid, and/or genetic material, a baseline value of these levels in brain tissue can be determined. Imaging of C-D protein and C-D lipids by heavy water labeling can detect changes in myelin formation and destruction.

Where myelin levels increase relative to baseline, this is indicative that a treatment is effective at treating MS. Where myelin levels stay relatively constant relative to baseline, this is indicative that a treatment is effective at slowing or stopping the progression of the disease. Where myelin levels can be decreased relative to baseline, this is indicative that a treatment is ineffective at slowing the progression of the disease. Based on the exemplary results, a treating physician can consider whether or not to change the course of treatment once it becomes apparent that a current course of treatment is ineffective.

Exemplary Methods for Evaluating Changes to Skin

In yet another exemplary aspect of the present disclosure, the exemplary methods and systems can be used to detect changes in a patient's skin, including skin thickening, improvement in scarring, changes in eczema and/or psoriasis, and the like. This can be particularly relevant in connection with osteogenesis imperfect, Ehlers-Danlos, Syndrome, Infantile cortical hyperostosis aka, Caffey's disease, and determining the effectiveness of a particular treatment. For example, psoriasis is commonly treated using topical and orally administered treatments, such as corticosteroids (e.g., betamethasone, clobetasol, fluocinonide, desoximetasone, hydrocortisone, fluticasone, others), Anthralin (Zithranol™—RR; Elorac), Calcipotriene (Dovonex®; Leo), and Calcitriol (Vectical®; Galderma). The skin of a patient suffering from psoriasis can be monitored, for example, by looking at the skin's lipids and protein metabolism, to determine which treatment is effective.

One exemplary way to determine the efficacy of a treatment being applied to skin, or being administered systemically to treat a skin disorder, is to track the levels of various proteins, such as collagen, which can be present inside the skin. For example, the disease scleroderma is associated with excessive deposition of collagen, so baseline levels of collagen before treatment, and subsequent levels of collagen after treatment, can be used to follow the course of treatment and determine whether or not the treatment is effective. For example, collagen type 1 is the most abundant collagen of the human body. It is present in scar tissue, the end product when tissue heals by repair. It is found in tendons, skin, artery walls, the endomysium of myofibrils, fibrocartilage, and the organic part of bones and teeth. It is related to the COL1A1 and COL1A2 genes. Representative disorders associated with collagen 1 include osteogenesis imperfect, Ehlers-Danlos, Syndrome, Infantile cortical hyperostosis aka, and Caffey's disease. The course of treatment can be followed by monitoring collagen type 1 to determine whether or not the treatment is effective.

The exemplary system, method and computer-accessible medium, according to an exemplary embodiment of the present disclosure, can utilize an optical imaging procedure to determine information about the skin of a patient. For example, the information can include metabolic activity of the skin or skin cell of the patient. For example, the metabolic activity can include, but is not limited to, how the skin or skin cells generate lipids and proteins. In order to determine the metabolic activity, a compound can be administered to a patient, which can include a vibrational probe. Exemplary compounds can include, but are not limited to, heavy water and glucose. After a certain amount of time has lapsed since the compound is administered, the skin can be imaged using an optical imaging procedure. Exemplary optical imaging procedures include, but are not limited to, an infrared imaging procedure and a SRS imaging procedure.

The exemplary results of the imaging procedure can include a signal that includes the combined signals from lipids and proteins. The exemplary system, method and computer-accessible medium, according to an exemplary embodiment of the present disclosure, can be used to split or separate the combined signal into a separate lipid signal and a separate protein signal. These separate signals can be used to analyze the metabolic activity of the skin. Additionally, the metabolic activity can be used to determine the efficacy of a drug. For example, a drug can also be administered to the patient (e.g., orally or topically). After a certain amount of time has lapsed for the drug to take effect, the compound can be administered to the patient, the imaging procedure can be performed, and the protein and lipid signals can be separated in order to be analyzed.

The exemplary system, method and computer-accessible medium, according to an exemplary embodiment of the present disclosure, can be incorporated or included into a handheld device that can provide the metabolic activity. For example, the handheld device can include an optical emitter and an optical detector (e.g., for infrared imaging or SRS imaging). The information obtained can be analyzed using a computing device stored locally on the handheld device, and the metabolic activity can be provided to the user. Alternatively or in addition, the handheld device may only include the optical emitter and detector, and the information is provided to an external computing device using a connection to the handheld device. The connection can be any suitable wired or wireless connection. Additionally, the handheld device can be battery powered (e.g., using rechargeable or non-rechargeable batteries) or it can be connected or coupled to an external power supply.

The exemplary handheld device can be used to analyze metabolic activity in or on various suitable biological structures. Exemplary biological structures include skin, skin cells, or bodily fluids of a patient. Bodily fluids can include, but are not limited to, blood, plasma, saliva, tears, semen, or any other bodily fluid that can be measured for metabolic activity.

The Skin's metabolic activities or regeneration can include protein synthesis (e.g., collagen), lipids synthesis, carbohydrates synthesis, protein degradation etc., different layers of skin contains different cell types. The metabolic activities of each cell type can be related to its function to the skin. For example, sebaceous glands are actively synthesizing lipids for moisturizing skin and hair. The lipids synthesis inside the glands cells can be visualized to examine the metabolic changes under certain diseases or treatment. Heavy water labeling combining with vibrational imaging can provide the information of metabolic changes with subcellular resolution, and can be used to quantify the changes through imaging analysis.

Exemplary Other Spectroscopic Methods which can be Used

In some exemplary embodiments of the present disclosure, rather than using SERS, the spectra can be obtained using other vibrational imaging procedures, including, but not limited to, TERS, Fourier-Transform Infrared Imaging, AFM-IR, Optical Photothermal IR microscopy, Infrared Photo Induced Force Microscopy, and Peak Force Infrared Microscopy, particularly where the procedure is used to study metabolic activity.

To use these other spectroscopic procedures, as with SRS, peaks associated with lipids, proteins, and genetic material, which peaks can be associated with C-D bonds rather than C—H bonds, can be determined. Appropriate procedures for splitting the peaks into peaks associated with lipids, proteins, and/or genetic material can be used, based on the degree of separation of the peaks of interest in a given spectroscopic procedure. For example. Fourier-transform infrared spectroscopy ("FTIR") or FTIR imaging system and its derivatives, Fourier transform infrared spectro-microtomography.

Exemplary embodiments of the present invention can be further understood with reference to the following non-limiting examples:

Example 1: Exemplary $D_2O$ as a Contrast Agent for Metabolic Activities

Water ("$H_2O$") diffuses freely across cell and organelle membranes and participates in the vast majority of biochemical reactions. As an isotopologue of water, heavy water ("$D_2O$") can rapidly equilibrate with total body water in all cells within an organism and label cellular biomolecules with deuterium ("D") by forming a variety of X-D bonds through non-enzymatic H/D exchange and enzymatic incorporation. (See e.g., diagram shown in FIG. 1A). The former can be spontaneous and reversibly forms oxygen-deuterium ("O-D"), nitrogen-deuterium ("N-D"), and sulfur-deuterium ("S-D") bonds on existing molecules, whereas the latter depends on enzyme-catalyzed chemical transformation that irreversibly breaks the O-D bond and forms C-D bonds on newly synthesized molecules. (See, e.g., Reference 5). Through such transformation, deuterium quickly labels the metabolic precursors, such as non-essential amino acids ("NEAAs"), acetyl-CoA, and deoxyribose, which can then be slowly incorporated into proteins, lipids, and DNA, respectively. (See e.g., References 6-8; and diagram shown in FIG. 1A). As often the rate-limiting step, the synthesis of C-D bond-containing macromolecules from the precursors can be governed by cellular metabolic activities. Therefore, $D_2O$ can be used as a universal probe to track metabolic rate through the emergence of C-D bond-containing macromolecules (hereinafter referred to as D-labeled macromolecules).

Raman spectroscopy provides a noninvasive, optical approach to distinguish metabolic incorporation from non-enzymatic exchange in situ, because various X-D bonds have intrinsically distinct stretching vibrational features. The Raman spectrum of C-D bond was clearly separated from those of C—H, O-D in $D_2O$, and the non-enzymatically formed O-D, S-D and N-D bonds (see e.g., graph shown in FIG. 1B), which facilitates the direct detection of biosynthetic incorporation of deuterium through the amount of C-D bonds. Spontaneous Raman microspectroscopy has recently been employed to identify metabolic activity in bacteria after $D_2O$ treatment (see, e.g., References 9 and 10), although this approach can have difficulties in generating spatially resolved images due to low sensitivity and slow imaging speed. Compared to spontaneous Raman spectroscopy, SRS microscopy can be provided as an emerging non-linear Raman imaging technology with substantial sensitivity boost through quantum amplification by stimulated emission, which facilitates at least three orders of magnitude faster acquisition time, fine spectral resolution, compatibility with fluorescence, and 3D optical sectioning capability in tissues and even living animals. (See, e.g., References 11-14). These advantages of SRS microscopy, combined with the exemplary new discoveries of the chemical features of the C-D vibrational spectrum (described below), led to the development of the exemplary DO-SRS, which uses $D_2O$ as a imaging contrast agent to specifically trace lipid, protein, and DNA metabolism in cells and tissues.

The exemplary DO-SRS imaging of metabolism in cultured cells was demonstrated. By treating HeLa cells with medium containing 70% $D_2O$ for 24 hours (e.g., toxicity only arises when $D_2O$ concentration exceeded 80% (see e.g., graphs and images shown in FIG. 10) and then tuning SRS to target the C-D frequency, it was found that that C-D signal was undetectable at the beginning of the treatment but increased dramatically in all cells at 24 hours. (See e.g., graph shown in FIG. 1B). This result confirms that C-D signal specifically and effectively reports newly synthesized molecules, whereas C—H signal represents pre-existing pool of molecules. Beneficially, the separation between the O-D peak and the C-D peak means that C-D signal can be free of interference from the overwhelming O-D background, thus washing off the $D_2O$ probe before imaging can be unnecessary.

Example 2: Exemplary Sensitivity and In Vivo Live Imaging Capacity of DO-SRS

In humans, deuterium can be widely used as a stable isotope to measure body composition and metabolic rate. (See. e.g., References 15-17). Daily intake of 60 to 70 ml $D_2O$, which can result in approximately 2% body water enrichment, does not cause any adverse symptoms (see, e.g., References 18 and 19), and can be considered to be safe. It was found that a comparable level (e.g., approximately 2.4 to approximately 2.8%) of enrichment in mice by administration of 4% $D_2O$ as drinking water (e.g., the dilution of body water relative to drinking water can typically be approximately 30 to approximately 40% in rodents (see. e.g., Reference 19) produced easily detectable C-D signals in sebaceous glands. (See e.g., images and graph shown in FIG. 1C).

In mice, $D_2O$ enrichment below 20% did not cause any effect on physiological processes, including no acute adverse events, no effects on cell division in all major cell renewal systems, no perturbation on physiology, growth, appetite, and reproduction, and no teratogenic effects, even in multigenerational studies. (See, e.g., References 17, 20 and 21). Thus, mice were given 25% $D_2O$ as drinking water to achieve a safe level (e.g., approximately 15 to approximately 17.5%) of enrichment in body water and obtained a 6-fold increase in C-D signal compared to that from mice drinking 4% $D_2O$. (See e.g., image and graph shown in FIG. 1C). The nearly linear relationship between 20 enrichment and signal intensity facilitated the extrapolation of the detection limit (See e.g., image and graph shown in FIG. 1C). Administration of 1.4% $D_2O$ (e.g., approximately 0.9% enrichment) can be sufficient to achieve a signal-to-noise ratio ("S/N") of 10, and for S/N higher than 2, administration of 0.3% $D_2O$ can be needed. Although detectable signal can be generated at low $D_2O$ enrichment, approximately 16% $D_2O$ enrichment was chosen (e.g., from oral administration of 25% $D_2O$) in the following mouse studies in order to achieve large dynamic range and also reveal low biosynthetic activity within a short time frame.

The wash-free aspect of the exemplary DO-SRS facilitates the imaging of real-time C-D signal dynamics of live cells and intact animals in the presence of $D_2O$. In vivo live imaging of the sebaceous glands was performed under the ear skin of anesthetized mice that drank 25% $D_2O$ for 9 days. Leveraging the 3D optical sectioning and substantial imaging depth of nonlinear excitation of SRS (e.g., about hundreds of microns), clear C-D signal in sebocytes were observed in living mice. (See e.g., images shown in FIG. 1D). At a whole-organism level, C-D signals in moving *C. elegans* larva growing in a 20% $D_2O$ environment (see e.g., images shown in FIG. 1E) were monitored. In *C. elegans*, <60% $D_2O$ concentration had no observable toxicity and did not affect cell division. (See e.g., graphs and images shown in FIG. 10). With the above proof of concept, the safeness of $D_2O$ as a probe, combined with the sensitivity and penetration of SRS as a detection mechanism, can facilitate long-term in vivo tracking of metabolic activities.

Example 3: Exemplary Macromolecule-Specific C-D Vibrational Frequencies

Because $D_2O$ can be a universal probe and facilitates the labeling of different types of macromolecules, the C-D signal generated from $D_2O$ probing can be considered to report the total metabolic activity. Whether sufficiently distinct C-D vibrational frequencies exist to facilitate the separation of different types of D-labeled macromolecules can be unaddressed.

To address this matter, the spectral knowledge of C—H region can be translated to the C-D region. However, this translation may not apply. C—H stretching vibrational spectra contain a main peak at 2940 cm (e.g., denoted as $CH_P$ channel) originating from protein-related $CH_3$ stretching, a main peak at 2845 $cm^{-1}$ (e.g., $CH_L$ channel) from lipid-related $CH_2$-stretching, and a shoulder peak at 2967 $cm^{-1}$ (e.g., $CH_{DNA}$ channel) from DNA-related C—H stretching. (See, e.g., References 22-24). However, the C—H spectral distinction (e.g., based on the number of covalent hydrogen atoms) cannot be simply translated to C-D stretching, because $CD_2$ and CD groups can rarely exist under relatively low $D_2O$ enrichment (e.g., approximately 15 to approximately 17.5%) in body water. Such low $D_2O$ concentration means that deuterium could only sparsely label the newly synthesized macromolecules (see e.g., diagram shown in FIG. 1A), and the C-D vibrational signal can be dominated by CD mode (e.g., only one carbon-bonded H atom can be replaced by D atom).

To dissect the spectral features of C-D vibrational modes upon $D_2O$ treatment, the C-D region (e.g., 2109-2210 $cm^{-1}$) was scanned, 5 Raman shifts with equal intervals were tested, and identifiable difference among the 5 images (see e.g., images shown in FIG. 2A) were found. C-D images acquired at lower wavenumbers (e.g., especially 2135 $cm^{-1}$) resembled the cellular distribution patterns of lipids from the $CH_L$ channel, and images acquired at higher wavenumbers (e.g., especially 2185 $cm^{-1}$) resembled the protein signal from $CH_P$ channel in all tissues tested, including fibroblast-like COS7 cells, C. elegans larva, zebrafish embryos, and mouse tissues. (See e.g., images shown in FIG. 2A). Thus, the signal at 2135 $cm^{-1}$ can represent newly synthesized D-labeled lipids and the signal at 2185 cm as D-labeled proteins.

To confirm the above, it was found that inhibiting protein synthesis with anisomycin in $D_2O$-treated HeLa cells led to a peak centered at 2135 $cm^{-1}$, representing the remaining D-labeled lipid signal, and blocking lipid synthesis with fatty acid synthase inhibitor TVB-3166 led to a peak centered at 2185 $cm^{-1}$, representing the remaining D-labeled protein signal. (See e.g., graph shown in FIG. 2B). The sum of the signals from the two treatments appeared similar to the control group treated only with $D_2O$. At the tissue level, removing proteins by proteinase K treatment in mouse tissues abolished the peak at 2185 $cm^{-1}$, and dissolving lipids using methanol abolished the peak at 2135 $cm^{-1}$. (See e.g., graph shown in FIG. 2C). Applying methanol wash to multiple mouse tissues from various organs, the average spectra for D-labeled lipids (e.g., signal reduction by methanol wash) and proteins (e.g., residual signal after methanol wash) were determined, which consistently showed peaks at the two frequencies. (See e.g., graph shown in FIG. 2D). The above data confirmed macromolecule-specific Raman shifts for D-labeled lipids and proteins at 2135 $cm^{-1}$ (e.g., denoted as $CD_L$ channel) and 2185 $cm^{-1}$ (e.g., $CD_P$ channel), respectively.

The chemical basis of spectral distinction in CD vibration was determined by comparing D-labeled lipid and protein spectra with assigned CD vibrational modes in model compounds. The peak of D-labeled lipid at approximately 2140 $cm^{-1}$ matched well with the singly deuterated C-D stretching in 12-D1-palmitic acid but not the $CD_2$ symmetric stretching mode at approximately 2100 $cm^{-1}$ in perdeuterated palmitic acid (e.g., D31-) (see e.g., graph shown FIG. 2E), supporting the idea of sparse labeling (see e.g., diagram shown in FIG. 1A). Similarly, the D-labeled protein peak around 2185 $cm^{-1}$ matched the peak for C($\alpha$)-D vibration in D4-alanine but not the other three peaks assigned to the side chain CD group. (See e.g., Reference 25; and graph shown in FIG. 2F). This pattern also supported sparse labeling and indicated that most of the deuterium labeling in newly synthesized proteins occurred at the a carbon position through reversible transamination of free AAs. (See e.g., Reference 26; and diagram shown in FIG. 1A).

The above evidence indicates that the underlying principle for the observed spectral separation of D-labeled lipids (e.g., around 2140 $cm^{-1}$) and proteins (e.g., around 2185 $cm^{-1}$) can be the inherently distinct chemical environments of the constituting fatty acids and amino acids-deuterium-bonded carbon atoms in a hydrocarbon chain of lipids and the main chain of polypeptides can be connected to chemical groups with different polarities. By chemically isolating the major macromolecules (e.g., lipids, proteins, and DNA) from $D_2O$-treated HeLa cells, it was found that the Raman spectra of D-labeled lipids and proteins matched well with the corresponding spectra obtained in situ, as expected, and that the Raman peak of D-labeled DNA was blue-shifted compared to D-labeled proteins. (See e.g., graph shown in FIG. 2G). Deuterium labels DNA with higher chance at the C1' and C2' positions on the deoxyribose (see. e.g., References 19 and 27), and the blue shift of DNA's CD peak can be attributed to the fact that more carbon atoms in deoxyribose can be bonded to electronegative oxygen atoms. Based on the spectra of the cellular extracts, DNA at 2210 $cm^{-1}$ was imaged (e.g., designated as $CD_{DNA}$ channel).

Example 4: Exemplary Spectral Un-Mixing of Signals for D-Labeled Macromolecules

Although the peaks of CD signals in lipids, proteins, and DNA can be separated, their overall spectra overlap substantially. (See e.g. graphs shown in FIGS. 2D and 2G). Thus, a three-component un-mixing procedure was developed to computationally decompose the mixed CD signals into three macromolecule-specific elements. Applying the method to dividing cells, D-labeled lipids, proteins, and DNA were successfully separated, removing the bleed-through signal for each channel. (See e.g., shown in FIG. 3A). Since $C_{DNA}$ signal was very weak in non-dividing cells, only $CD_L$ and $CD_P$ signals were unmixed using a simplified two-component equation in most experiments. The un-mixing effectively removed residual bleed-through signals in $CD_L$ and $CD_P$ channels, revealing the genuine distribution of D-labeled lipids and proteins. (See e.g., images and graphs shown in FIGS. 3A-3G and FIGS. 11A-11F).

Overall, the exemplary un-mixing procedure facilitates, for the first time, in situ deconvolution of D-labeled lipids and proteins signal via SRS microscopy. It can be worth noting the difference between the exemplary un-mixing procedure developed and the label-free counterpart previously reported. Unlike the un-mixing of $CH_L$ and $CH_P$, which used pure standard compounds (e.g., oleic acid for lipids and Bovine Serum Albumin for proteins) (see. e.g., References 22 and 23), the exemplary un-mixing method can be tailored for sparse labeling pattern of deuterium incorporation in vivo. Without commercially available standards for randomly, sparsely deuterated lipids and proteins, standards were generated using either chemically isolated or in situ D-labeled lipids and proteins to determine the un-mixing coefficients. The ability to separate the signals for D-labeled lipids and proteins facilitated simultaneous visualization of the metabolic dynamics of lipid and protein in the same tissue, which can be beneficial for addressing many fundamental questions about the different pathways of cellular metabolism.

Example 5: Exemplary Optical Imaging of De Novo Lipogenesis Via DO-SRS

Previously, others have developed methods to visualize lipogenic activities in living tissues by supplying deuterium-labeled fatty acids ("D-Fas"), such as palmitic acid, oleic acid, and arachidonic acid, and imaging C-D bonds in newly synthesized lipids. (See, e.g., References 28-1). However, the exemplary DO-SRS can be fundamentally different from those previous methods because $D_2O$ can be a noninterfering probe that does not affect native metabolism and can be a non-carbon tracer that can probe activities of de novo lipogenesis.

D-FAs can be known to be taken up by cells through scavenger pathways and then incorporated directly into lipids, whereas D$_2$O freely diffuses into cells and labels newly synthesized lipids through de novo lipogenesis. Moreover, the dependence on cellular uptake for D-FAs can also result in bias among various cell types, which does not occur for D$_2$O probing. The different effects of these two types of probes can be clearly evident in cultured cells. For example, supplementation of D-labeled palmitic acids ("D-PA") or oleic acids ("D-OA") in HeLa cells led to the accumulation of CD$_L$ signal in lipid droplets (see e.g., images shown in FIG. 4A), whereas D$_2$O probing generated very few lipid droplets in both CD$_L$ and CH$_L$ channels and produced much more uniform CD signal in cytoplasmic membrane structure.

The large number of lipid droplets caused by the treatment of D-FAs even at low concentrations (e.g., 10 µM) suggests that exogenous fatty acids likely perturbed native cellular metabolism. Moreover, different types of fatty acids altered lipid metabolism in distinct ways; for the same HeLa cells, treatment of 10 µM D-OA generated remarkably more lipid droplets than D-PA. (See e.g., images shown in FIG. 4A). It has also been found that PA, but not the unsaturated OA, when applied at higher concentration (e.g., approximately 200 µM), drove the formation of solid-like microdomain and membrane phase separation in endoplasmic reticulum. (See. e.g., Reference 30). Thus, compared to D-FAs, D$_2$O, as a metabolic bystander, can be a superior probe for monitoring endogenous lipogenesis in general.

Example 6: Exemplary DO-SRS Tracks Lipid Metabolism in C. elegans

In animals, first the exemplary DO-SRS imaging was applied to assess how much de novo synthesis contributes to the production of total lipids in C. elegans, which relies on both dietary uptake (e.g., from food source E. coli bacteria) and de novo lipogenesis for total lipid synthesis. For the quantification purpose, CD$_L$/CH$_L$ as a ratiometric indicator was developed for the amount of newly synthesized lipids normalized against variations among individuals and heterogeneity within the same tissue (e.g., see Methods). It was found that, when both growing on 20% D$_2$O plates, animals fed on non-labeled bacteria (e.g., grown in H$_2$O) had much lower CD$_L$/CH$_L$ ratio (e.g., approximately 3.1%) than animals fed on D-labeled bacteria (e.g., approximately 22.3%; see e.g., graph shown in FIG. 4B and images and graph shown in FIGS. 12A-12C12), indicating that approximately 14% of total lipids were synthesized de novo and the rest approximately 86% were incorporated or modified from E. coli fatty acids. This result agrees with previous mass spectrometry studies using dietary $^{13}$C labeling, which found that C. elegans only de novo synthesized approximately 7% of palmitate and approximately 12% to approximately 19% of eighteen-carbon fatty acids from acetyl-CoA. (See. e.g., Reference 32). However, compared to mass spectrometry, which can only measure metabolic incorporation of isotopes in a bulk of thousands of worms, the exemplary DO-SRS in situ imaging detects metabolic activity at the individual animal level, utilizes much less materials, and can reveal variations among individuals.

D$_2$O can be a superior probe to D-FAs for detecting lipogenesis in C. elegans for the following reasons. First, CD$_L$ signals generated by D$_2$O probing and D-FA supplementation (see e.g., images and graph shown in FIG. 12) were compared, which found that although both labeled lipid droplets in similar patterns, 20% D$_2$O treatment produced over two-fold stronger CD$_L$ signal than 4 mM deuterated palmitic acid, the highest concentration used in previous studies. (See. e.g., References 29 and 31). Second, D$_2$O can be able to track the approximately 14% lipids generated by de novo lipogenesis, whereas D-FAs cannot. Third, because bacteria grown on D$_2$O plates produce a variety of D-labeled fatty acids, lipids, and their metabolic intermediate, which all become dietary nutrient for C. elegans, D$_2$O probing (e.g., by generating D-labeled bacteria) can monitor lipid synthesis more accurately and more robustly than the supplementation of a single type of D-FA. Fourth, D$_2$O probing also generates D-labeled protein signals in addition to lipid signals, whereas D-FA treatment does not. (See e.g., images and graph shown in FIG. 12).

The exemplary DO-SRS can also facilitate the evaluation of the dynamics of lipid metabolism in C. elegans. When transferred from H$_2$O plates to 20% D$_2$O plates, normal fourth stage larva ("L4") showed newly synthesized lipid droplets in the intestine in as early as 20 minutes CD$_L$ signal continued to increase for 6 hours and expanded into hypodermis, suggesting fast and robust lipogenesis. (See e.g., images shown in FIG. 4C). In contrast, when developmentally arrested dauer larva were placed onto D$_2$O plates with food (e.g., E. coli bacteria), new lipid signals did not appear until 6 hours after the transfer and took 16 hours to reach the 6-hour intensity of normal larva. (See e.g., graph shown in FIG. 4D). The different dynamics of normal and dauer larva reflects the additional time utilized for dauers to exit the non-feeding, diapause stage and to resume metabolic activities and life cycle. (See, e.g., References 33 and 34). Interestingly, the exemplary data connects metabolic dynamics to previously reported changes in transcriptome during this dauer recovery process, because the onset of lipogenic activities closely follows the expression of genes involved in glycolysis, tricarboxylic acid cycle, fatty acid oxidation, and oxidative phosphorylation. (See, e.g., Reference 34). This result can suggest that the buildup of storage fat in recovering dauers began after the production of ATP from food digestion and can be beneficial for the preparation of dauer-to-L4 molt, during which food intake stopped and CD$_L$ signal stayed flat (e.g., 8 to 12 h; see e.g., graph shown in FIG. 4D).

Lipid degradation can be monitored through a pulse-chase experiment. For example, L4 animals were first pulsed for one hour on 20% D$_2$O plates and then transferred back to regular H$_2$O plates. CD$_L$ signal dropped by approximately 60% in the first five hours (see e.g., graph shown in FIG. 4E), suggesting a quite fast lipid turnover in the developing larva. Thus, the exemplary DO-SRS facilitated the visualization of both lipid anabolism and catabolism.

Example 7: Exemplary Visualizing De Novo Lipogenesis in Mice

By adding D$_2$O to the drinking water of mice, previous studies showed the incorporation of deuterium into the total biomass in various mouse organs but could not image and differentiate D-labeled lipids and proteins in situ. (See, e.g., References 5-8). Using the exemplary DO-SRS imaging with macromolecular selectivity, it was found that different mouse organs show metabolic preference to either protein or lipid biosynthesis, which reflects their different functions. (See e.g., images shown in FIGS. 13A-13C). For example, lipid-rich tissues, such as sebaceous glands, myelin sheath in the brain, and adipose tissues, showed strong CD$_L$ signal and weak CD$_P$ signal. (See e.g., images and graphs shown in FIGS. 5A-5H and images shown in FIGS. 13A-13C).

Because the visualization of in situ lipid synthesis dynamics in mouse models had been particularly challenging with previous methods, which mostly capture the static level (see, e.g., Reference 35), the utility of the exemplary DO-SRS was determined in evaluating the development and metabolic homeostasis of the lipid-rich tissues and to gain new insights into mammalian lipogenesis.

First, the spatiotemporal dynamics of lipogenic activities were analyzed during holocrine secretion. Previous studies imaged the total lipids in sebaceous glands using label-free CARS microscopy and found that sebocytes near the duct had the highest abundance of lipids. (See, e.g., Reference 36). But whether those cells also have the highest lipogenic activity can be unclear. By imaging sebaceous glands collected under the ear skin of 3-month old mice that drank 25% $D_2O$ for 2, 8, or 26 days, respectively, it was found that active lipid synthesis occurred mostly in the peripheral sebocytes at day 2, although $CH_L$ images indicated the presence of a large amount of lipids throughout the entire gland. (See e.g., images shown in FIG. 5A). The $CD_L$ signal increased and expanded into the center of the gland later at day 8 and 26, as sebocytes migrated towards the duet and accumulated more lipids. (See e.g., images shown in FIG. 5A and graph shown in FIG. 5B). These exemplary results indicated that the outermost early sebocytes, instead of the inner mature sebocytes, had the highest lipogenic activity. At day 26, $CD_L/CH_L$ ratio reached approximately 0.2, which can be close to the maximal D:H ratio (e.g., approximately 0.18 to approximately 0.21) body water from approximately 15 to 17% $D_2O$ enrichment; thus, all the observed lipids were newly synthesized, and a likely complete lipid turnover had occurred.

Second, the myelination dynamics of axon bundles in the developing brain were visualized. Previous studies indicated that myclinogenesis occurs predominantly postnatally in mammals (see, e.g., Reference 37), but it can be rather difficult to obtain the precise timing of myelination in a specific region of the brain with traditional methods. By feeding pups for 6 days (e.g., P0-P5 or P6-P11) with milk from mother that drank 25% $D_2O$, strong bundle-like $CD_L$ signal labeling the myelinating thalamocortical fibers in the internal capsule was observed in the second postnatal week (e.g., imaged at P11) but not in the first week (e.g., imaged at P5) and not in adults. (See e.g., images shown in FIG. 5C). Interestingly, previous studies observed organized growth of thalamocortical projection during the first postnatal week (see, e.g., Reference 38), and the exemplary data suggests that myelination of those fibers occurred shortly after the axonal development within astringent time window. In contrast, other axonal fiber-rich structures like hippocampus and olfactory bulbs, which mostly developed embryonically, did not show significant change in myelination activities during the same period of time. (See e.g., images shown in FIG. 5C and graph shown in FIG. 5D).

Third, different metabolic dynamics of brown adipose tissue ("BAT") and white adipose tissue ("WAT") in situ were observed during development and disease. BAT and WAT were identified based on (i) that adipocytes in WAT contain one single, large fat droplet, and adipocytes in BAT contain many small lipid droplets and (ii) that BAT can have stronger autofluorescence than WAT due to high levels of cellular NADH and flavin. It was found that BAT can have higher lipogenic rate (e.g. $CD_L/CH_L$ ratio) in juvenile (e.g., P25) mice than in adult mice (see e.g., images shown in FIG. 5E and graph shown in FIG. 5F), consistent with the beneficial thermogenic function of BAT in young animals. (See, e.g., Reference 39). WAT can serve as energy storage; and age-related increase in the percentage of body fat can often be attributed to decrease in resting metabolic rate. (See, e.g., Reference 40). However, it was found that WAT in adult mice synthesizes and accumulates more fat than WAT in juveniles within the same $D_2O$ probing period, suggesting that increased lipogenesis can also be responsible for fat accumulation in adults. Genetically obese (e.g., leptin-deficient ob/ob) mice also showed much higher lipogenic activities in WAT than did the wild-type mice, indicating that obesity induces ectopic lipogenesis, in addition to fat accumulation. (See e.g., images shown in FIG. 5G and graph shown in FIG. 5H). Thus, the exemplary DO-SRS can serve as a general phenotyping tool for fat metabolism and energy homeostasis in both normal development and disease.

It was determined that $D_2O$ administration via drinking water labeled newly synthesized lipids much more efficiently than the injection of D-FAs. Intravenous injection of 5.76 µmol D-PA into mice over the course of three days did not produce significant signal in any tissue. On the other hand, administration of high concentration of D-PA (e.g., via intraperitoneal bolus injection of 96 µmol D-PA) led to the accumulation of $CD_L$ signal in the ER membrane of pancreatic cells (see e.g., images shown in FIGS. 13A-13C), suggesting that, unlike $D_2O$ probing, the D-FA treatment can affect native metabolism in animals by promoting the formation of solid-like domains in the ER. (See, e.g., Reference 30).

Example 8: Exemplary DO-SRS Facilitates In Vivo Tracking of De Novo Protein Synthesis Protein synthesis activity can be another major component of metabolic dynamics. To visualize newly synthesized proteins in mice in vivo, previous studies administered 2.5 mg/ml of D-labeled amino acids ("D-AAs") via drinking water for 12 days and observed CD signals only in liver and intestine tissues but no other organs. (See, e.g., Reference 41). This tissue bias can be explained by the unequal uptake of orally administered D-AAs among different organs, heterogeneity of AA pools, and the poor labeling efficiency of D-AAs. (See, e.g., Reference 26). Moreover, the possible varying incompleteness of mixing D-AAs with pre-existing AA pool makes the measurement of protein synthesis rate complicated. In contrast, $D_2O$ can have higher labeling efficiency and consistency because $D_2O$ freely diffuses into all tissues and rapidly labels free AAs through transamination (see, e.g., Reference 26), making the $CD_P$ signal generated by D>0 probing more accurately reflect the distribution of newly synthesized proteins than the signal from D-AA labeling.

The D-AA concentration (e.g., or density) in the free AA pool inside cells (e.g., <10 mM)(see, e.g., Reference 42) can be below the exemplary detection limit (e.g., approximately 20 mM for singly deuterated molecules), so $CD_P$ signal only reports D-AAs incorporated into proteins. In addition, it was found that there was no post-translational labeling of proteins by $D_2O$-derived deuterium (see, e.g., Reference 26), thus $D_2O$ probing only tracks protein synthesis and not post-translational modification.

To demonstrate that $D_2O$ can be an efficient, consistent, and cost-effective tracer of de novo protein synthesis, a direct comparison between 8-day administration of 25% $D_2O$ and 2 mg/ml of D-AAs both via drinking water was performed. Indeed, D-AA treatment only produced significant $CD_P$ signals in the digestive tract and liver, where $D_2O$ probing resulted in much stronger signal. (See e.g., images shown in FIG. 6). In the pancreas, D-AA treatment generated weak and sparse signal for protein synthesis activity, whereas $D_2O$ probing was much more sensitive and revealed broader regions of the tissue that actively synthesized proteins. Moreover, in organs, such as hippocampus, cortex, muscle, and thymus, oral intake of D-AAs hardly produced any $CD_P$ signal due to tissue bias, whereas $D_2O$ probing was not subjected to such bias and generated strong CD signal labeling newly synthesized proteins. In terms of the cost, $D_2O$ administration (e.g., approximately \$0.67/mouse/day at 25%) can be 15 times cheaper than D-AA treatment (e.g., approximately \$10/mouse/day at 2 mg/ml), making $D_2O$ a much more economical tracer for long-term in vivo labeling of slow-turnover proteins.

Although non-drinking administration such as injection of D-AAs directly into the bloodstream via carotid artery could enhance CD signals and facilitate the labeling of proteins in organs, such as pancreas and brain cortex, it was found that the signal can still be weaker than that generated by $D_2O$ probing. In general, D-AA injection to bloodstream only labels tissues with strong protein synthesis activity and can be less sensitive than $D_2O$ treatment, which can reveal low levels of de now protein biosynthesis activities. Furthermore, for organs like hippocampus, injection of D-AAs still could not generate any clear $CD_P$ signal (see e.g., images shown in FIGS. 13A-13C), suggesting that the D-AA labeling bias against certain tissues can be inherent to the probe and could not be overcome by increasing D-AA concentration. Compared to the infusion of D-AAs, 20 administration through drinking water can also be much more convenient, enabling large-scale animal experiments.

Example 9: Exemplary Simultaneous Visualization of Lipid and Protein Metabolism

Another significant advantage of the exemplary DO-SRS, compared to D-FA or D-AA treatment alone, can be the ability to simultaneously acquire signals for D-labeled lipids and proteins and then resolve their accurate distribution on the same sample through spectral un-mixing, with only one probe ("$D_2O$"). This capacity facilitates the evaluation of both lipid and protein metabolism at the same time in an integrated manner.

Protein and lipid syntheses in C. elegans were visualized simultaneously during germline development and revealed their different metabolic dynamics. Previous studies suggested that cholesterol, fatty acids, and other nutrients can be transported to developing oocytes via yolk particles, but it can be unclear when exactly lipid deposition occurs during germ cell development and whether there can be any difference between protein and lipid accumulation in oocytes. (See. e.g., Reference 43). It was found that the mitotic and meiotic germ cells showed very active protein synthesis ("$CD_P$") but low level of lipid synthesis ("$CD_L$") signals in L4 animals, whereas the post-pachytene, maturing oocytes in day 0 adults accumulated significant amount of newly synthesized lipids in a 3-hour period. (See e.g., graph shown in FIG. 7A, and images shown in FIG. 7B). Thus, the exemplary results suggest continuous protein synthesis and accumulation throughout germline development and temporally restricted lipid deposition into late-stage oocytes.

Lipid and protein metabolism also showed different age-related changes in C. elegans. In general, overall lipid synthesis rate dropped continuously from adult day 0 to day 7, indicating a decline in lipogenesis during aging. The rate of protein synthesis declined most significantly after adult day 5, showing different dynamics from lipids. (See e.g., graph shown in FIG. 7C).

The subcellular resolution afforded by the exemplary DO-SRS also facilitated the determination of distinct spatial patterns of biosynthesis. Previous studies reported unregulated synthesis and body-wide accumulation of yolk proteins and lipids in the absence of oogenesis in post-reproductive C. elegans using either yolk protein::GFP reporter or electron microscopy. (See, e.g., References 44 and 45). However, fluorescent labeling can have high background and cannot differentiate proteins from lipids; EM studies revealed yolk proteins and lipids as different electron-dense materials but can be laborious and time-consuming. Both methods can provide only a static view of yolk production, and it may not be clear whether the pattern of yolk synthesis changes as the adults age.

Using the exemplary DO-SRS, it was found that from adult day 3 the majority of worms showed significant $CD_L$ and $CD_P$ signal as clumps in the intestine and throughout the body cavity after a three-hour $D_2O$ probing. (See e.g., graph shown in FIG. 7D and images shown in FIG. 7E). $CD_P$ signal appeared to be stronger than $CD_L$, signal in older adults (e.g. day 8) but not in younger adults (e.g., day 5), indicating more persistent yolk protein synthesis compared to lipogenesis. The exemplary images not only provided a direct visualization of yolk lipid and protein production but also surprisingly revealed some spatial restriction for the previously considered unregulated biosynthesis of yolk materials. For example, it was found that $CD_P$ signals appeared in both pre-existing mass and newly formed clumps in younger adults (e.g. day 5), suggesting that newly synthesized proteins both accumulated into existing aggregates and formed new aggregates. However, $CD_P$ signals in older adults (e.g. day 8) only emerged in pre-existing mass, indicating that newly made proteins were only deposited into pro-formed aggregates in aged animals. Thus, the exemplary observation revealed an aging-dependent aggregation pattern for newly synthesized yolk proteins. The exemplary DO-SRS can serve as a useful tool to evaluate protein aggregation in situ.

Applying this procedure to zebrafish, differences in protein and lipid metabolism during embryonic development were identified. By incubating the embryos in egg water containing 20% $D_2O$ for 24 hours, significant $CD_P$ signal and little $CD_L$ signal were observed in all embryonically derived tissues, which suggests that the rate of protein synthesis, in general, can be much higher than the rate of lipogenesis during embryonic cell division. The zebrafish yolk sac, however, showed very weak signal in both $CD_P$ and $CD_L$ channels despite significant $CH_L$ and $CH_P$ signals from maternally deposited lipids and proteins. (See e.g., images and graphs shown in FIGS. 8A-8E). Since the yolk and blastoderm had similar water permeability (see, e.g., Reference 46), the exemplary result suggests very little zygotic biosynthesis in the yolk independently of maternal contribution. Overall, the exemplary observations relied on the in situ separation of D-labeled proteins and lipids, which cannot be easily achieved by previous methods.

The exemplary DO-SRS was used in conjunction with fluorescent microscopy to track the metabolic activity of specific cell lineages during development. Probing the embryos from zygote to 24 hours post-fertilization ("hpf"), it was found that a group of hemangioblast cells labeled by Tg(kdrl:EGFP) (see, e.g., Reference 47) had the strongest $CD_P$ signal. (See e.g., images shown in FIG. 8A). Those cells originate from lateral plate mesoderm and give rise to endothelial and hematopoietic lineages. (See, e.g., Reference 48). Their strong $CD_P$ signal can indicate active protein biosynthesis, possibly due to fast proliferation, during the 0-24 hpf period. $D_2O$ probing of later embryonic stages, 24-34 and 34-48 hpf, found that the EGFP-positive cells, which labeled mostly differentiated endothelial cells then (see, e.g., Reference 49), no longer showed stronger $CD_P$ signal than the surrounding tissues. (See e.g., images shown in FIGS. 8B and 8C and graphs shown in FIGS. 8D and 8E). Thus, by co-labeling with lineage-specific fluorescent marker, time-dependent metabolic activities of particular cell types can be tracked during lineage progression.

Example 10: Exemplary DO-SRS Visualizes Tumor Boundary and Metabolic Heterogeneity An exemplary biomedical application of the exemplary DO-SRS can be to visualize tumor boundaries and intratumoral metabolic heterogeneity. Although label-free SRS identified the boundary between glioblastoma and normal brain tissues (see, e.g., Reference 50), it relied on the protein/lipid compositional difference between the tumor and normal tissues—brain areas had higher myelin-derived lipid concentration than the tumor, which may not apply to other types of tumor. In contrast, the exemplary DO-SRS can reveal tumor boundaries by tumor's inherently higher metabolic activities than the surrounding normal tissues. For example, giving glioblastoma-bearing mice 25% $D_2O$ for 15 days, both stronger $CD_L$ and $CD_P$ signals in the tumor tissue were observed compared to the nearby brain tissues, even though the brain region had high total lipids in the $CH_L$ channel. (See e.g., images shown in FIG. 9A). Unlike the brain tumors, in the subcutaneous xenograft of colon tumor, the tumor and the surrounding skin tissue had similar composition of proteins and lipids and, hence, were indistinguishable by label-free SRS from their $CH_L$ and $CH_P$ signal. However, through $D_2O$ probing, the tumor showed higher level of lipogenesis than the skin and became readily identifiable in the $CD_L$ channel. (See e.g., images shown in FIG. 9B). Thus, this example showcases that the exemplary DO-SRS could be a more general and applicable method of detecting tumor boundaries than the label-free SRS.

Intratumoral metabolic heterogeneity can be considered a driver of tumor aggressiveness and has been under intensive evaluation due to its fundamental importance as well as prognostic significance. (See, e.g., Reference 51). In the colon tumor xenograft, cancer cells recruited stromal cells from the nearby normal tissues and developed into solid tumor. A three-day $D_2O$ probing revealed that human tumor cells had stronger biogenesis for both proteins and lipids than the recruited mouse stroma, showing metabolic heterogeneity inside the solid tumor. (See e.g., images shown in FIG. 9C). Interestingly, the difference between tumor and stroma became less pronounced after 15-day $D_2O$ intake, suggesting that the stromal cells also had significant albeit slower metabolic activity presumably to support tumor growth. (See e.g., graphs shown in FIG. 9D). Therefore, the exemplary DO-SRS can visualize the heterogeneity of metabolism inside solid tumors with cellular resolution.

Example 11 Exemplary Discussion

The exemplary system, method, and computer-accessible medium, according to an exemplary embodiment of the present disclosure, can utilize the exemplary DO-SRS as a nondestructive, noninvasive, and background-free imaging method that can be used to visualize metabolic dynamics of proteins, lipids, and DNA in a variety of model organisms. The exemplary DO-SRS can facilitate in situ visualization of de novo lipogenesis and protein synthesis in animals at an unprecedentedly low cost and without tissue bias, representing beneficial technical advance. In particular, the ability to simultaneously image newly synthesized lipids and proteins facilitated new insights into the metabolic basis of several biological processes.

The exemplary system, method, and computer-accessible medium, according to an exemplary embodiment of the present disclosure, can utilize $D_2O$, which can be a superior probe to deuterium-labeled carbon substrate in monitoring and imaging metabolic activities, because $D_2O$ does not perturb native metabolism, can freely diffuse into cells, and can be a non-carbon tracer that can probe de novo biosynthesis. For visualizing lipogenic activities, it was shown that $D_2O$ can be superior to D-FAs and also expect $D_2O$ to be superior to previously used D-glucose (see, e.g., Reference 52), which can create hyperglycemia when used at high concentration and may not label newly synthesized lipids as efficient as $D_2O$ treatment.

The exemplary DO-SRS can be used to address a variety of biological questions. For example, when applied to heterogeneous tumor tissues, the exemplary DO-SRS can help identify cancer stem cells that have particular patterns of metabolic activities, such as high lipogenic activities. Label-free SRS was already used to find that ovarian cancer stem cells had significantly increased levels of unsaturated lipids than non-stem cancer cells (see, e.g., Reference 53), and the exemplary DO-SRS can be suited for those studies because of higher sensitivity and the ability to track metabolic dynamics. Another application can be to combine the exemplary DO-SRS with fluorescent labeling to monitor the metabolic activity of specific cells and lineages in situ. One particularly interesting problem can be the metabolic cooperation between glial cells and neurons. (See, e.g., Reference 54). In addition to the synthesis of lipids and proteins, the exemplary DO-SRS can also be used to monitor protein turnover, lipid consumption, and macromolecule degradation.

Although the exemplary DO-SRS can have relatively lower molecular specificity and sensitivity compared to mass spectrometry imaging ("MSI") methods (see, e.g., References 55-57), it can serve as a beneficial complementary approach to MSI methods because of several advantages. The exemplary DO-SRS provides straightforward and quantitative interpretation of total metabolic activities in three-dimensional living tissues, whereas all MSI procedures can be destructive surface analysis, involve more complicated computation than SRS imaging, and may not capture all D-labeled molecules equally due to certain bias towards easily ionized and desorbed analytes.

A major challenge for in vivo metabolic imaging can be the accessibility of tissues deep inside the body. Using devices similar to the coherent Raman scattering endoscopes (see, e.g., Reference 58), the exemplary DO-SRS can be applied to visualize metabolic patterns of internal organs and to evaluate tumor metabolism through optical biopsy. The recent development of high-speed, volumetric stimulated Raman projection ("SRP") microscopy and tomography (see, e.g., Reference 59) also can be used for deep-tissue, large-volume, in vivo imaging (e.g., imaging cortical metabolism). The sensitivity of the exemplary method can be high enough to operate in the range of low $D_2O$ enrichment that can be safe for humans. Given that SRS imaging has been demonstrated in humans before (see, e.g., Reference 60), the exemplary DO-SRS can have clinical application in tracking metabolic activities in humans.

Example 12: Spontaneous Raman Spectroscopy

Spontaneous Raman scattering spectra can be acquired on an upright confocal Raman microspectrometer (e.g., Xplora, Horiba Jobin Yvon) with 532 nm diode laser source and 1800 l/mm grating at room temperature. The excitation power can be approximately 40 mW after passing through a 50× air objective (e.g., XLPlan N, 0.75 N.A., Olympus), and 40 s acquisition time accumulated by 22 was used to collect Raman spectra of all samples at a single point under identical conditions. For cultured cells, the Raman background of water and cover glass can be removed from all cell spectra by subtracting the signal at empty space from the signals collected from cells.

Exemplary Stimulated Raman Scattering Microscopy

An inverted laser-scanning microscope (e.g., FV1200 MPE, Olympus) optimized for near-IR throughput and a 25× water objective (e.g., XLPlan N, 1.05 N.A., MP, Olympus) with high near-LR transmission for SRS imaging was utilized. A picoEMERALD system (e.g., Applied Physics & Electronics) supplied synchronized pulse pump beam (e.g., with, approximately, tunable 720-990 nm wavelength, 5-6 ps pulse width, and 80-MHz repetition rate) and Stokes (e.g., with fixed wavelength at about 1064 nm, approximately 6 ps pulse width, and approximately 80 MHz repetition rate). Stokes can be modulated at 8 MHz by an electronic optic modulator. Transmission of the forward-going Pump and Stokes beams after passing through the samples was collected by a high N.A. oil condenser (e.g., N.A.=1.4). A high O.D. bandpass filter (e.g., 890/220, Chroma) can be used to block the Stokes beam completely and to transmit the pump beam only onto a large area Si photodiode for the detection of the stimulated Raman loss signal. The output current from the photodiode can be terminated, filtered, and demodulated by a lock-in amplifier at 8 MHz to ensure shot-noise-limited detection sensitivity. The demodulated signal can be fed into analog channel of FV1200 software FluoView 4.1a (e.g., Olympus) to form image during laser scanning.

Exemplary Image Acquisition Parameters

To acquire CD signals, the OPO laser power for the pump beam was set to 100 mW and the IR laser power for the Stokes beam at 150 mW for all experiments except the *C. elegans* experiments in FIG. 12, for which the OPO laser was set to about 50 mW and the IR laser at 100 mW. To acquire CH signals, the OPO laser was set to about 100 mW and IR laser at 150 mW except for all *C. elegans* experiments, for which the OPO laser was set to 50 mW and IR laser at about 100 mW. The bias voltage of the photodiode detecting the SRS signal was kept the same as 64 volts for all experiments.

Exemplary Cell Culture and Imaging

HeLa (e.g., ATCC CCL-2), COS-7 (e.g., ATCC CRL-1651), and U-87 MG (e.g., ATCC HTB-14) cells were obtained from ATCC (e.g., Manassas, VA) and cultured in Dulbecco's modified Eagle's medium ("DMEM", Thermo Fisher) supplemented with 10% fetal bovine serum (e.g., Thermo Fisher) in a humidified 5% $CO_2$ atmosphere at 37° C. LS174T (e.g., ATCC CL-188) was also obtained from ATCC and cultured in Eagle's Minimum Essential Medium (e.g., EMEM from ATCC). To make cell culture medium containing $D_2O$, a mixture of $D_2O$ (e.g., Sigma-Aldrich, Cat. 151882) and distilled $H_2O$ to dissolve DMEM powder (e.g., Sigma) was used and the medium was sterilized by filtering.

For live-cell imaging, HeLa and COS-7 cells were seeded onto a glass-bottom dish (e.g., MatTek) and grown for 6 to 8 hours in regular DMEM before the medium was changed to DMEM containing 70% $D_2O$. Cells were then grown for different periods of time before being placed onto the stage for SRS imaging. When treating cells with D-labeled fatty acids, they were first reacted with sodium hydroxide and then coupled to bovine serum albumin ("BSA") in about 2:1 molar ratio to make 2 mM stock solution. Those stock solutions were then added to the medium to reach the final working concentration (e.g., 10 μM).

To determine cellular toxicity, HeLa cells and COS-7 cells were first seeded in %9-well plates at about 500 per $cm^2$ and grown overnight; the culture was then changed to DMEM containing different concentration (e.g., 0% to 100%) of $D_2O$ for about 48 hours. The viability of cell was accessed using the CellTiter-Glo® Luminescent Cell Viability Assay (e.g., Promega) according to the manufacturer's protocol. Cells cultured in pure DMEM medium were used as control and wells containing only medium without cells for background luminescence. Viability was calculated using the background-corrected absorbance as follows: Viability (%)=Absorbance of experiment well/Absorbance of control well×100%. Three replicates were performed.

Exemplary Treatment of Inhibitors

For inhibitor treatments, cells were first grown in glass bottom dishes with DMEM made of $H_2O$ overnight, and then the medium was changed to 70% $D_2O$ DMEM containing either 10 nM fatty acid synthase inhibitor TVB-3166 (e.g., Sigma CAS 1533438-83-3) or 1 μM protein synthesis inhibitor anisomycin (e.g., Sigma CAS 22862-76-6). Cells were then cultured for 24 hours, imaged by SRS microscopy, and fixed by 4% paraformaldehyde for spontaneous Raman spectroscopy.

Methanol wash was performed on fixed cells in glass-bottom dishes and tissues with 99.9% methanol (e.g., Sigma) for 30 minutes and 24 hours, respectively, followed by phosphate buffered saline ("PBS") wash. For proteinase K treatment, tissues were first fixed by paraformaldehyde and then treated with 0.2 mg/ml recombinant proteinase K (e.g., Roche) at 37° C. for 15 minutes and subsequently, washed with PBS. Three replicates were performed for those experiments.

Exemplary Biochemical Extraction of Macromolecules

To extract lipids, HeLa cells were grown in DMEM with 70% $D_2O$ for 24 hours, fixed with 4% paraformaldehyde, washed with PBS in petri dishes, and then harvested into 15-mL falcon tubes. Approximately 1.3 mL of chloroform and 2.7 mL of methanol were then added to the cells to extract lipids. After centrifugation at about 1377×g for 5 minutes, the supernatant was transferred to a clean tube. Subsequently, mL of 50 mM citric acid, 2 mL of water, and 1 mL of chloroform were added to the solution and vigorous shaking was used to mix the content. Liquid phases were then separated by centrifugation at 1377×g for 10 minutes and the lower phase containing the lipids were transferred to a clean tube. Caps were kept open to facilitate the evaporation of solvent and the concentration of lipids.

Proteins and DNA were extracted using Trizol (e.g., catalog #15596026, Life Technologies) and DNAzol (e.g., catalog #10503027, Thermo Fisher Scientific), respectively, according to the manuals provided by the manufacturer.

Exemplary *C. elegans* Experiments

*C. elegans* wild type (e.g., N2) and mutant strains were maintained at 20° C. using nematode growth media ("NGM") and *E. coli* strain OP50 as a food source. (See. e.g., Reference 61). Different concentrations of $D_2O$ were added to replace $H_2O$ in NGM. *E. coli* OP50 were seeded on $D_2O$-containing NGM plates and grown for 24 hours; worms were then placed at different ages onto those plates for various amount of time. To determine the toxicity of $D_2O$, eggs were prepared using hypochlorite, which made the eggshell porous and permeable to $D_2O$, placed them onto plates containing different concentration of $D_2O$, and counted the number of eggs that could not hatch into normal moving larva. Fourth stage larva were placed onto those plates and counted how many animals became sterile and determined the brood size by counting the total number of hatch larvae from the all the eggs laid by one animal. Three replicates were performed.

To prevent deuterium labeling of the bacteria and to feed worms with non-labeled bacteria on $D_2O$ plates, the OP50 bacteria (e.g., grown in H O) were killed after placing them onto $D_2O$ plates with UV light. Worms grown on dead non-labeled bacteria developed normally and had similar level of $CH_2$ and $CH_3$ signal, compared to the controls fed on bacteria that grew on $D_2O$ plates for at least 24 hours.

To supplement deuterated fatty acids to worms, OP50 bacterial culture was mixed well with 4 mM D31-palmitic acid and then seeded onto NGM plates that contained 100% $H_2O$. As controls, the same OP50 bacteria culture were seeded onto NGM plates that contained 20% $D_2O$. 24 hours later, eggs were placed onto those plates and grew until L4 stage before being imaged.

Regular SRS imaging was performed after animal fixation with 4% formaldehyde for 30 minutes and washing with PBS. Live imaging was performed by directly transferring animals from $D_2O$ plates onto a 4% agarose pad and mounting them in M9 solution containing 0.1 µm polystyrene beads (e.g., Polysciences, Inc.) to reduce mobility. For most *C. elegans* experiments, at least 8 animals were imaged for each condition, and Student's t-test was used to identify any significant difference between two treatment groups. No randomization was applied, and the authors were not blinded to the experimental groups.

Exemplary Metabolic Activity Tracking in Zebrafish Embryos

Zebrafish embryos carrying the fluorescent reporters Tg(kdrl:EGFP) (see, e.g., Reference 47) were incubated in egg water (see, e.g., Reference 62) supplemented with about 20% $D_2O$ for 24 or 48 hours from 1-cell stage at about 28.5° C., For $D_2O$ probing from 24 to 36 hpf and from 34 to 48 hpf, embryos were transferred from 100% $H_2O$ environment to egg water containing 20% $D_2O$. After the incubation, embryos were manually dichlorinated and fixed in 4% PFA overnight at 4° C. Following fixation, the embryos were transferred to PBS prior to imaging. At least four embryos were imaged for each condition. The zebrafish work was approved by the IACUC (e.g., Institutional Animal Care and Use Committee at Columbia University) under protocol AC-AAAJ7554 for ethical regulation.

Exemplary $D_2O$ Probing in Mice

Wild-type approximately 3 to approximately 4 month old adult C57BL/6J and ob/ob (B6.Cg-Lep$^{ob}$/J) mice were both obtained from the Jackson Laboratory and were maintained and bred at Columbia University animal facility. For the ex vivo mice tissue experiments, mice that drank about 25% $D_2O$ for certain days were anesthetized with isoflurane and sacrificed. Various organs and tissues were harvested, fixed with 4% formaldehyde overnight, and then cut into slices of 120 µm thickness using a vibrating blade microtome (e.g., Vibratome, Leica) for SRS imaging. For the in vivo SRS imaging of ear skin, mice were kept anesthetized with isoflurane while one ear was gently sandwiched between a cover slip and a glass slide, which was then placed onto the imaging stage with a heating pad that keep the body warm during the imaging session. For all mice experiments, three mice were used for each condition, and at least three different fields of each tissue were imaged. No randomization was applied, and the authors were not blinded to the experimental groups.

To establish glioblastoma xenograft, intracranial implantation of U-87 MG human glioma cells in nude mice (e.g., J:NU) were performed. The mouse was anesthetized and positioned in stereotaxic instrument (e.g., David Kopf Instruments), and then a small section (e.g., 2 mm in diameter) of the skull can be ground with a dental drill until it became soft and translucent. Subsequently, $1.5 \times 10^5$ U87-MG tumor cells (e.g., in 3 µl) were injected into the frontal region of the cerebral cortex over the course of 5 minutes using a 1.5 mm glass capillary. After the implantation, mouse head skin can then be closed with SILK sutures (e.g., Harvard Apparatus). Two weeks later, mice bearing glioblastoma started and were kept on drinking 25% $D_2O$ for 15 days before being sacrificed for tumor imaging. For the colon tumor xenograft, subcutaneously $1 \times 10^7$ human colorectal LS174T cells were injected into the lower flank of nude mouse. Ten days later, tumor bearing mice were treated with 25% $D_2O$ as drinking water for 3 or 15 days before being sacrificed for tumor SRS imaging. The experimental protocols for the mouse studies all complied with ethical regulations and were approved by IACUC under the protocol AC-AAAQ0496.

Exemplary Feeding and Injection of D-AAs and D-FAs

To feed mice with D-labeled amino acids ("D-AAs"). D-AA mixture (e.g., Catalog #DLM-6819-1, Cambridge Isotope Laboratory) were dissolved in drinking water at about 2 mg/ml, and adult mice drank approximately 4 ml of the water every day for 8 days before their organs were harvested for SRS imaging. To inject D-AAs into the bloodstream via carotid artery, mice were anesthetized and kept warm on a heating pad. Neck skin of the mouse was cleaned with 2% chlorhexidine solution followed by 70% isopropyl alcohol and the planned incision area was infiltrated subcutaneously with a 1:10 dilution of 50/50 lidocaine (e.g., 1%). An approximately 2 cm incision was made along the midline region of the throat to expose the common carotid artery, which was then tied with suture thread (e.g., Prolene 86979 Ethicon) on the side closer to heart to stop the blood flow. The artery was then cut with precision stainless micro-scissor (e.g., 63041-984, VWR), and a polyurethane based Micro-Renathane catheter tube (e.g., MRE033, Braintree Scientific, INC.) was carefully cannulated into the opening of carotid artery. (See. e.g., Reference 63). A syringe filled with 80 mg/ml D-labeled amino acids dissolved in mammalian Ringer solution was then connected with the cannulated tubing, and liquid flow was controlled by a syringe pump (e.g., AL-1000, WPI) to inject the solution at 0.01 mL/min perfusion rate for half an hour each session for about 2.5 days with a time interval of about 2 hours.

To inject D-labeled palmitic acids ("D-Pas") intravenously, mice were anesthetized by isoflurane, and one of the carotid arteries was cannulated for the implantation of a catheter. A syringe filled with 4 mM D-PA dissolved in mammalian Ringer's solution was then connected with the implanted catheter, and D-PA solution was perfused at 0.001 ml/min using a syringe pump (e.g., AL-1000, WPI). The administration lasted for 8 hours every day for three consecutive days before the mice were sacrificed and their organs were harvested, fixed, sectioned, and imaged by SRS.

To inject D-PA intraperitoneally, 0.16 ml of 600 mM D-PA emulsion was injected into the lower right side of abdomen according to a previous method. (See, e.g., Reference 64). 17 hours later, the mice were sacrificed and their tissues were collected and imaged.

Exemplary $CD_L/CD_P/C_{DNA}$ Three-Component Un-Mixing

Three-component un-mixing of $CH_L/CH_P/CH_{DNA}$ signals were previously reported. (See, e.g., Reference 24). A similar method to unmix CD signals can be used. SRS signals were acquired from 2135 cm$^{-1}$, 2185 cm$^{-1}$, and 2210 cm$^{-1}$ bearing the intrinsic features of lipids, proteins, and DNA, respectively, and then used a linear combination of the three signals with coefficients to determine the amount of the three macromolecules. The signals at 2135 cm$^{-1}$ ($I_{2135}$), 2185 cm$^4$ ($I_{2185}$), and 2210 cm$^{-1}$ ($I_{2210}$) can be a linear combination of lipid, protein, and DNA concentrations ($CD_L$, $CD_P$, and $CD_{DNA}$) with coefficients $a_L$, $a_P$, $a_{DNA}$, $b_L$, $b_P$, $b_{DNA}$, $c_L$, $c_P$, and $c_{DNA}$ as shown in Eq. 1.

$$\begin{pmatrix} I_{2135} \\ I_{2185} \\ I_{2210} \end{pmatrix} = \begin{pmatrix} a_L & a_P & a_{DNA} \\ b_L & b_P & b_{DNA} \\ c_L & c_P & c_{DNA} \end{pmatrix} \begin{pmatrix} CD_L \\ CD_P \\ CD_{DNA} \end{pmatrix} \quad (1)$$

Un-mixing coefficients were obtained from the spectra of D-labeled cellular extracts from $D_2O$-treated HeLa cells (e.g., see FIG. 11A), $a_L$, $b_P$, and $c_{DNA}$ were set to 1, and the rest coefficients were scaled to their relative values. Substitute the coefficients with their values, Eq. 2, for example, as the following.

$$\begin{pmatrix} I_{2135} \\ I_{2185} \\ I_{2210} \end{pmatrix} = \begin{pmatrix} 1 & 0.38 & 0.29 \\ 0.48 & 1 & 1.08 \\ 0.24 & 0.71 & 1 \end{pmatrix} \begin{pmatrix} CD_L \\ CD_P \\ CD_{DNA} \end{pmatrix} \quad (2)$$

From Eq. 2, $CD_L$, $CD_P$, and $CD_{DNA}$ were derived as the unmixed D-labeled lipid, protein, and DNA signal intensity, respectively, using Eq. 3.

$$\begin{pmatrix} CD_L \\ CD_P \\ CD_{DNA} \end{pmatrix} = \begin{pmatrix} 1.31 & -0.98 & 0.67 \\ -1.24 & 5.21 & -5.27 \\ 0.56 & -3.47 & 4.58 \end{pmatrix} \begin{pmatrix} I_{2135} \\ I_{2185} \\ I_{2210} \end{pmatrix} \quad (3)$$

Exemplary $CD_L/CD_P$ Un-mixing

Since unmixed CDDNA signal can be very weak in non-dividing cells in most of the tissues imaged, a simplified un-mixing procedure was developed that focused on separating $CD_L$ and $CD_P$ signals. The three-component un-mixing equation was simplified, and the $CD_{DNA}$ variable was removed to obtain Eqs. 4 and 5, from which the unmixed D-labeled lipid and protein signals were derived using Eqs. 6 and 7.

$$I_{2135} = a_L \cdot CD_L + a_P \cdot CD_P \quad (4)$$

$$I_{2185} = b_L \cdot CD_L + b_P \cdot CD_P \quad (5)$$

$$CD_L = \frac{a_P \cdot I_{2185} - b_P \cdot I_{2135}}{a_P \cdot b_L - a_L \cdot b_P} \quad (6)$$

$$CD_P = \frac{b_L \cdot I_{2135} - a_L \cdot I_{2185}}{a_P \cdot b_L - a_L \cdot b_P} \quad (7)$$

For $CD_L/CD_P$ un-mixing, the spectra of in situ CD lipid and protein signals were used to measure the coefficients. From the spontaneous Raman spectra of pure D-labeled protein signal (e.g., signals after 24-hour methanol wash) and pure D-labeled lipid signal (e.g., signals removed by methanol wash-subtracting methanol-resistant signal from total signal). All signals were first normalized to the phenylalanine peak at 1004 cm$^{-1}$, which stayed constant during methanol wash, and then normalized to the peaks of pure protein and lipid signals, respectively (e.g., see FIGS. 11A-11F). Thus, $a_L$ and by were set to 1; the relative intensity of protein bleed-through signal in the lipid channel ($a_P$) and the relative intensity of lipid bleed-through signal in the protein channel ($b_L$) were measured on the spectra. For example, in xenograft tumor tissues (e.g., see FIG. 11C), $a_L=1$, $a_P=0.40$, $b_L=0.51$, and $b_P=1$.

Thus, the un-mixing Eqs. 8 and 9 for tumor tissues.

$$CD_L = 1.25 \cdot I_{2135} - 0.50 \cdot I_{2185} \quad (8)$$

$$CD_P = 1.25 \cdot I_{2185} - 0.64 \cdot I_{2135} \quad (9)$$

Using the same method, pure D-labeled protein and lipid signals were obtained from the mouse pancreas and brain tissues and calculated their specific un-mixing coefficients. Data from the three types of tissues were combined to generate a set of average coefficients: $a_L=1$, $a_P=0.48\pm0.17$, $b_L=0.42\pm0.07$, and $b_P=1$.

Among the multiple tissues analyzed, the CD lipid spectrum showed a consistent shape, but CD protein had varying levels of bleed-through into $CD_L$ channel across different tissue types (e.g., see FIG. 13C), which possibly resulted from tissue-specific incorporation of deuterium into various NEAAs and/or different NEAA composition of D-labeled proteins. One extreme example can be the pyramidal neurons: their cell body showed almost no SRS signal at about 2135 cm$^{-1}$ but strong signal at 2185 cm$^{-1}$, suggesting almost no protein bleed-through into $CD_L$ channel. Thus, when applying the un-mixing procedure to cells and tissues previously uncharacterized, $a_P$ was tested from approximately 0.31 to approximately 0.65 until the nucleus was deprived of $CD_L$ signal after un-mixing. The following equations were used for $CD_L/CD_P$ signal un-mixing of different tissues.

|  | $CD_L$ un-mixing | $CD_P$ un-mixing |
|---|---|---|
| Cos-7 and HeLa cells | $CD_L = 1.25 \cdot I_{2135} - 0.39 \cdot I_{2185}$ | $CD_P = 1.25 \cdot I_{2185} - 0.52 \cdot I_{2135}$ |
| Glioblastoma and Colon tumor xenograft | $CD_L = 1.25 \cdot I_{2135} - 0.50 \cdot I_{2185}$ | $CD_P = 1.25 \cdot I_{2185} - 0.64 \cdot I_{2135}$ |
| Zebrafish tissues | $CD_L = 1.25 \cdot I_{2135} - 0.50 \cdot I_{2185}$ | $CD_P = 1.25 \cdot I_{2185} - 0.52 \cdot I_{2135}$ |
| C. elegans | $CD_L = 1.25 \cdot I_{2135} - 0.70 \cdot I_{2185}$ | $CD_P = 1.25 \cdot I_{2185} - 0.52 \cdot I_{2135}$ |
| Mouse sebaceous glands and adipose tissues | $CD_L = 1.25 \cdot I_{2135} - 0.39 \cdot I_{2185}$ | $CD_P = 1.25 \cdot I_{2185} - 0.81 \cdot I_{2135}$ |

|  | $CD_L$ un-mixing | $CD_P$ un-mixing |
|---|---|---|
| Mouse internal capsule and cortex | $CD_L = 1.25 \cdot I_{2135} - 0.39 \cdot I_{2185}$ | $CD_P = 1.25 \cdot I_{2185} - 0.70 \cdot I_{2135}$ |
| Mouse liver, pancreas, and muscle tissues | $CD_L = 1.25 \cdot I_{2135} - 0.35 \cdot I_{2185}$ | $CD_P = 1.25 \cdot I_{2185} - 0.60 \cdot I_{2135}$ |

Exemplary $CH_L/CH_P$ Un-Mixing

To uunix $CH_L$ lipid and $CH_P$ protein signals, a previously reported spectral linear combination procedure was adapted. (See, e.g., Reference 22). The SRS signals were acquired at 2845 cm$^{-1}$ and 2940 cm$^{-1}$, which bear the vibrational features of C—H bonds in lipids and proteins, respectively. The amount of lipids and proteins can then be determined by a linear combination of the signals at those two wavenumbers, with coefficients predetermined by pure substances. (See. e.g., Reference 22). Equation 10 and 11 were used to calculate unmixed $CH_L$ and $CH_P$ signals. $I_{2845}$ and $I_{2940}$ can be SRS signal intensities at 2845 cm$^{-1}$ and 2940 cm$^{-1}$, respectively.

$$CH_L = I_{2940} - I_{2845} \quad (10)$$

$$CH = 5 \cdot I_{2845} - 0.4 \cdot I_{2940} \quad (11)$$

Exemplary Image Processing

Olympus FluoView 4.1a scanning software was used to acquire images and ImageJ to assign color, calculate ratiometric values, and overlay images. All SRS images were generated by subtracting non-resonance background from the resonance signal. For the in vivo imaging of sebaceous glands in living mice (e.g., see FIG. 1D) the two-photon absorption by blood cells can be independent of the resonance state, and the fast dynamics of the signal in the blood flow distinguishes it from the more static SRS signal.

$CD_L/CH_L$ and $CD_P/CH_P$ ratios were used to show the proportion of newly synthesized lipids and proteins to total macromolecules, as an indication of relative metabolic rate. For example, $CD_L/CH_L$ ratio can be calculated using Eq. 12.

$$\frac{CD_L}{CH_L} = \frac{a*[C-D]}{b*[C-H]} = \frac{a*[\text{new lipid}]*G}{b*\left(\begin{array}{c}[\text{new lipid}]*\\(1-G)+[\text{old lipid}]\end{array}\right)} \quad (12)$$

[C-D] and [C—H] can be the concentrations of D-labeled and H-labeled lipids, respectively; a and b can be converting factors from lipid concentrations to SRS signal intensities; [old lipid] can be the amount of lipids that pre-existed before D$_2$O probing and remained at the time of imaging (e.g., not being degraded); [new lipid] can be the amount of newly synthesized lipids and G can be the proportion of D-labeled lipids to the newly synthesized lipids.

If [total lipid] can be defined as the amount of total lipids after the probing period and at the time of imaging, [total lipid]=[new lipid]+[old lipid], then Eq. 10 can be rewritten as Eq. 13.

$$\frac{CD_L}{CH_L} = \frac{a}{b} \cdot \frac{G}{\frac{[\text{total lipid}]}{[\text{new lipid}]} - G} \quad (13)$$

Since the upper limit of G can be approximately 0.2 (D$_2$O enrichment) in all the exemplary experiment, much smaller than [total lipid]/[new lipid], the $CD_L/CH_L$ can be approximated using Eq. 14.

$$\frac{CD_L}{CH_L} = \frac{a}{b} \cdot G \cdot \frac{[\text{new lipid}]}{[\text{total lipid}]} \quad (14)$$

Thus, $CD_L/CH_L$ can be linear to the proportion of the amount of newly synthesized lipids to total lipids and therefore a ratiometric measurement of lipid synthesis rate.

Figure 1B:
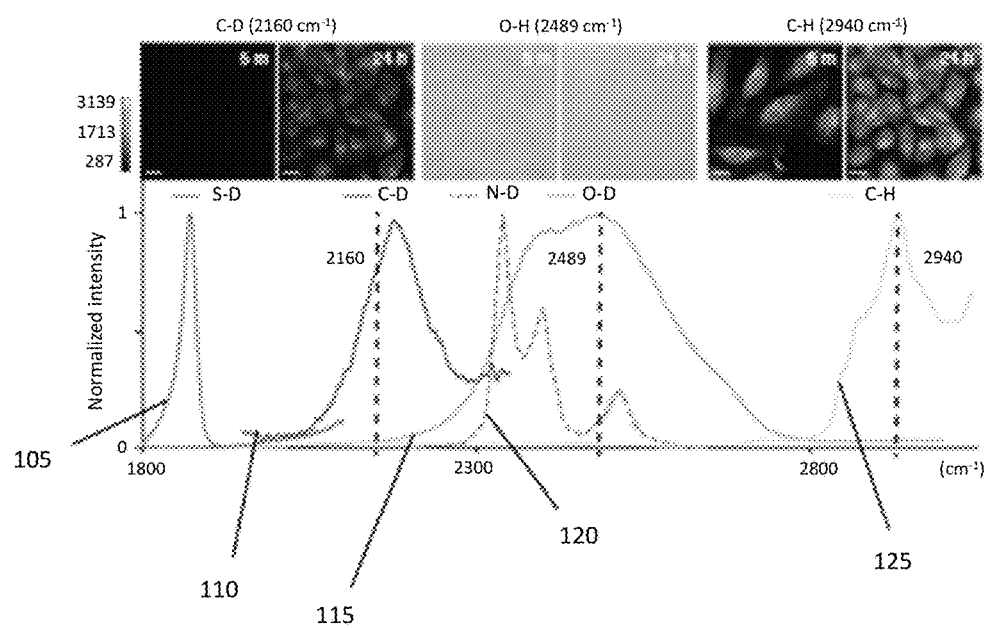
FIG. 1B is a set of exemplary images of various X-D bonds and associated graphs of peaks according to an exemplary embodiment of the present disclosure.

FIGS. 1A-1E illustrate SRS imaging of biosynthetic incorporation of deuterium from D$_2$O into macromolecules in living cells and animals. For example, FIG. 1A shows a molecular diagram of how D$_2$O-derived deuterium can form O-D, S-D, and N-D bonds through reversible non-enzymatic H/D exchange and be incorporated into C-D bonds of metabolic precursors for the synthesis of macromolecules through irreversible enzymatic incorporation. Note that under the condition of sparse labeling, the position of deuterium labeling on lipids is random, and this illustration only represents one possible labeling pattern. FIG. 1B shows a set of exemplary images and a graph of various X-D bonds produced Raman peaks at distinct positions. C-D spectrum 110, C—H spectrum 125, and O-D spectrum 115 were collected from HeLa cells grown in 70% D$_2$O medium, S-D spectrum 105 from saturated cysteine dissolved in D$_2$O, and N-D spectrum 120 adopted. (See, e.g., Reference 65). SRS images were collected for C-D, O-D, and C—H signal of HeLa cells at 5 minutes and 24 hours after adding D$_2$O-containing medium. FIG. 1C illustrates a set of images and a graph of signal-to-noise ratio (S/N; noise=1∝CV) for SRS signal of sebaceous glands at 2135 cm$^{-1}$ from mice that drank 4% or 25% D$_2$O for 8 days. Percentages of D$_2$O enrichment in body water are shown in parentheses. Detection limit at S/N=10 or 2 was calculated based on the linear relationship between average S/N and D$_2$O enrichment level. As shown in FIG. 1C, the linear relationship can be curve fitting and the concentration can be linearly related to the signal to noise ratio.

FIGS. 1D and 1E show ex images of frames from live SRS imaging recordings of the sebaceous glands under the ear skin of intact mice that drank 25% D$_2$O for 9 days and living fourth stage C. elegans larva that grew on 20% D$_2$O-containing NGM plates for 4 hours. The blood flow (arrows 135) in mouse visualized with two-photon absorption contrast and the movement of the C. elegans body (arrows 140) indicated that the animals under imaging were alive. Scale bar=20 µm. C-D signal was shown in LUT, and scale bars display the scale for the lookup table values.

Figure 2A:
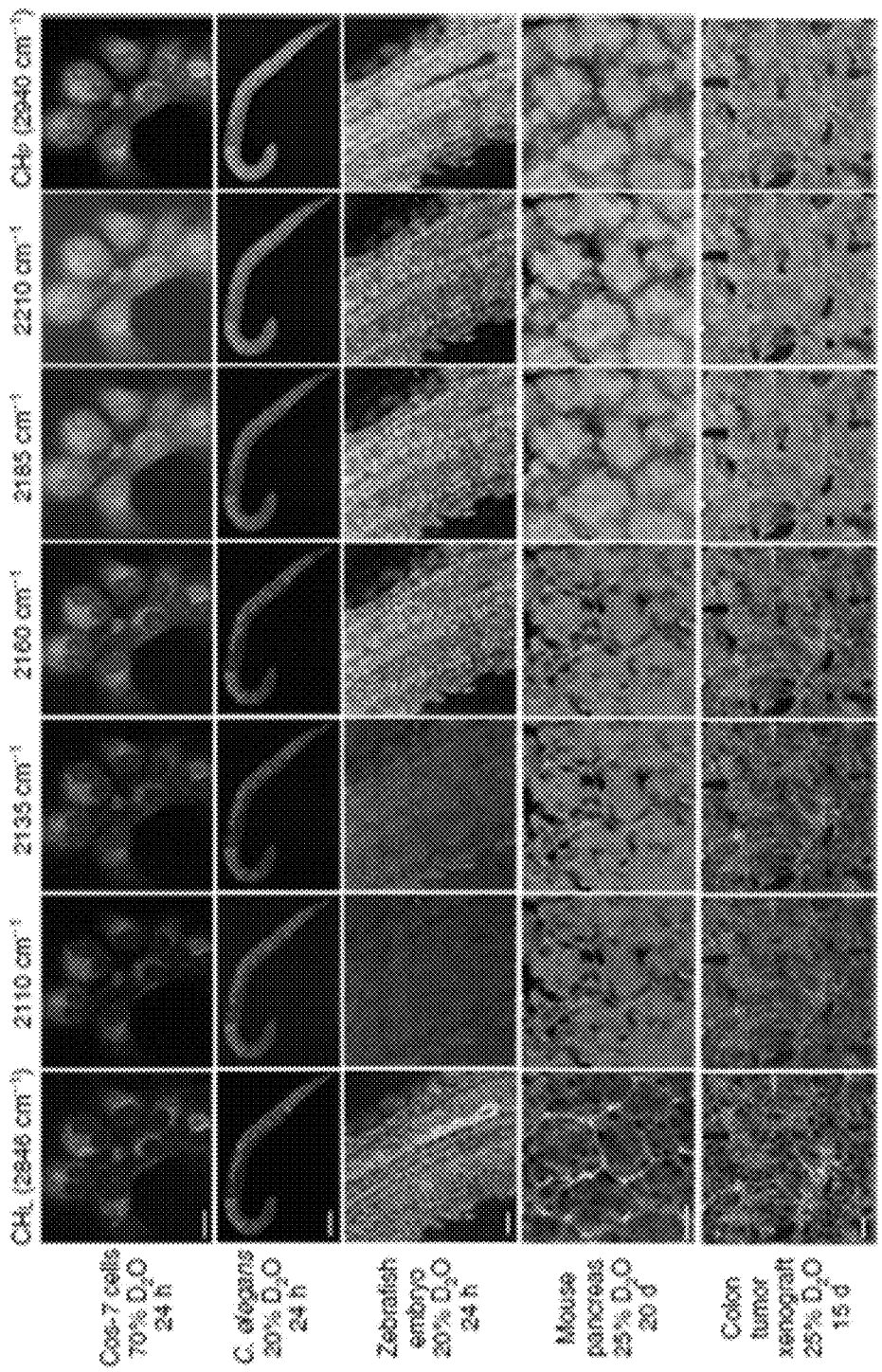
FIG. 2A is a set of SRS microscopic images of various cells and tissues treated with $D_2O$ according to an exemplary embodiment of the present disclosure.

FIGS. 2A-2G illustrate a set of exemplary images and graphs that show the identification of specific Raman shifts with macromolecular selectivity within the broad C-D vibrational spectra. In particular FIG. 2A shows a set of exemplary SRS images of various cells and tissues from animals treated with D$_2$O for indicated amounts of time. Images were collected using previously known Raman shifts for CH-containing lipids (e.g., $CH_L$ 2846 cm$^{-1}$) and proteins (e.g., $CH_P$ 2940 cm$^{-1}$) and five wavenumbers (e.g., 2110, 2135, 2160, 2185, and 2210 cm$^{-1}$) within the C-D broadband. Scale bar=20 µm.

Figure 2B:
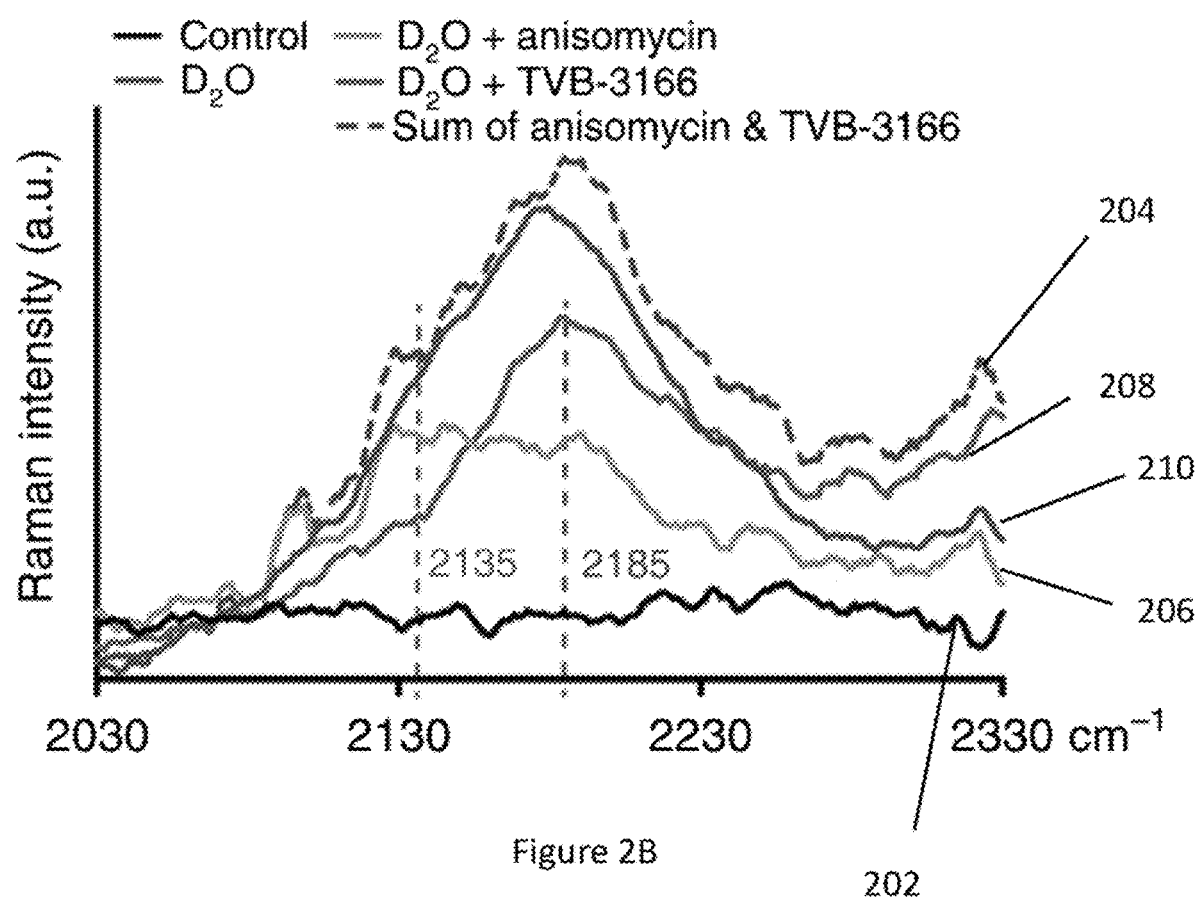
FIG. 2B is an exemplary graph of high wavenumber Raman spectra of HeLa cells according to an exemplary embodiment of the present disclosure.

FIG. 2B shows an exemplary graph that illustrates a high wavenumber Raman spectra (e.g., 2030 to 2330 cm$^{-1}$) of HeLa cells grown in DMEM made of 70% $D_2O$ (line 210) in the absence or presence of fatty acid synthase inhibitor TVB-3166 or protein synthesis inhibitor anisomycin. Cells grown in DMEM made of 100% $H_2O$ were used as control (line 202). Line 204 shows the sum of the values on lines 206 and 208.

Figure 2C:
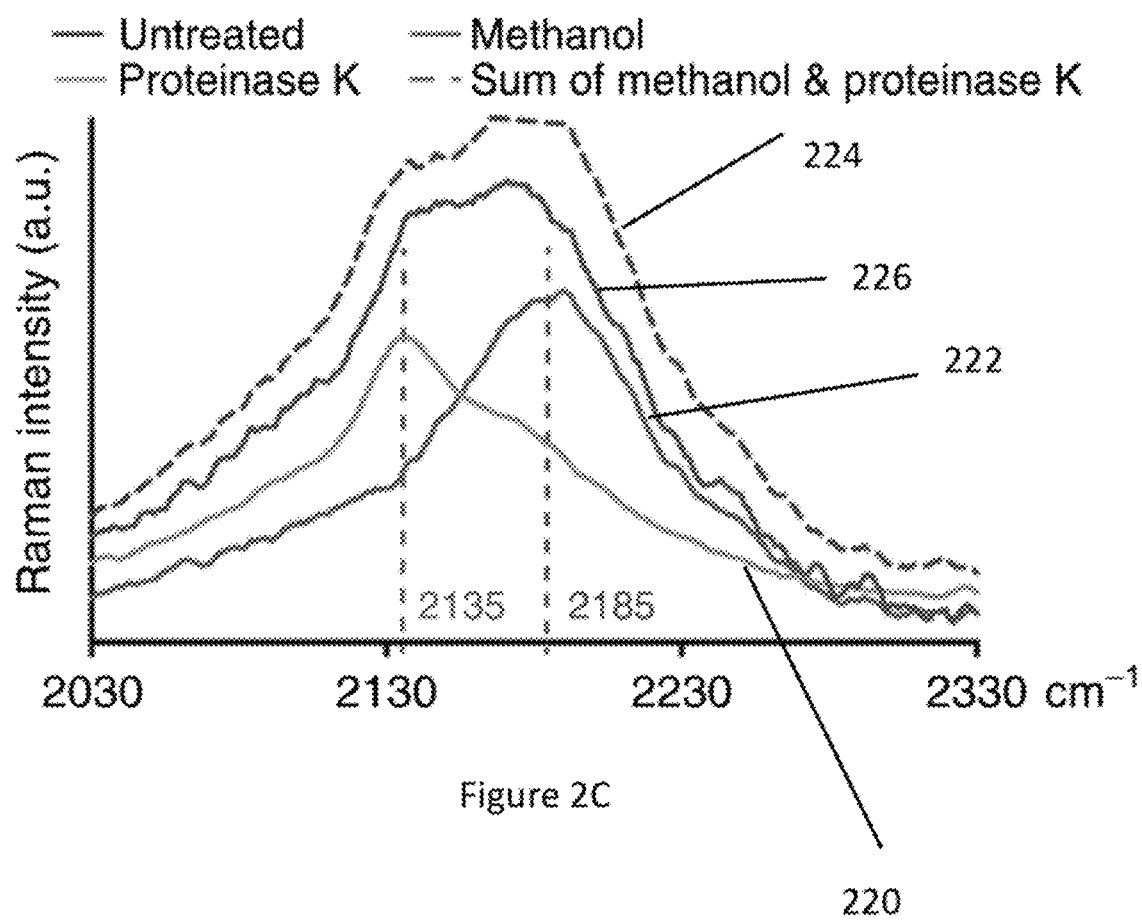
FIG. 2C is an exemplary graph of high wavenumber Raman spectra of deuterium-labeled xenograft colon tissue tumors according to an exemplary embodiment of the present disclosure.

FIG. 2C shows an exemplary graph that illustrates a high wavenumber Raman spectra of deuterium-labeled xenograft colon tumor tissues treated with protease K (line 220) or washed with methanol (line 222) for 24 hours, the sum of which is illustrated by line 224. Line 226 illustrates untreated tumor tissue. Mice bearing the xenograft drank 25% $D_2O$ as drinking water for 15 days before tumor tissues were harvested and imaged.

Figure 2D:
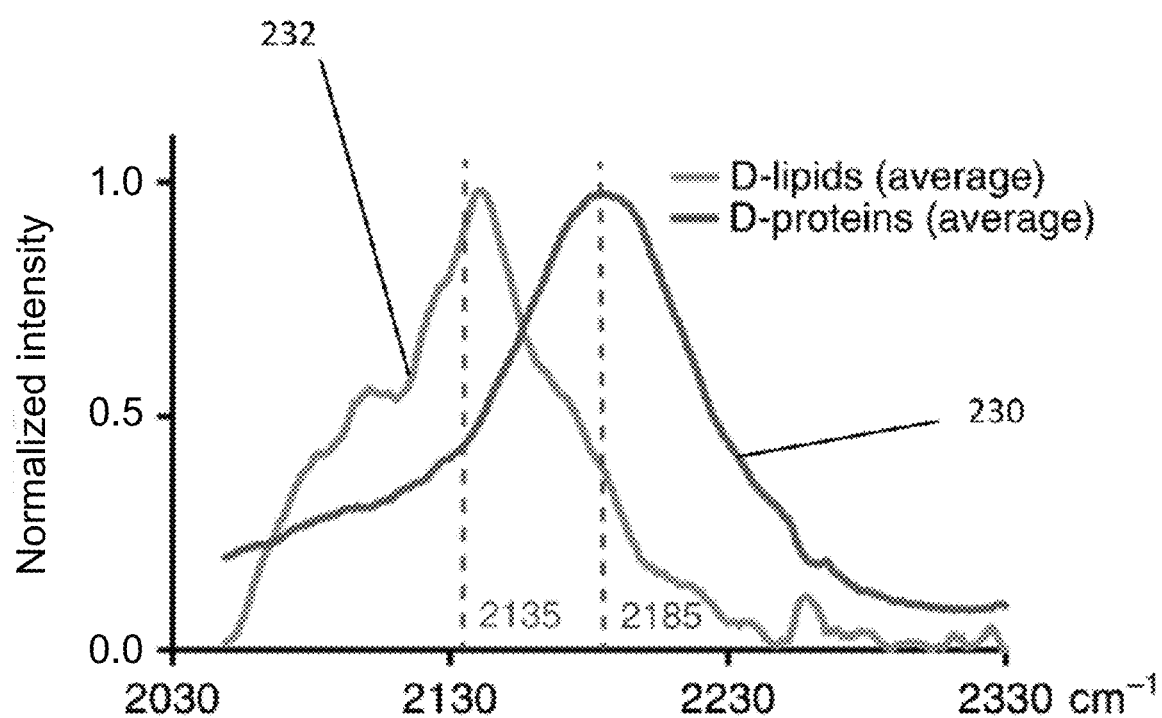
FIG. 2D is an exemplary graph of the normalized Raman spectra of tissue after a 24-hour Methanol wash according to an exemplary embodiment of the present disclosure.
Figure 2E:
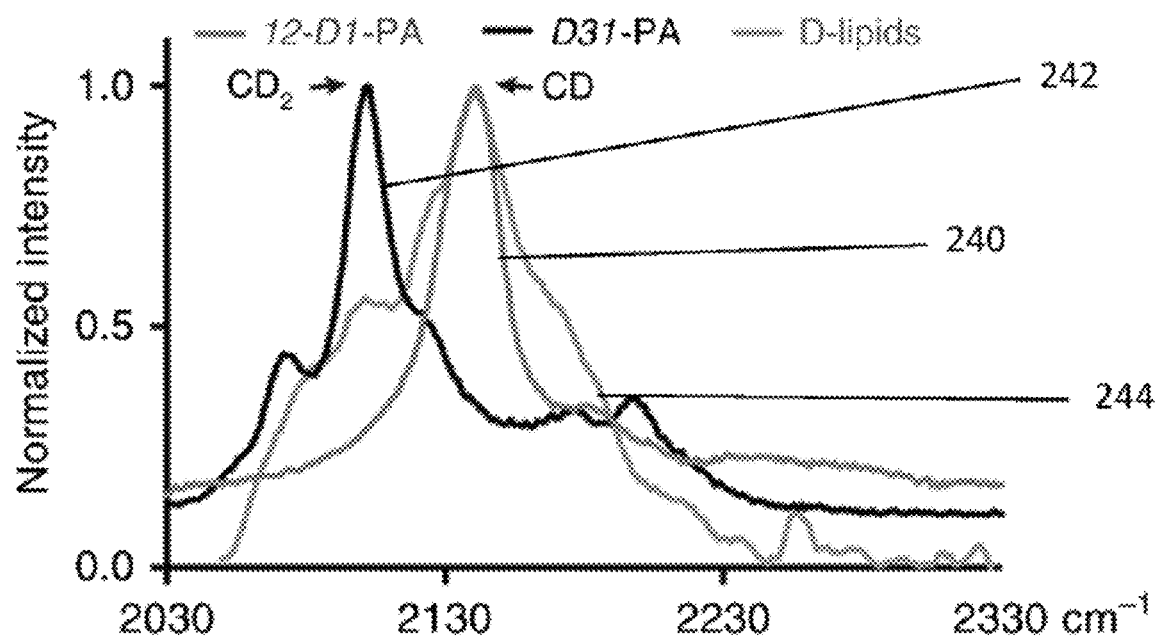
FIG. 2E is an exemplary graph of the comparison of Raman spectra of 12-D1-palmitic acid, D31-palmitic acid and in situ D-labeled standards according to an exemplary embodiment of the present disclosure.
Figure 2F:
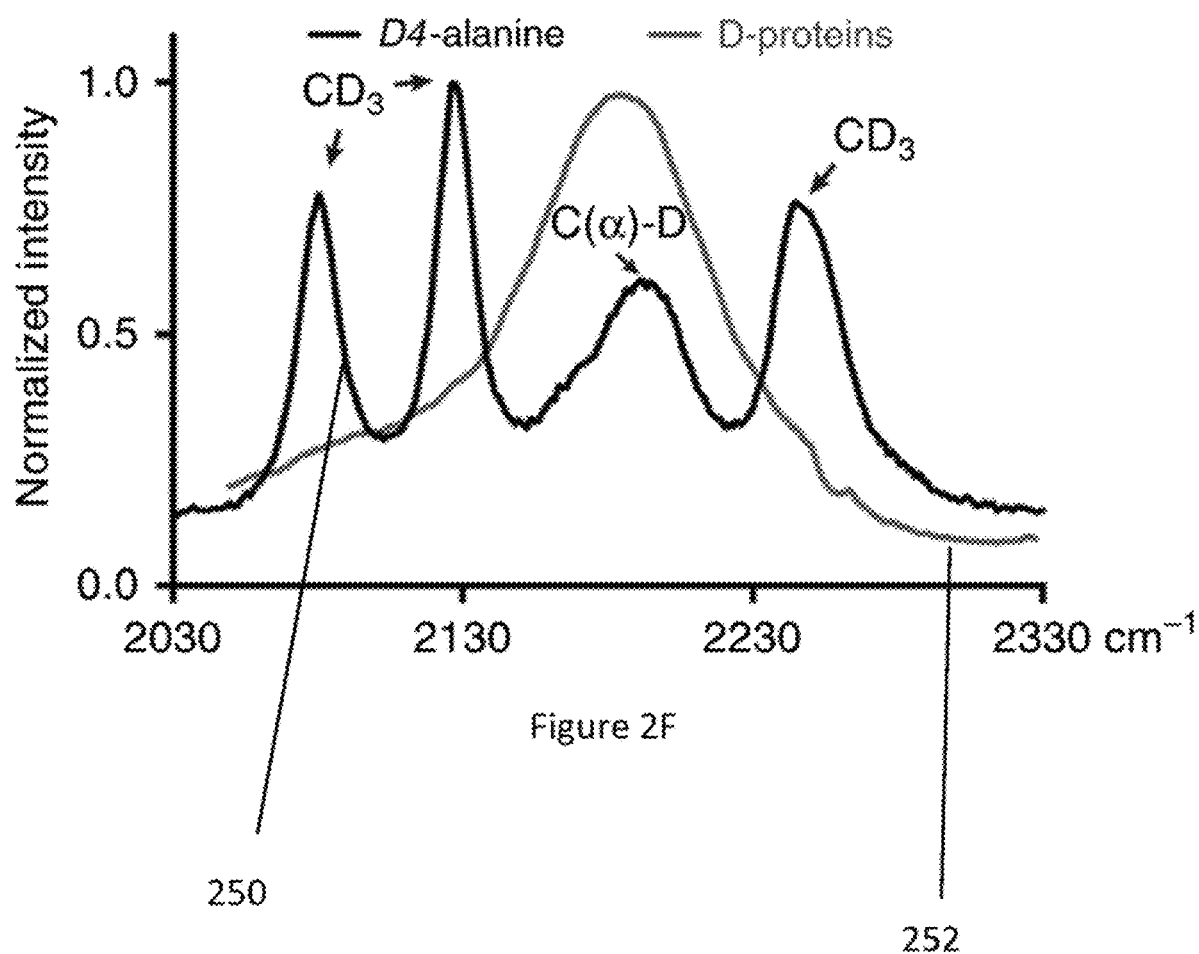
FIG. 2F is an exemplary graph of the comparison of Raman spectra of D4-alanine and D-labeled protein standards according to an exemplary embodiment of the present disclosure.
Figure 2G:
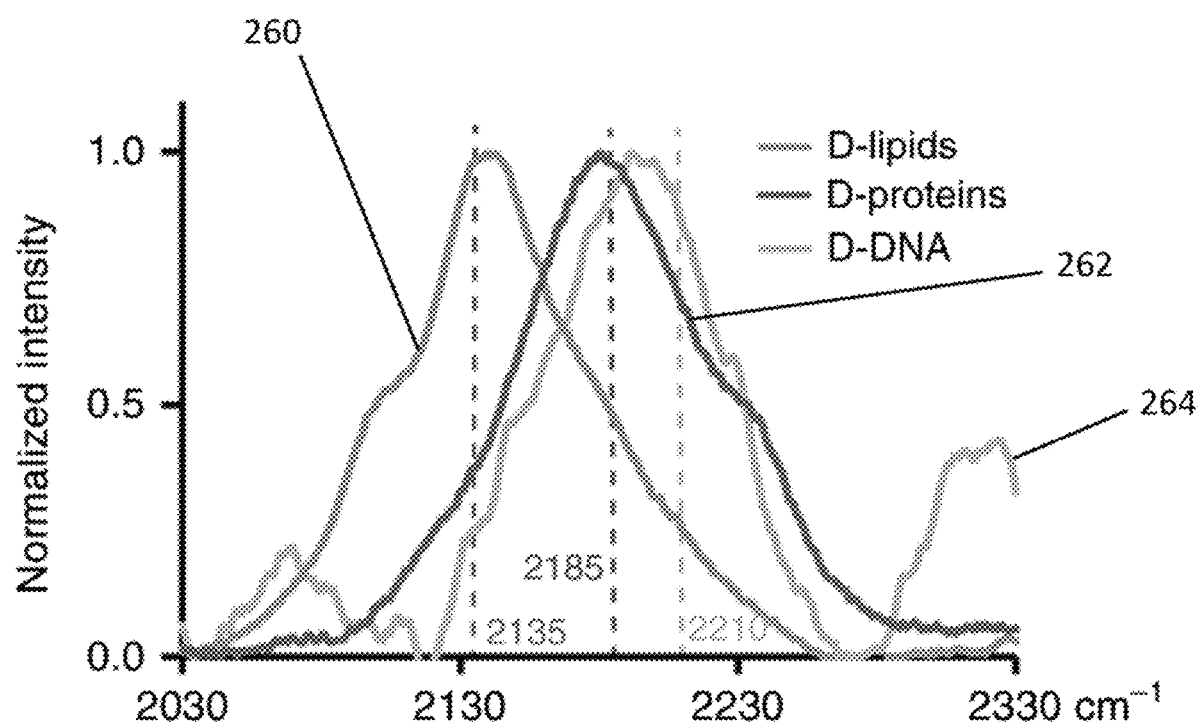
FIG. 2G is an exemplary graph of Raman spectra of biochemically extracted lipids, proteins and DNA from Hela cells according to an exemplary embodiment of the present disclosure.

FIG. 2D shows an exemplary graph that illustrates a normalized Raman spectra of tissue after 24-hour methanol wash (e.g., D-labeled protein signal 230) and the difference spectra before and after methanol wash (D-labeled lipid signal 232), averaged from various mouse tissues. FIG. 2E shows an exemplary graph that illustrates a comparison of Raman spectra of 12-D1-palmitic acid 240 (100 mM dissolved in DMSO), D31-palmitic acid 242 (100 mM in DMSO), and in situ D-labeled lipid standards 244. FIG. 2F shows an exemplary graph that illustrates a comparison of Raman spectra of D4-alanine 250 (100 mM in PBS), and D-labeled protein standards 252. Assignment of the peaks was made according to a previous report. (See. e.g., Reference 25). FIG. 2G shows an exemplary graph that illustrates a Raman spectra of biochemically extracted D-lipids 260, D-proteins 262, and D-DNA 264 from HeLa cells grown in DMEM media containing 70% $D_2O$.

Figure 3A:
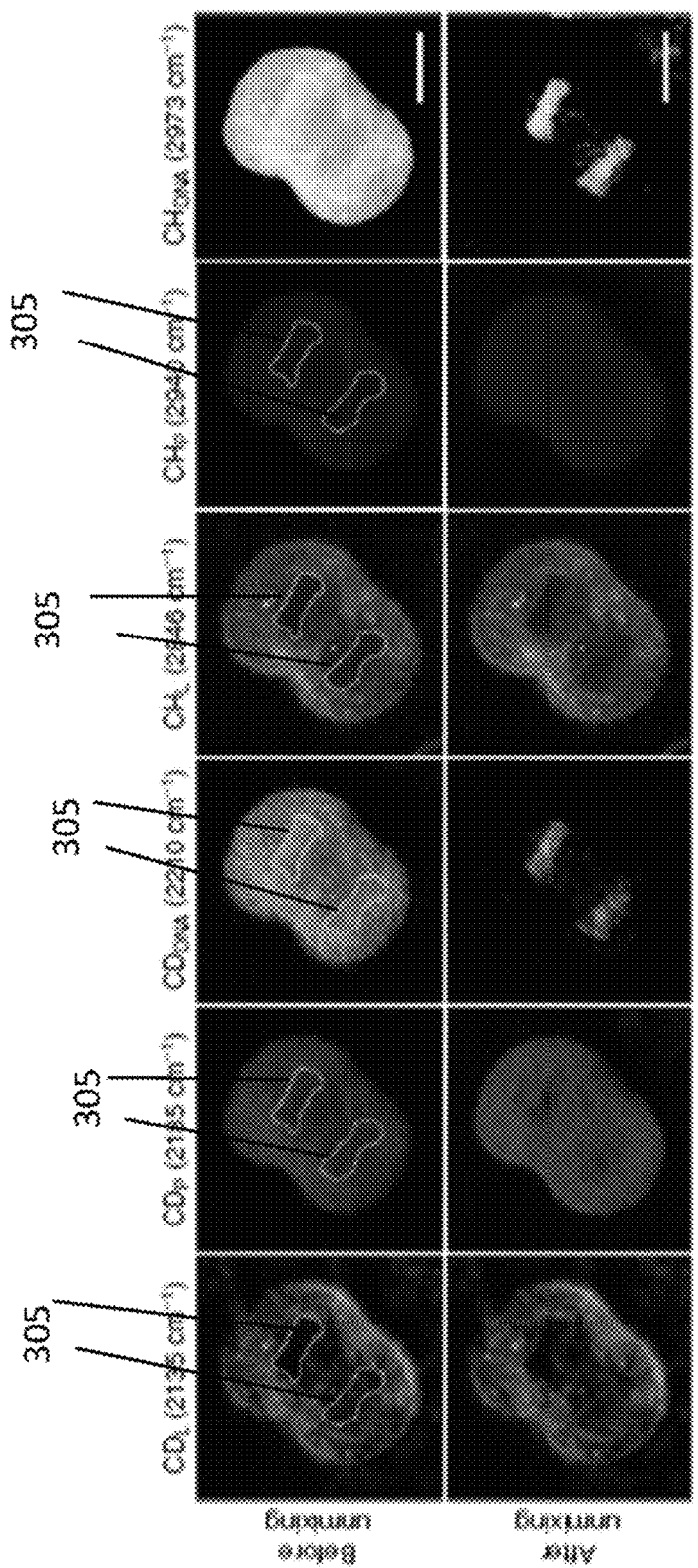
FIG. 3A is a set of exemplary images of the separation of CD protein and DNA signals according to an exemplary embodiment of the present disclosure.

FIGS. 3A-3E illustrate spectral un-mixing of D-labeled lipids, proteins, and DNA. FIG. 3A shows a set of exemplary images of the separation of CD protein and DNA signals via un-mixing in dividing cells. Outlines 305 enclose the nuclei. In all Figures, $CD_L$, $CD_P$, $C_{DNA}$, $CR_L$, $CH_P$, and $CH_{DNA}$ channels show signals collected at 2135, 2185, 2210, 2846, 2940, and 2973 cm$^{-1}$, respectively, and are color-coded in green, red, pink, yellow, blue, and gold respectively. FIG. 3B shows a set of exemplary SRS images, collected from the $CD_L$ and $CD_P$ channel, of COS-7 cells grown in 70% $D_2O$ DMEM for 24 hours and images of the same cells after methanol wash, with or without the application of un-mixing procedure. FIGS. 3C and 3D show exemplary graphs that illustrate a quantification of the mean SRS intensity (mean±s.d.) from $CD_L$ and $CD_P$ channels of COS-7 cells under various conditions before unmixing 310 and after un-mixing 315 (N=12 for each condition). Double asterisk indicates p<0.01 in an unpaired t-test. FIGS. 3E-3G illustrate exemplary sets of images before and after the application of $CD_L/CD_P$ un-mixing for COS-7 cells grown in 70% $D_2O$-containing DMEM for 24 hours (see e.g., FIG. 3E), xenograft colon tumor tissues from mice drinking 25% $D_2O$ for 15 days (see e.g., FIG. 3F), and sebaceous gland tissues from mice drinking 25% $D_2O$ for 3 days (see e.g., FIG. 3G). $CH_L/CH_P$ un-mixing was performed according to previous studies. (See, e.g., Reference 22). Scale bar 20 µm. Tissue-specific un-mixing parameters can be found in Methods.

Figure 4A:
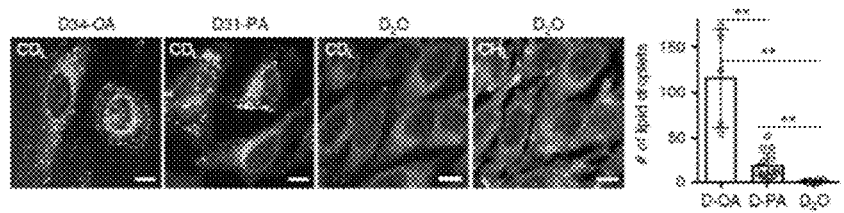
FIG. 4A is a set of exemplary images and an exemplary chart of SRS microscopic signals of HeLa cells according to an exemplary embodiment of the present disclosure.
Figure 4B:
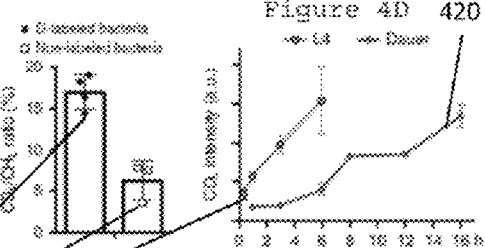
FIG. 4B is an exemplary chart of SRS microscopic signal intensity ratios according to an exemplary embodiment of the present disclosure.
Figure 4E:
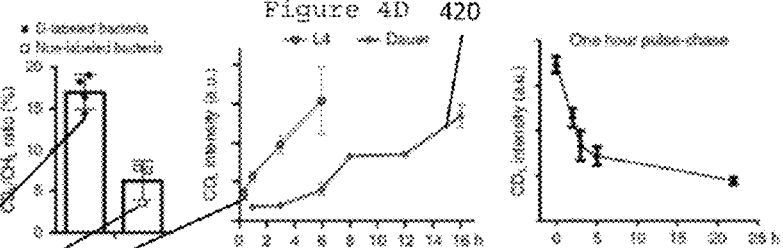
FIG. 4E is an exemplary chart of the CDL intensity according to an exemplary embodiment of the present disclosure.
Figure 4C:
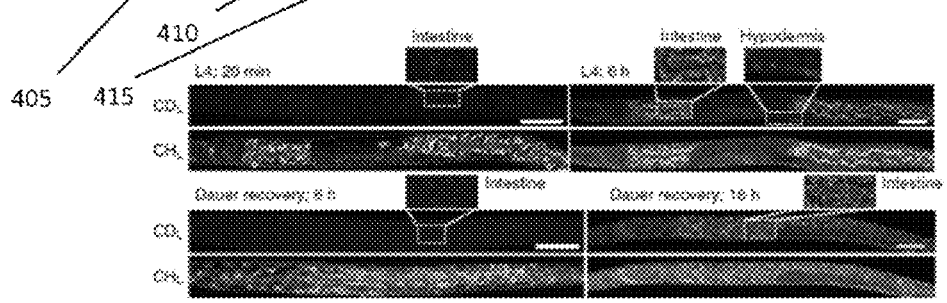
FIG. 4C is a set of exemplary images of normal fourth-stage larva and dauer larva according to an exemplary embodiment of the present disclosure.

FIGS. 4A-4E illustrate the exemplary DO-SRS visualizes de novo lipogenesis in cultured cells and in C. elegans. FIG. 4A shows a set of exemplary images that illustrate SRS signals at 2110 cm$^{-1}$ of HeLa cells grown in DMEM with 1% FBS and 10 µM of D34-oleic acids (D-OA) or D31-palmitic acids (D-PA) for 6 hours, compared to the signals from HeLa cells grown in DMEM with 1% FBS and 70% $D_2O$ for 24 hours. The number of lipid droplets formed in the three conditions were quantified (mean±s.d.; N=5 for D-OA, 15 for D-PA, and 8 for $D_2O$; double asterisks indicate p<0.01 in an unpaired t-test). $CH_L$ signal for $D_2O$ treatment confirmed the presence of few lipid droplets. FIG. 4 B shows an exemplary graph that illustrates SRS signal intensity ratios (mean±s.d.) of third stage larva grown from eggs on 20% $D_2O$ plates seeded with live (N=4) or UV-killed (N=3) E. coli OP50 24 hours before imaging. Live bacteria were labeled by deuterium (element 405), and killed bacteria were not labeled (element 410). FIG. 4C shows a set of exemplary images of normal fourth stage larva (L4) or dauer larva were transferred from regular NGM plates made of $H_2O$ to plates made of 20% $D_2O$ and then imaged at different time points. E. coli OP50 were seeded onto the $D_2O$ plates 24 hours before the experiments. Scale bar=20 µm. FIG. 4D shows an exemplary graph of the quantification of the mean intensity over the entire worm body for L4 415 and Dauer 420. FIG. 4E shows an exemplary graph of how L4 animals were first grown on $D_2O$ plates for 1 hour and then transferred to $H_2O$ plates and imaged at different time points after the transfer. $CD_L$ mean intensity was plotted. For all C. elegans experiments, at least 8 animals were imaged for each condition to calculate mean intensity; mean±s.d. of the mean intensity was shown.

FIGS. 5A-5H illustrate the exemplary DO-SRS visualizes de novo lipogenesis in mice in vivo. FIGS. 5A and 5B show a set of exemplary images and a graph of how car skin were harvested from adult mice drinking 25% $D_2O$ for 2, 8, or 26 days, and the sebaceous glands were imaged from the $CD_L$ and $CH_L$ channels, from which signals were coded as 505 and 510, respectively. The ratio of $CD_L$ mean intensity to $CH_L$ mean intensity across an entire gland unit was quantified. Mean±s.d. is plotted; N=8, 6, and 7 for 2-day, 8-day, and 26-day treatment, respectively. FIG. 5C shows a set of exemplary images of internal capsule of the mouse brain from P5 (5 days postnatal) and P11 pups and adults were sectioned and imaged. Pups were fed on milk produced by mother mice drinking 25% $D_2O$ for 6 days before imaging, and adults drank 25% $D_2O$ for 9 days before imaging. FIG. 5D shows an exemplary graph of the quantification of myelination activities in different brain regions by feeding pups for 6 days (element 520), 11 days (element 525) and adults (element 530). $CD_L$ signals were quantified as the mean intensity (mean±s.d.) of the entire image; N is between 8 and 14.

FIGS. 5E and 5F show a set of exemplary images and a graph, which illustrate white and brown adipose tissues from juvenile (P25, element 535) and adult (3-month old, element 540) mice drinking 25% $D_2O$ for 5 days were imaged. Difference between WAT ('W') and BAT ('B') were shown, as an example, by the enlarged regions (dashed square 515) of the adult tissues; fluorescence signal excited at 488 nm and collected at 525 nm were shown in purple. FIGS. 5G and 5H show a set of exemplary images and a graph of adipose tissues from wild-type mice 545 and ob/ob adult mice 550 that drank 25% $D_2O$ for 24 days. For quantification in FIGS. 5F and 5H show mean±s.d. Double asterisks indicate p<0.01 in an unpaired t-test. Three mice were used for each condition, and three or four fields were imaged for each tissue. Scale bar=20 µm for the entire Figure. The color scale bars represent the scale for $CD_L/CH_L$ ratio.

Figure 6:
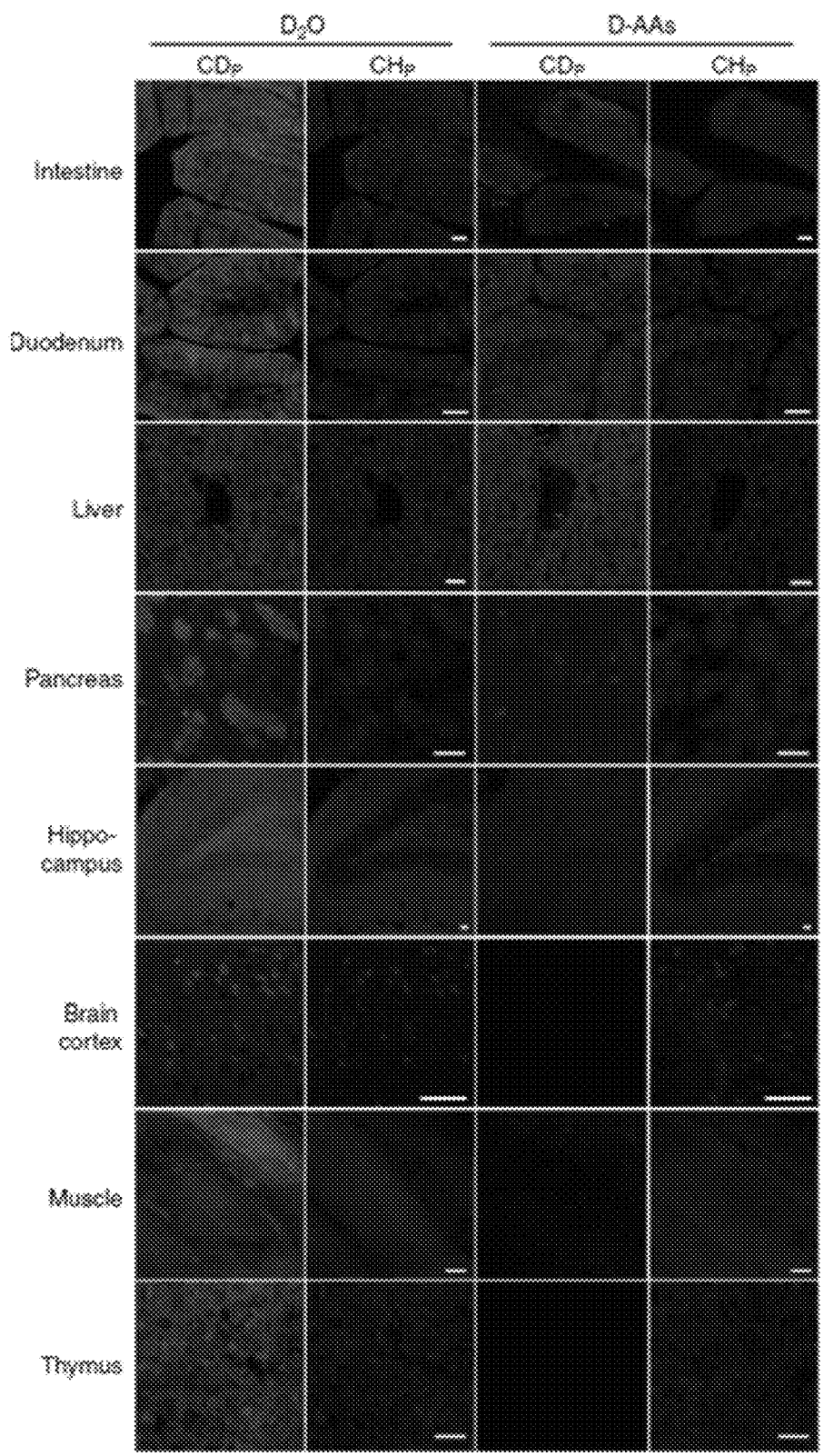
FIG. 6 is a set of DO-SRS microscopy images of the tracking of in vivo protein synthesis according to an exemplary embodiment of the present disclosure.

FIG. 6 shows a set of exemplary images that illustrate the exemplary DO-SRS, which can facilitate tracking of in vivo protein synthesis with high efficiency and without tissue bias. A variety of protein-rich organs were collected from adult mice that were administrated with 25% $D_2O$ or 2 mg/ml of D-AAs in drinking water for 8 days and then imaged for $CD_P$ and $CH_P$ signals. Scale bar=20 μm.

FIGS. 7A-7E show exemplary graphs and images that illustrate the exemplary DO-SRS visualizes in vivo protein and lipid metabolism simultaneously in C. elegans. FIG. 7A shows a set of exemplary images of germline development (see. e.g., Reference 66) with mitotic region 705, transition 710 (e.g., early prophase of meiosis 1), pachytene 715, spermatogenesis 720, and oogenesis 725. In adults, a gradient from element 730 to element 735 indicates the development (e.g., as shown by the arrow) from newly fertilized eggs to 32-cell embryo, which can be expelled via the vulva (e.g., as shown by the triangles). FIG. 7B shows a set of exemplary images of LA animals and day 0 adults were grown on 20% $D_2O$ plates for 3 hours before imaging (dashed outline indicates the gonad). Scale bar=20 μm. FIG. 7C shows an exemplary graph of day 0-7 adults for $CD_L/CH_L$ 740 and $CD_P/CH_P$ 745 were grown on 20% $D_2O$ plates for 3 hours and then imaged. Mean intensity ratios (mean±s.d.) were shown for animals divided into 4 age groups. N 10 in each group.

FIG. 7D shows an exemplary graph of day 0 to day 8 adults were transferred from regular NGM plates to 20% $D_2O$ plates and then imaged in 3 hours. The percentage of animals that showed CD signals in clumps in the body cavity and outside of the oocytes were shown; N=8 for each time point. FIG. 7E shows a set of exemplary SRS images of day 5 and day 8 adults after 3-hour $D_2O$ probing. Arrows 750 indicate newly formed lipid and protein accumulations only labeled by CD signals, whereas arrowheads indicate pre-existing mass labeled by CH signals. The color scale bars represent the scale for $CD_L/CH_L$ and $CD_P/CH_P$ ratios.

FIGS. 8A-8E show exemplary images and graphs that illustrate the exemplary DO-SRS, in combination with fluorescent labeling, tracks lineage-specific metabolism during zebrafish embryogenesis. FIGS. 8A-8C show images of the SRS signal and the colocalization with fluorescence from Tg(kdrl::EGFP) reporter in zebrafish embryos that were incubated in egg solution containing 20% $D_2O$ from 0 to 24 hpf, from 24 to 34 hpf, or from 34 to 48 hpf. Dashed curves 805 outline the yolk sac extension (labeled as Y) and the GFP-positive hemangioblast (labeled as H) that has strong $CD_P$ signal. Arrows 810 point to the GFP-positive cells that can likely be differentiating angioblasts in FIG. 8B. FIGS. 8D and 8E show exemplary intensity profiles that quantify the $CD_P$ signal within the yellow rectangle for 0-24 and 34-48 hpf probing, respectively. X axis shows the position along the length of the box from top to bottom, and Y axis shows the average intensity across the width of the box. Scale bar=20 μm.

FIGS. 9A-9D show exemplary images that illustrate the exemplary DO-SRS identifies tumor boundaries and metabolic heterogeneity. FIG. 9A shows a set of exemplary images of intracranial xenograft glioblastoma in mouse brain were excised, sectioned, and imaged after the tumor-bearing mice drank 25% $D_2O$ for 15 days. Dashed curves 905 highlight the tumor-brain boundary visualized by $CD_P$ signal. Intensity profile quantifies the $CD_P$ signal within rectangle 910 with X axis showing the position along the length of the box and Y axis showing the average intensity across the width of the box. FIG. 9B shows a set of exemplary images similar to FIG. 9A where exemplary methods were used to visualize the tumor-skin boundary of subcutaneously xenografted colon tumor from the $CD_L$ channel. FIG. 9C shows a set of exemplary images of the interior of the colon tumor xenografs imaged after the tumor-bearing mice drank 25% $D_2O$ for 3 or 15 days. Dashed lines 915 indicate the boundary between the tumor cells (labeled as T) and the recruited stromal cells (labeled as S), which were identified by the $CD_L$ signals at 3 days. Tumor and stromal cells were also identified by their different morphologies. Scale bar=20 μm. FIG. 9D shows a set of intensity profile quantifies the $CD_P$ or $CD_L$ signal within the rectangle 910 with the X axis showing the position along the length of the box and Y axis showing the average intensity across the width of the box.

Figure 10E:
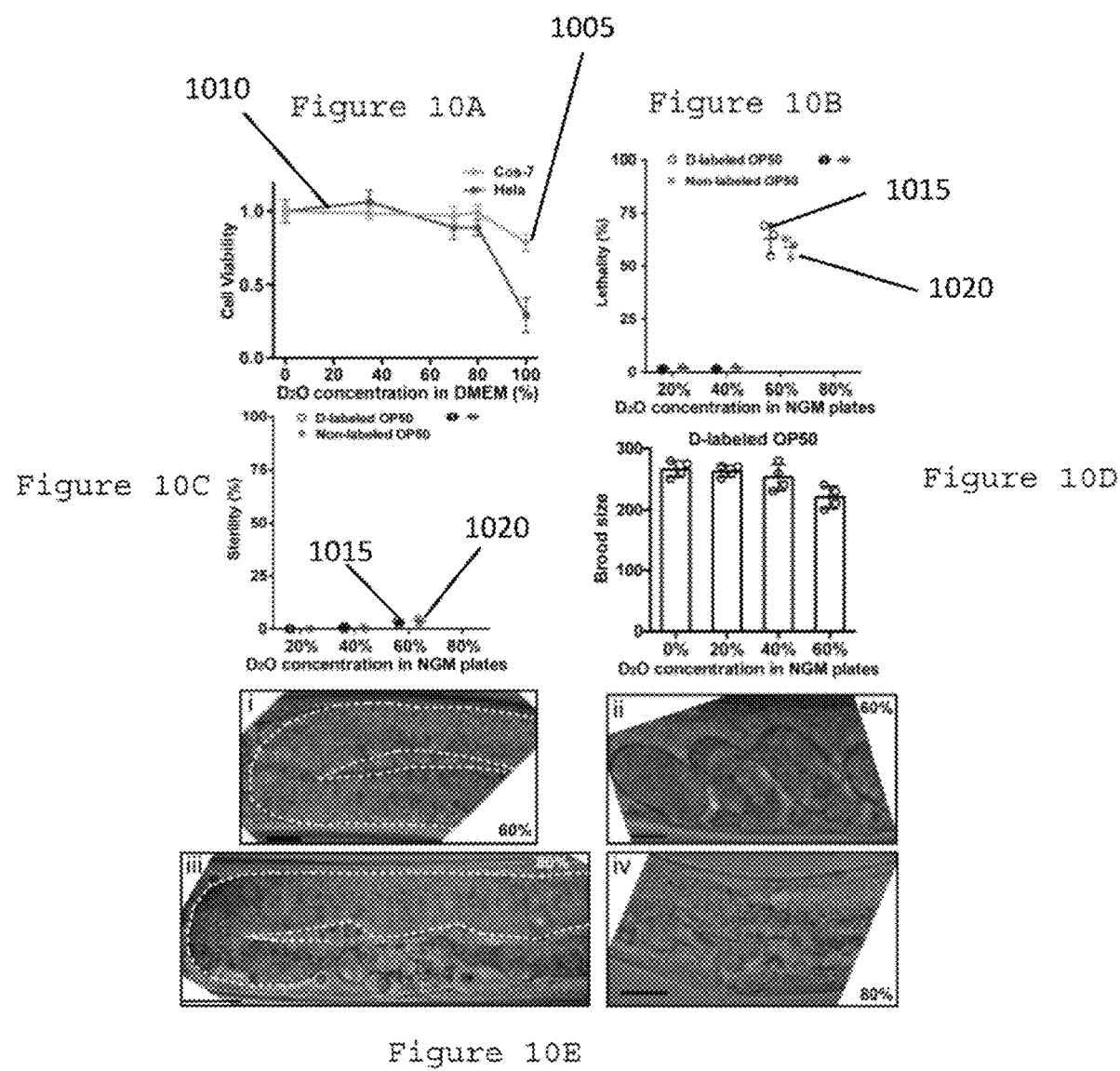
FIG. 10E is a set of exemplary images of the gonad at 60% $D_2O$ concentration according to an exemplary embodiment of the present disclosure.

FIGS. 10A-10E show exemplary graphs and images that illustrate toxicity of $D_2O$ on cells and C. elegans. FIG. 10A shows a graph of CellTiter-Glo Luminescent Cell Viability Assay, which quantities ATP production, was performed on COS-7 cells (line 1005) and HeLa cells (line 1010) grown in DMEM made of different concentration of $D_2O$ for 48 hours. Three replicates were performed. Mean and s.d. were shown. FIG. 10B shows a graph of how lethality was determined by placing hypochlorite-prepared eggs onto NGM plates made of different concentration of $D_2O$ and calculating the percentage of eggs that hatched into normal, moving larva. D-labeled OP50 (line 1015) refers to overnight grown culture of E. coli OP50 that were seeded onto the $D_2O$-containing NGM plates 24 hours before the experiment; non-labeled OP50 (line 1020) refers to the experimental setup, in which bacteria were killed by UV after being placed onto the $D_2O$ plates and thus was not labeled by deuterium. Each group has 50 worms, and three replicates were made. Mean and s.d. were shown.

FIG. 10C shows a graph illustrating how sterility was determined as the percentage of fourth stage larva (L4) that became sterile after being transferred to $D_2O$ plates for D-labeled OP50 (line 1015) and non-labeled OP50 (line 1020). FIG. 10D shows a graph of brood size, which reflects the effects on meiosis, was determined by counting the total number of viable progeny one animal produced. 50 worms were used for each treatment, and four replicates were made. Mean and s.d. were shown. FIG. 10E shows a set of exemplary images 60% $D_2O$ concentration, the gonad developed normally (i) and normal embryos were formed (ii) in animals that developed from L4 to adults on $D_2O$ plates. With 80% $D_2O$, gonad development was disrupted and proliferation of the germ cells appeared to be affected (iii) and no embryos were formed in the uterus (IV). Scale bar=20 μm.

FIGS. 11A-11F show graphs and images that illustrate the development of a three-component un-mixing procedure. FIG. 11A shows a graph of a spontaneous Raman signal of extracted D-lipids 1105, D-proteins 1110, and D-DNA 1115 from $D_2O$-treated HeLa cells. Signals for each type of macromolecules were normalized to their own peaks. Un-mixing coefficients were first measured from the spectra and then adjusted by setting $a_L$, $b_P$, and $c_{DNA}$ to 1 and scaling the other parameters accordingly. FIG. 10B shows an exemplary graph of colon tumor tissues (from mice that drank 25% $D_2O$ for 15 days) before methanol wash (signal 1130) and after methanol wash (signals 1120 and 1125). Pure deuterium-labeled protein signals (signal 1120) were assumed as the methanol-resistant signal, and pure deuterium-labeled lipid signals (1125) were calculated as the signal difference before and after methanol wash. All signals were normalized to the phenylalanine peak.

FIG. 11C shows an exemplary graph of similar methanol wash and signal normalization methods that were applied to mouse brain and pancreas tissues, in addition to tumor tissues. The average (e.g., proteins average line 1135 and lipids average 1155), normalized pure protein signal intensities for the brain 1140, pancreas 1145 and tumor 1150, and pure lipid signal intensities for the brain 1160, pancreas 1165 and tumor 1170 were calculated; mean±SD for the coefficients were shown. FIG. 11D shows SRS images of methanol-washed colon tumor tissues (taken from tumor-bearing mice that drank 25% $D_2O$ for 15 days) before and after un-mixing ($a_L=1$; $a_P=0.40$; $b_P=1$; $b_L=0.51$). FIGS. 11E and 11F are exemplary images that show un-mixing was applied to COS-7 cells grown in 70% $D_2O$ DMEM containing 10 nM TVB-3166 for 24 hours and HeLa cells grown in 70% $D_2O$ DMEM containing 1 µM anisomycin for 24 hours, respectively. Un-mixing equations can be found in the Methods. Scale bar=20 µm.

FIGS. 12A-12C show exemplary images and a graph that illustrate imaging lipogenesis in C. elegans. FIG. 12 shows a set of exemplary images for hypochlorite-prepared eggs of C. elegans were placed onto 20% $D_2O$ NGM plates pre-seeded with E. coli OP50 and third stage larva grown from those eggs were imaged. For the live bacteria group, OP50 grew on the $D_2O$ plates for 24 hours at room temperature before eggs were placed; for the dead bacteria group, bacteria cells were killed by UV after being seeded onto the $D_2O$ plates, and 24 hours later, eggs were placed onto the plate. Quantification is shown in the images shown in FIG. 13B. For example, FIG. 12B shows how OP50 bacterial culture was mixed with 4 mM D31-palmitic acid and then seeded onto NGM plates that contain 100% HO. C. elegans eggs were placed onto those plates and as controls 20% $D_2O$ plates with OP50 seeded the day before. 48 hours later, L4 animals were imaged. The scale bar represents the scale for $CD_L/CH_L$ and $CD_P/CH_P$ ratios. FIG. 12C shows an exemplary graph that illustrates a comparison of the $CD_L/CH_L$ ratio for animals fed with D31-PA and the ones grown on $D_2O$ plates. Mean±s.d. are plotted; N 3 for each treatment. Scale bar 50 µm.

Figure 13A:
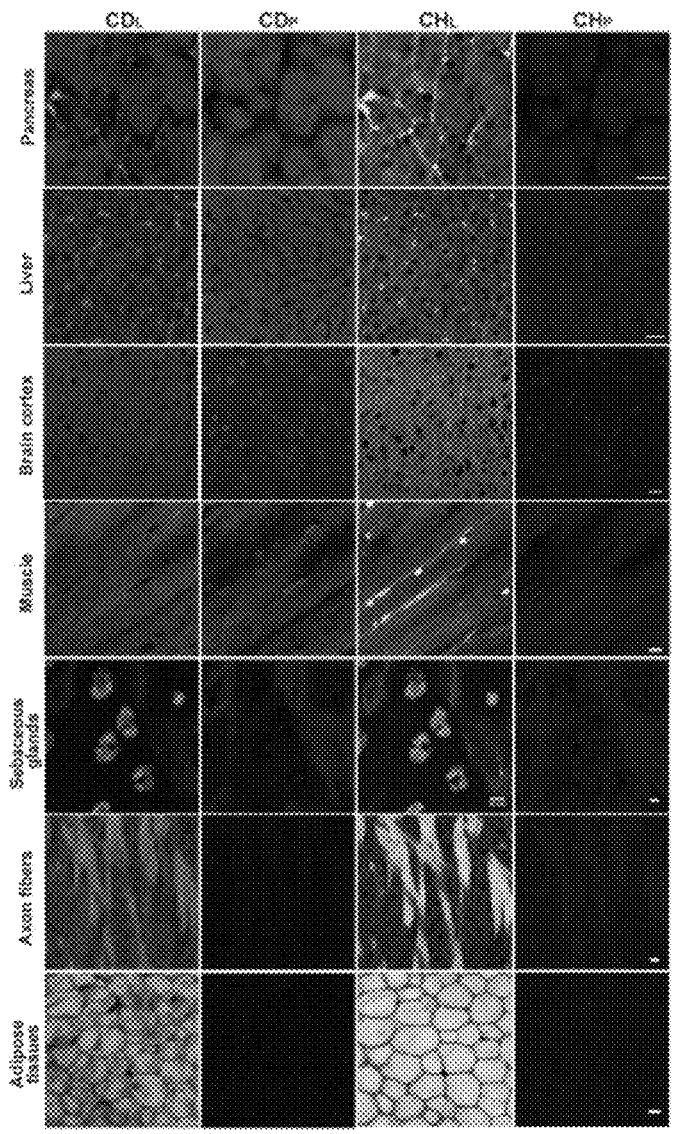
FIG. 13A is a set of exemplary images of various protein-rich tissues according to an exemplary embodiment of the present disclosure.
Figure 13B:
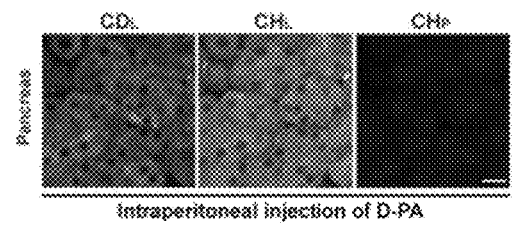
FIG. 13B is a set of exemplary images of the CDL signal of the pancreas collected from mice that were intraperitoneally injected with 0.16 ml of 600 mM D-PA emulsion according to an exemplary embodiment of the present disclosure.
Figure 13C:
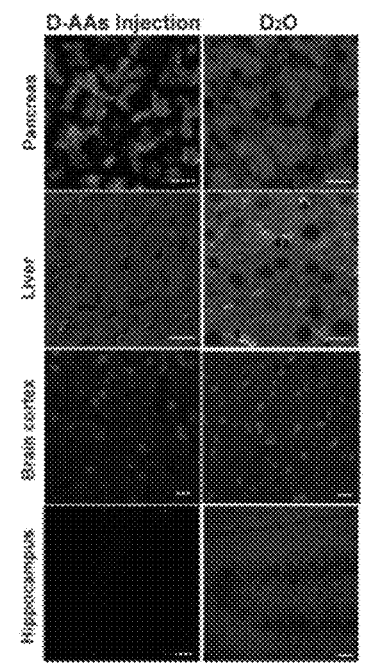
FIG. 13C is a set of exemplary images of CDP signals of various organs from mice that were injected with D-labeled amino acids ("d-AAs") via carotid artery and mice that drank 25% $D_2O$ for 8 days according to an exemplary embodiment of the present disclosure.

FIGS. 13A-13C show exemplary images that illustrate imaging de novo biosynthesis in various mouse organs. FIG. 13A shows a set of exemplary images that illustrate various protein-rich tissues, including pancreas, liver, brain cortex, and muscle, were collected from adult mice that drank 25% $D_2O$ for 20 days and then imaged. Lipid-rich sebaceous glands and adipose tissues were harvested from adult mice that drank 25% $D_2O$ for 8 and 15 days, respectively. Myelinated axon fibers of internal capsule were harvested from P11 mouse pups that were fed on milk produced by mother mice drinking 25% $D_2O$ for 6 days before imaging. FIG. 13B shows a set of exemplary images for the $CD_L$ signal of the pancreas collected from mice that were intraperitoneally injected with 0.16 ml of 600 mM D-PA emulsion. Tissues were harvested, fixed, and imaged 17 hours after the injection. FIG. 13C shows a set of exemplary images of $CD_P$ signals of various organs from mice that were injected with D-labeled amino acids (d-AAs) via carotid artery and mice that drank 25% $D_2O$ for 8 days. Scale bar=20 sm.

The exemplary system, method, and computer-accessible medium, according to an exemplary embodiment of the present disclosure, can include imaging metabolic activities in live cells, microbes, plants, animals, and humans, which can include introducing an effective amount of deuterium oxide (heavy water, $D_2O$) as the probe into live cells, organisms, and animals, wherein deuterium from heavy water can incorporate into metabolic activities by forming carbon-deuterium bonds (C-D) and utilizing stimulated Raman scattering (SRS) microscopy, Raman spectroscopy, Fourier-transform infrared spectroscopy (FTIR) to detect and image the vibration of carbon-deuterium bonds in live cells, plants, microbes, animals, and humans.

Within the broad vibrational spectra of C-D bonds (approximately 2100 $cm^{-1}$ to approximately 2300 $cm^{-1}$), lipid-, protein-, and DNA-specific Raman shifts can be discovered. Spectral un-mixing procedures can be developed with molecular selectivity to differentiate C-D signals of lipids, proteins, and DNA peaks. SRS imaging or Raman imaging or Raman spectroscopy can be used to visualize, detect or quantify a specific newly-formed macromolecules such as protein, lipids, and DNA. Heavy water can be incorporated into protein, lipids and DNA, and can generate carbon deuterium (C-D) bonds. Each newly formed molecule can have a specific Raman shift peak. The newly formed lipids with C-D bond (C-D lipids) can have a Raman shift centered at 2135 $cm^{-1}$, the newly formed protein with C-D bond (C-D protein) can have a Raman shift centered at 2185 $cm^{-1}$, the newly formed DNA bond (C-D DNA) can have a Raman shift centered at 2210 $cm^{-1}$.

Lipid metabolic activities can be tracked, detected, and imaged at 2135±25 $cm^{-1}$. The de novo lipogenesis in various organs or tissues, in vivo or ex vivo, can be quantified. The newly formed C-D lipids intensity can be quantified. The lipids turnover rate can be quantified as the ratio of C-D lipids to label free lipids ($CH_2$). C-D protein metabolic activities can be tracked, detected and imaged at 2185 $cm^{-1}$±15 $cm^{-1}$. The protein biosynthesis in various organs or tissues, in vivo or ex vivo, can be quantified. The newly formed C-D protein intensity can be quantified. The protein turnover rate can be quantified as the ratio of C-D protein to label free protein ($CH_3$). Lipids and protein metabolic activities in live cells, microbes, animals or in humans, or photosynthesis in plants can be simultaneously tracked, detected, and imaged at 2135 $cm^{-1}$ 15 $cm^{-1}$ (C-D lipids) and 2185 $cm^{-1}$±15 $cm^{-1}$ (C-D protein), respectively. C-D lipids and C-D protein biosynthesis in various organs or tissues, in vivo or ex vivo, can be quantified. Protein biosynthesis can be imaged without tissue bias, and simultaneously visualize lipid and protein metabolism and reveal their different dynamics. The newly formed C-D lipids and protein intensities can be quantified.

The lipids (or protein) turnover rate can be quantified as the ratio of C-D lipids (or C-D protein) to label free ($CH_2$) lipids (or $CH_1$ protein). Newly formed C-D lipids and C-D protein can be simultaneously labeled, detected, and imaged at 2135 $cm^{-1}$±15 $cm^{-1}$ (C-D lipids) and 2185 $cm^{-1}$±15 $cm^{-1}$ (C-D protein), respectively. Lipids and protein biosynthesis in various organs or tissues, in vivo or ex vivo, can be quantified. C-D lipids and C-D protein signals can be unmixed for accurate quantification of lipids and protein metabolic activities, respectively. The unmixed C-D lipids and unmixed C-D protein signals can be used for accurate quantification of newly formed C-D lipids and protein turnover rates, which can be the ratios of C-D lipids (or C-D protein) to label free lipids ($CH_2$)(or $CH_3$ protein). Newly formed C-D lipids, C-D protein and C-D DNA can be simultaneously labeled, detected, and imaged at 2135 $cm^{-1}$±5 $cm^{-1}$ (C-D lipids), 2185 $cm^{-1}$±15 cm (C-D protein), and 2210 $cm^{-1}$±10 $cm^{-1}$ (DNA), respectively.

C-D lipids, C-D protein and C-D DNA biosynthesis in live cells, microbes, animals or in humans, or in plants, in vivo, in vitro, or ex vivo, can be quantified. C-D lipids C-D protein and C-D DNA signals can be unmixed for accurate quantification of lipids and protein metabolic activities, respectively. The unmixed C-D lipids, unmixed C-D protein and unmixed C-D DNA can be used for accurate quantification of newly formed C-D lipids, protein, and DNA turnover rates, which can be the ratios of C-D lipids to label free lipids ($CH_2$), C-D protein to label free protein ($CH_3$), and C-D DNA to label free DNA, respectively.

Direct visualization of metabolic dynamics from vibrational images in live cells, microbes, animals, plants, and humans with high spatial and temporal resolution can be beneficial to understand many biological processes such as development, aging, homeostasis, tumor progression, to detect tumor boundaries, intra-tumor heterogeneity, microbes, metabolic activities, plant photosynthesis. Procedures for un-mixing newly synthesized C-D protein, C-D lipids and C-D DNA can be used in computer programs (software) to calculate and quantify metabolism in live cells, plants, microbes, animals, and humans. Imaging of metabolic changes of C-D protein, C-D lipids by heavy water labeling can be used as a detection indicator for various diseases developments such as Alzheimer's, cancer, diabetes, and obesities. Imaging metabolic changes of C-D protein. C-D lipids by heavy water labeling can be used as a detection indicator for prenatal or postnatal development and cell lineages.

The imaging metabolic changes of C-D lipids and C-D protein via heavy water labeling can be used for tumor detection, tumor boundary detection, degree of tumor aggressiveness, tumor progression, and intratumor metabolic heterogeneity study, including skin cancer, breast cancer, mouth cancer, throat cancer, etc. The imaging of metabolic changes of C-D protein and C-D lipids by heavy water labeling can be used as medical imaging of injury or disease recovery, including brain trauma, spinal cord injury, small vessel diseases, bone injury, cancer, etc. The imaging of metabolic changes of C-D protein and C-D lipids by heavy water labeling can be used as medical imaging of injury recover, brain trauma, spinal cord injury. Imaging of C-D protein and C-D lipids by heavy water labeling can detect the metabolic heterogeneity of microbes or other living organism for screening genes, mutation detection.

Imaging of C-D protein and C-D lipids by heavy water labeling can detect the myelin formation, multiple sclerosis, and its recovery. Imaging skin metabolism/regeneration tests can be carried out to track C-D proteins (such as collagen inside skin), C-D lipids metabolic activities. The exemplary system, method, and computer-accessible medium, according to an exemplary embodiment of the present disclosure, can be used in the cosmetic and skin care industry.

Figure 14:
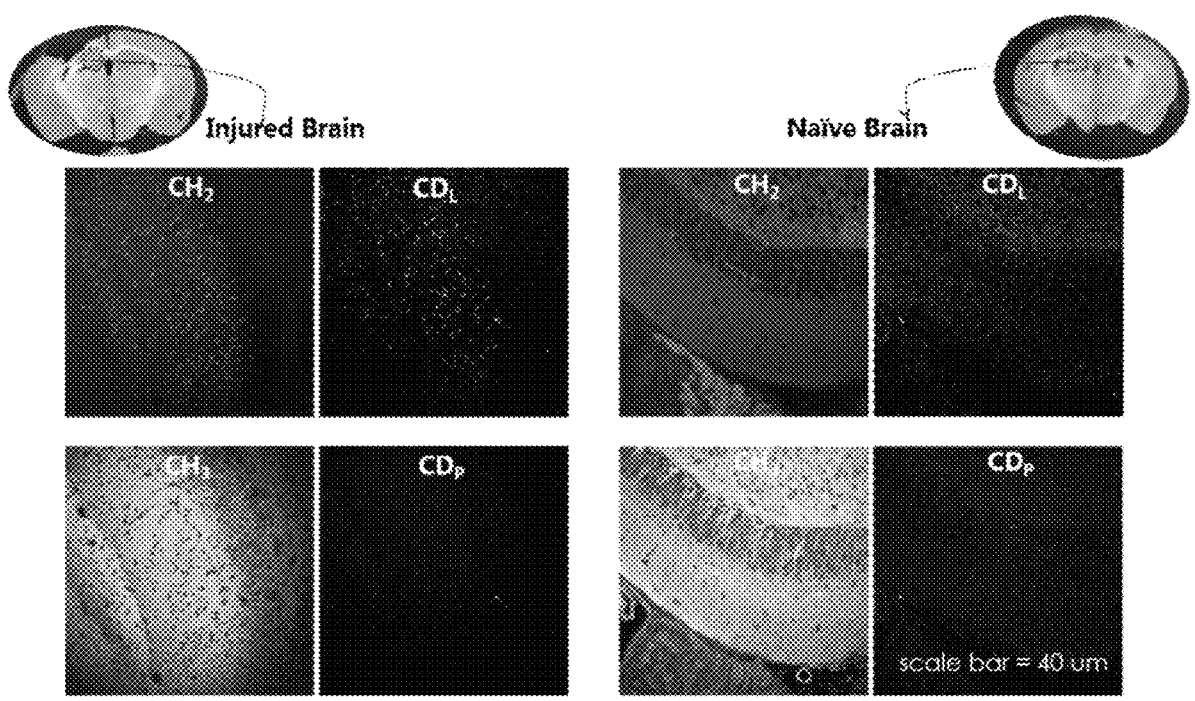
FIG. 14 is a set of exemplary SRS images of CDP and CDL signals of a traumatic injured brain and a naïve brain from mice that drank 25% $D_2O$ for 4 days according to an exemplary embodiment of the present disclosure.

FIG. 14 shows a set of exemplary SRS images of $CD_P$ and $CD_L$ signals of a traumatic injured brain and a naïve brain from mice that drank 25% $D_2O$ for 4 days according to an exemplary embodiment of the present disclosure. For example, when the brain is injured, the metabolic activities of lipids and protein inside the brain tissue can be different from a naïve brain. To direct visualize the metabolic activities in an injured brain, 25% $D_2O$ was fed to the mice with traumatic brain injury ("TBI") and the naïve mice as control. After 7 days of heavy water treatment, the brain was removed and the newly synthesized CD protein and CD lipids channel were examined by SRS imaging, which found that the injured brain has numerous bright clusters of CD: signals occurred. However, the naïve brain does not show any of this signals. Thus, the exemplary system, method and computer-accessible medium can be used for monitoring the metabolic changes during injury and its healing procedures.

FIG. 15 shows a set of exemplary images of CD signals of plant leaves from *Origanum vulgare* that were growing with 50% heavy water in normal water for 5 days and the Raman spectrum of the newly synthesized metabolites in the plant leaf according to an exemplary embodiment of the present disclosure. The images were taken from *Origanum vulgare* leaves which was grown in a water bottle containing 50% of heavy water for 5 days. Image 1505 is of a real *Origanum vulgare* plant in the bottle with water. The arrow is pointing at a relatively new leaf which is actively performing photosynthesis and was cut for SRS imaging after 5 days of photosynthesis. Graph 1510 shows the Raman spectrum of the newly synthesized metabolites in the plant leaf. The peak is located around 2194.8 $cm^{-1}$. Lower left side in the FIG. 15 illustrates the SRS image of CD signal in the *Origanum vulgare* leaf, which was the newly formed biomass by photosynthesis activities of the plant. Image 1515 shows the off resonance SRS image which is basically dark. Thus, the CD signals observed from 2194.8 $cm^{-1}$ were true signals from new biomass by photosynthesis. This experimental results illustrates that the exemplary system, method and computer-accessible medium can be used to visualize photosynthesis activities in plant. This deuterium probed high resolution vibrational imaging of photosynthesis illustrates where and how much of newly synthesized biomass inside the plants. Exemplary applications can include the green energy industry which uses algae's photosynthesis. The genetic background of algae can be manipulated and regulated in order to get the ultimate productivity of oils (lipids).

Figure 16A:
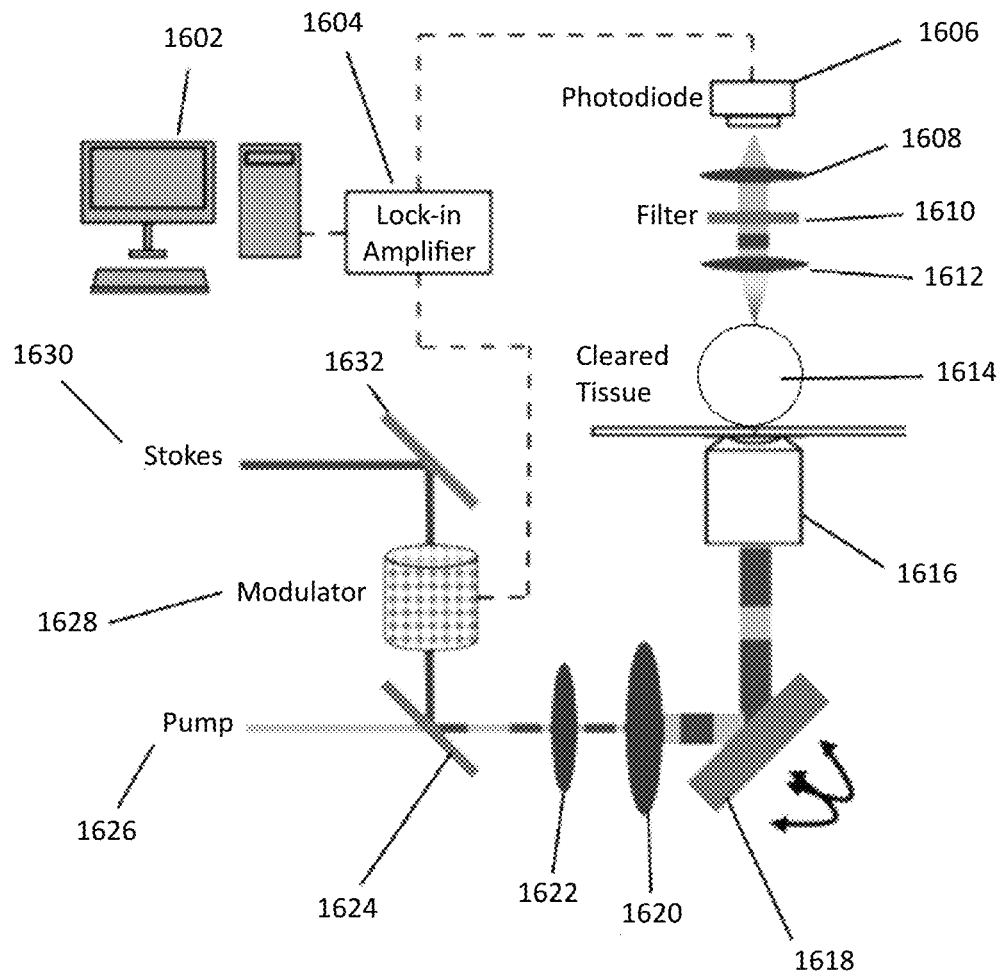
FIG. 16A is an exemplary schematic diagram of clearing-enhanced SRS microscopy according to an exemplary embodiment of the present disclosure.

FIG. 16A shows an exemplary schematic diagram of for clearing-enhanced SRS microscopy. For example, as shown in FIG. 16A, the pump laser beam 1626 and the stokes laser beam 1630 can coherently enter into an objective lens. The stokes beam 1630 can be reflected by mirror 1632, modulated using modulator 1628, and then reflected by mirror 1624 in order to be combined with the pump laser beam 1626. Both laser beams can pass through lenses 1622 and 1620 and then reflected by mirror 1618. Both laser beams can then arrive at objective 1616, and the tissue sample 1614 can be placed between the objective lens 1616 and a condenser 1612. The stokes laser beam 1630 can be blocked by a filter 1610, while the pump laser beam 1626 can pass through the lens 1608, and arrive at photodiode 1606. The pump laser beam 1626 can be received by the lock in amplifier 1604 and then computer 1602, and the signal can be stored in an exemplary storage arrangement for further analysis.

Figure 16B:
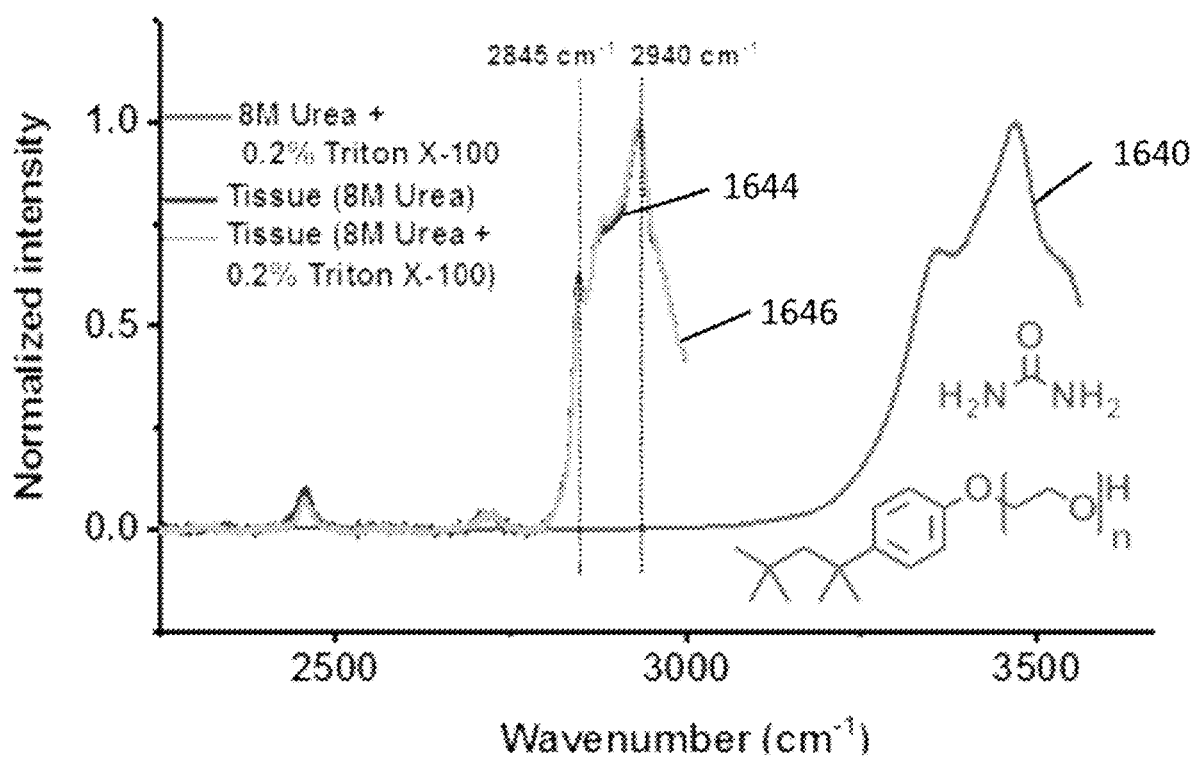
FIG. 16B is an exemplary graph illustrating the spontaneous Raman spectra according to an exemplary embodiment of the present disclosure.

FIG. 16B shows the spontaneous Raman spectra of 8 M urea and 0.2% Triton X-100 (line 1640), mouse brain slices in PBS (line 1642), slices cleared with 8 M urea (line 1644), and slices cleared with 8 M urea solution with 0.2% Triton X-100 (line 1646).

Figure 16C:
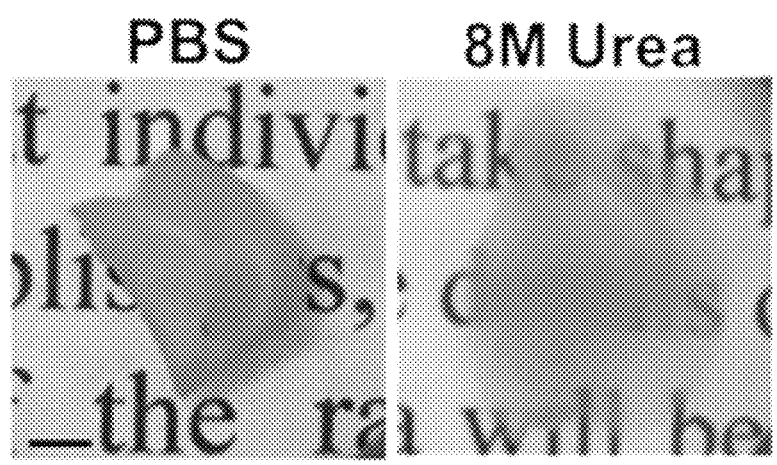
FIG. 16C is a set of exemplary photograps of 1-mm-thick brain slices in PBS according to an exemplary embodiment of the present disclosure.
Figure 16D:
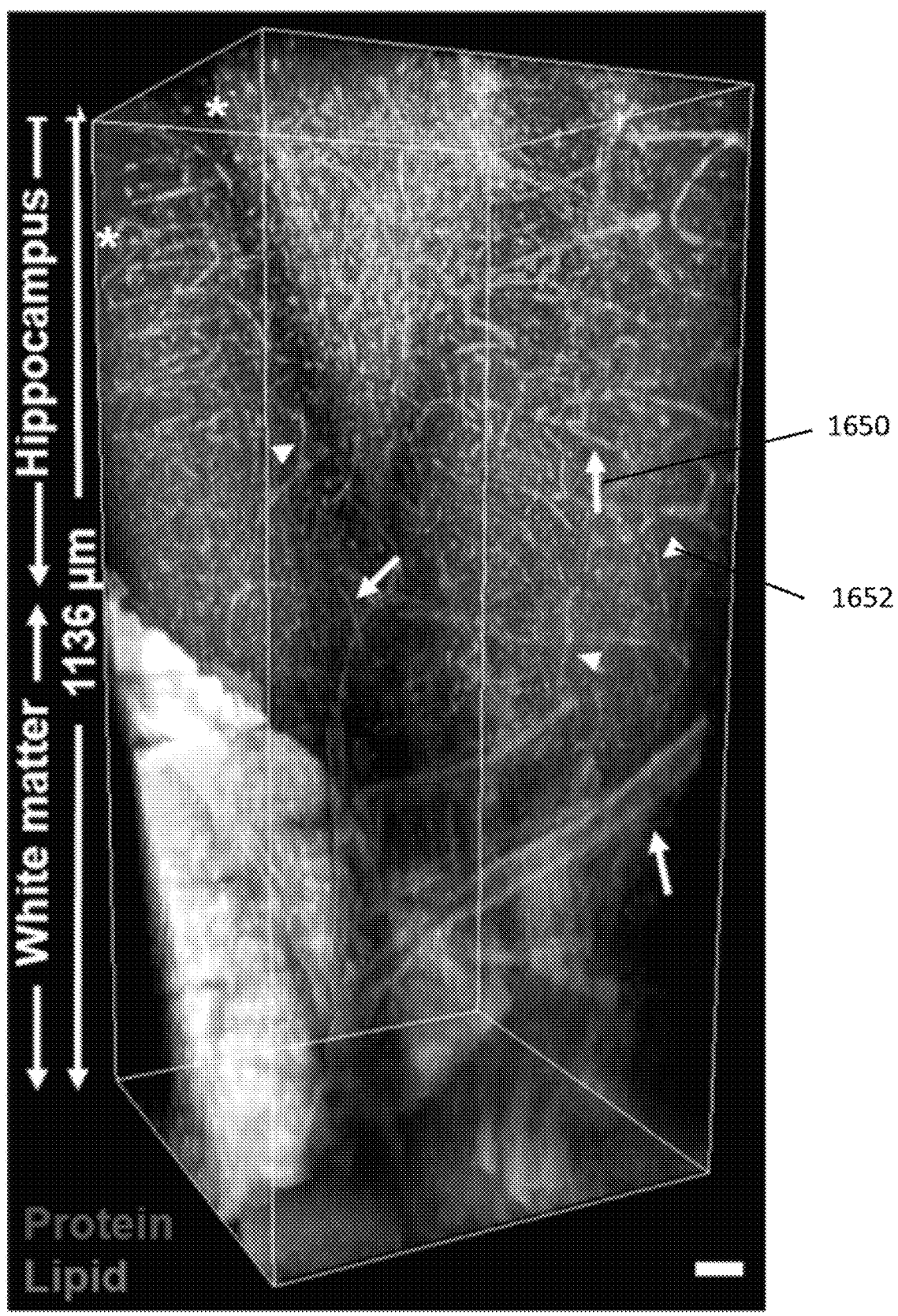
FIG. 16D is an exemplary image of clearing-enhanced volumetric chemical imaging of mouse brain tissues according to an exemplary embodiment of the present disclosure.
Figure 16E:
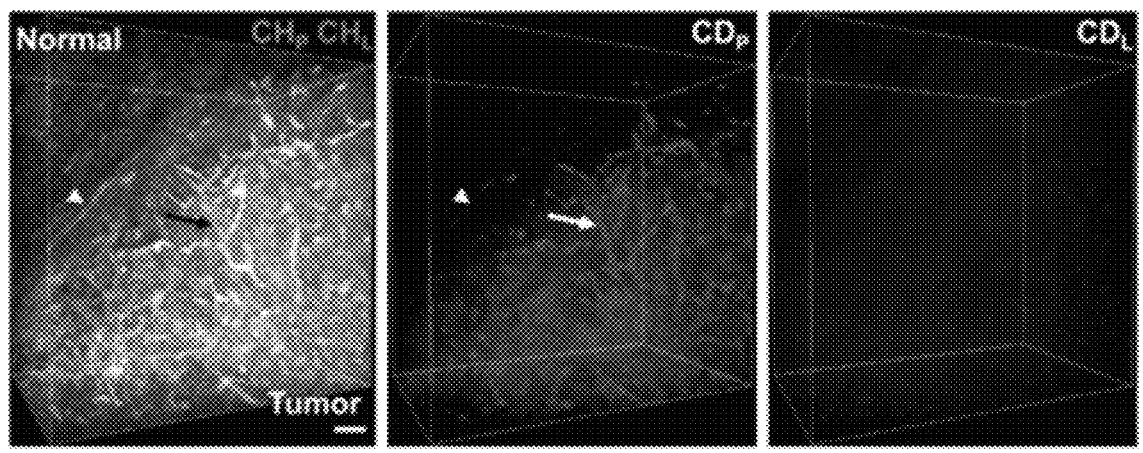
FIG. 16E is a set of exemplary metabolic volumetric chemical images of glioblastoma in a mouse brain according to an exemplary embodiment of the present disclosure.
Figure 16F:
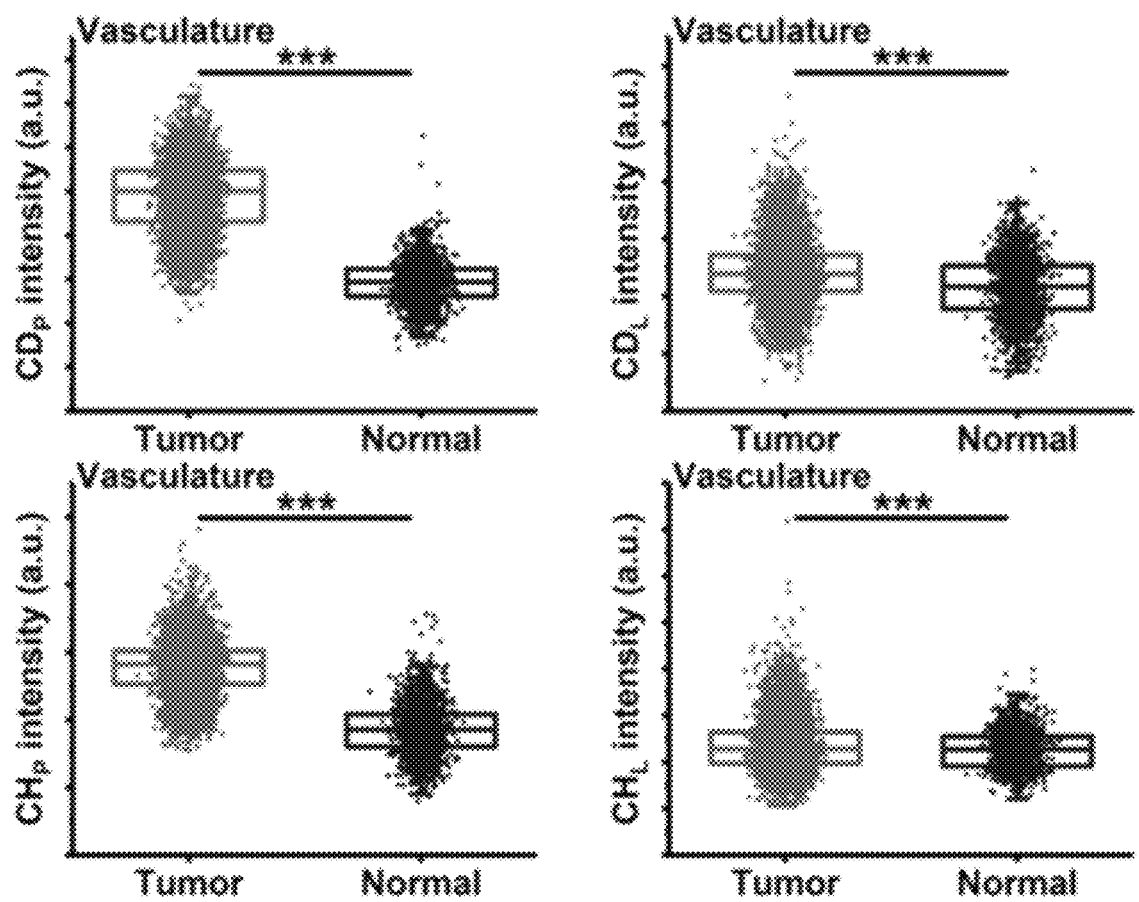
FIG. 16F is a set of exemplary graphs showing the intensities of CDP, CDL, CHP, and CHL of tumor vasculature and normal vasculature according to an exemplary embodiment of the present disclosure.
Figure 16G:
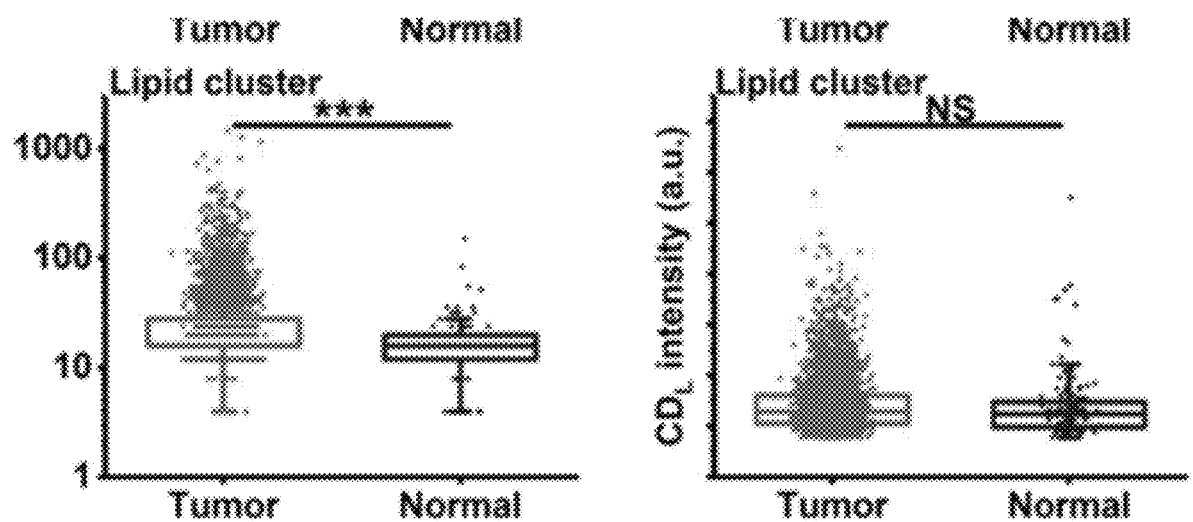
FIG. 16G is a set of exemplary graphs illustrating the volume and CDL intensities of clusters of newly synthesized lipids in the tumor and those in the normal tissue according to an exemplary embodiment of the present disclosure.

FIG. 16C shows the photographs of 1-mm-thick brain slices in PBS, cleared with 8 M urea and 0.2% Triton X-100. FIG. 16D shows an example of clearing-enhanced volumetric chemical imaging of mouse brain tissues—the three-dimensional reconstruction of the hippocampus and white matter. Arrows indicate vasculatures, arrowheads indicate axons, and stars indicate cell bodies. And FIG. 16E shows the metabolic volumetric chemical imaging of glioblastoma in a mouse brain. It is three-dimensional reconstruction of label-free SRS and heavy water probed SRS metabolic images. Arrows 1650 indicate a blood vessel in the tumor. Arrowheads 1652 indicate a blood vessel in the normal tissue. The Scale bar is 50 μm. FIG. 16F shows the intensities of $CD_P$, $CD_L$, $CH_P$, and $CH_L$ of tumor vasculature (n=7,588) and normal vasculature (n=1.605) from one mouse. FIG. 16O shows the volume and $CD_L$ intensities of clusters of newly synthesized lipids in the tumor (n=6,894) and those in the normal tissue (n=136) from one mouse. Statistical significance was determined by two-sample two-tailed t-test. ***P<0.001. NS, not significant. The metabolic basis of angiogenesis in tumor was examined. The experimental image data indicate: (i) active angiogenesis takes place in the tumor, (ii) metabolic reprogramming for tumor angiogenesis involves a major increase in protein synthesis and a minor increase in lipid synthesis, and (iii) tumor vasculature has a different chemical composition from normal vasculature. Based on high metabolic activity and distinct chemical composition of tumor vasculature (as shown in the graphs of FIG. 16F), tumor vasculature can derive from differentiation of glioblastoma stem cells into endothelial cells or pericytes, a phenomenon termed vascular mimicry. Additionally, it was observed that in CDL channel, newly synthesized lipids formed large clusters mainly in the tumor. (See e.g., images shown in FIG. 16E). As shown in the graphs of FIG. 16G, there are far more lipids clusters in the tumor than in the normal tissue: the clusters in the tumor had larger volume than those in the normal tissue, while their CDL intensities were not significantly different. These results indicate that tumor tissues exhibited more and larger localized hot spots of lipid synthesis than normal tissues. Thus, the exemplary system, method and computer-accessible medium, according to an exemplary embodiment of the present disclosure, can be used for studying metabolic heterogeneity in tumors.

Figure 17:
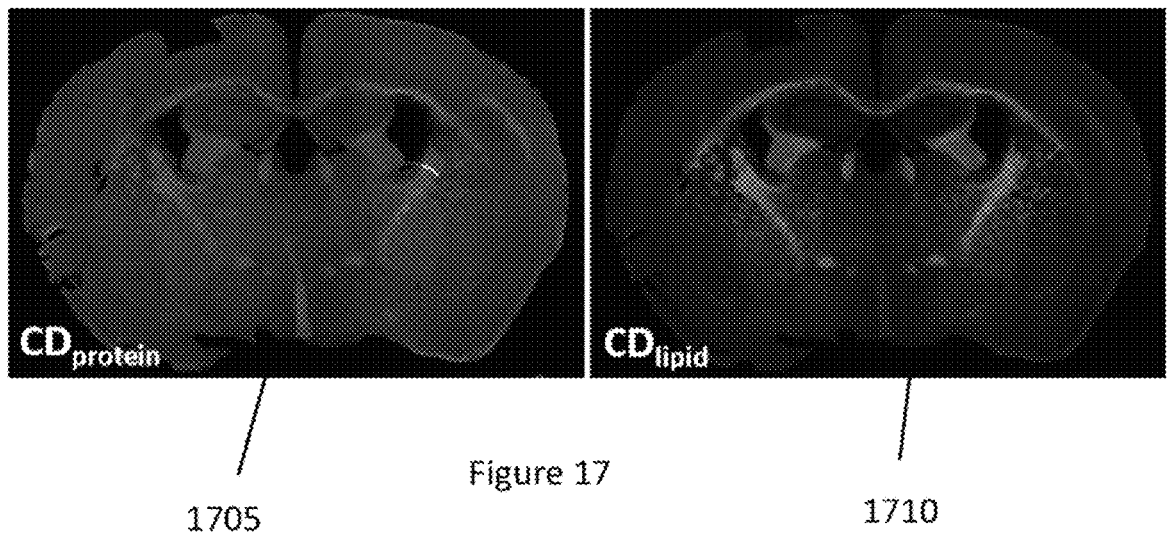
FIG. 17 is a set of exemplary FTIR images of CDP and CDL signals of a brain from a mouse pup that was fed milk by a dam that drank 25% $D_2O$ for 34 days since it was born in accordance with certain exemplary embodiments of the present disclosure.

FIG. 17 shows a set of exemplary FTIR images of CDP and CDL signals of a brain from a mouse pup that was fed milk by a dam that drank 25% $D_2O$ for 34 days since it was born according to an exemplary embodiment of the present disclosure. It is a Fourier transform infrared spectroscopy ("FTIR") with heavy water probed imaging technique. Image 1705 shows the heavy water derived CDP protein signals in the cross-sectional area from a whole mouse brain. Image 1710 shows the heavy water derived CDL lipids signals in the same region of interest of the brain. The brain was from a mouse pup that was fed milk by a dam that drank 25% $D_2O$ for 34 days since it was born. This experimental results shows that heavy water probed metabolic activities can be used to visualize the postnatal development in tissues in situ. The distributions of CDP and CDL signals inside the postnatal mice pup's brain indicate the regions in the brain that involve heavy myelination process. The time window for the myelination can be identified through the heavy water probed FTIR imaging. FTIR can also provide fast imaging acquisition, and can be used with fast optical imaging for 3D volumetric optical imaging with Quantum cascade lasers. Thus, the exemplary system, method and computer-accessible medium can be used for FTIR metabolic imaging in animals or human beings.

Figure 18A:
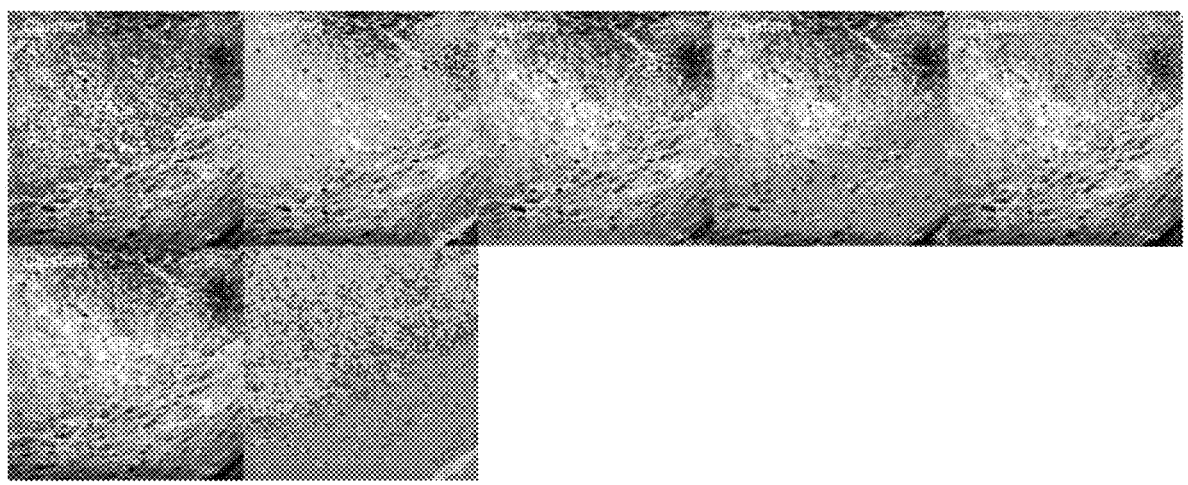
FIG. 18A is a set of exemplary SRS images of clustered CD signals of a brain according to an exemplary embodiment of the present disclosure.
Figure 18B:
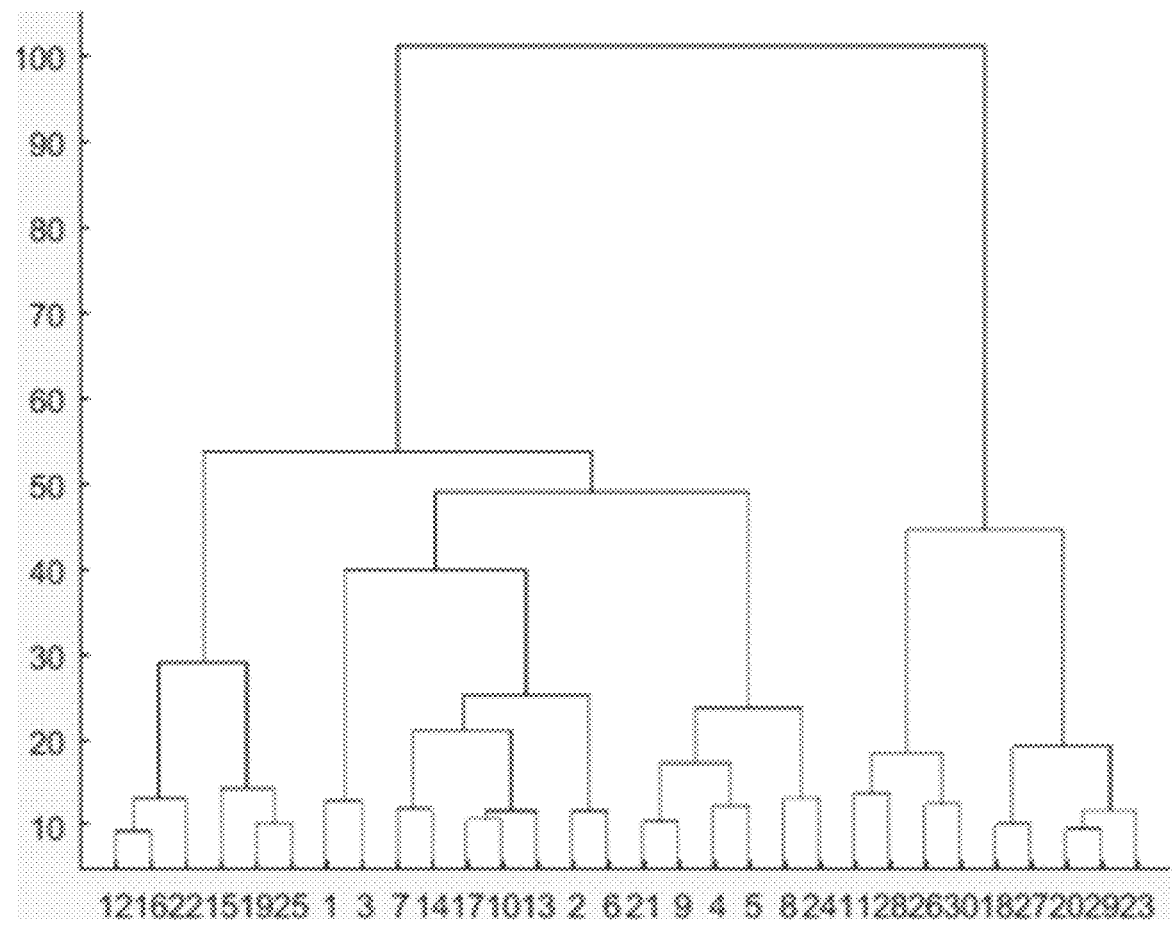
FIG. 18B is an exemplary graph illustrating Hierarchical Clustering Analysis of metabolic activities according to an exemplary embodiment of the present disclosure.

FIG. 18A is a set of exemplary SRS images of clustered CD signals of a brain according to an exemplary embodiment of the present disclosure. FIG. 18B is an exemplary graph illustrating Hierarchical Clustering Analysis ("HCA") of metabolic activities according to an exemplary embodiment of the present disclosure. For example, the dendrogram shows observations clustered into 6 groups. The X-axis represents the samples and y-axis shows the similarity index. The higher the variability index the larger the between group variability and the lower the similarity index, the smaller the between group variability.

Figure 18C:
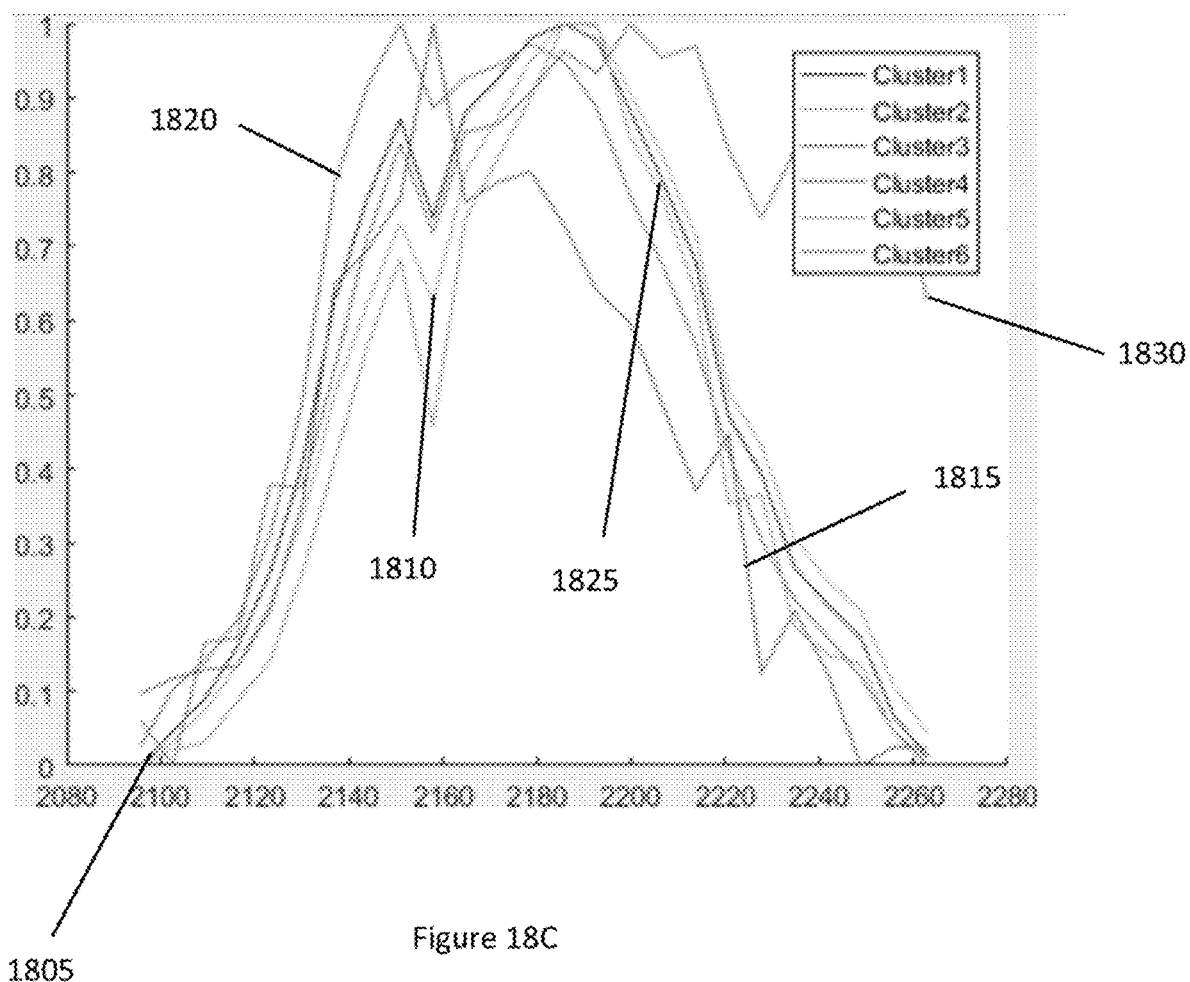
FIG. 18C is an exemplary graph illustrating exemplary Raman spectrum of each cluster of macromolecules according to an exemplary embodiment of the present disclosure.

FIG. 18C is an exemplary graph illustrating exemplary Raman spectrum of each cluster of macromolecules according to an exemplary embodiment of the present disclosure.

From cluster 1 (line 1805), cluster 2 (line 1810), cluster 3 (line 1815), cluster 4 (line 1820), cluster 5 (line 1825) and cluster 6 (line 1830), they represent 6 different clusters of newly synthesized macromolecules. They can be different types of proteins, subtypes of lipids (such as saturated lipids and unsaturated lipids), carbohydrates, etc. The Raman spectrum of each cluster of macromolecules can be slightly different due to their chemical bonds and environment, and this property can be utilized to develop an exemplary procedure to perform clustering for the CD signals. By clustering CD signal of metabolic activities using algorithm, it can provide multiplex imaging of temporal-spatial distribution of various newly synthesized biomolecules inside the biological tissue.

Exemplary Biorthogonal Infrared Imaging of Small Bio-Metabolites Using Vibrational Probes The exemplary system, method, and computer-accessible medium, according to an exemplary embodiment of the present disclosure, can utilize small vibrational tags, including azide, nitrile, fluorocarbon, and carbon-deuterium bonds, to perform functional IR imaging of dynamic small-molecule metabolism. The use of vibrational tags in vital biometabolites, such as, for example, amino acids, nucleic acids, choline, and glucose, can facilitate the monitoring of processes, such as protein turnover, energy metabolism, signal transportation, and genetic encoded labeling. Exemplary samples can be live or fixed samples, without destruction of the sample. Thus, the exemplary system, method, and computer-accessible medium, can facilitate imaging of small biometabolites and drugs with high selectivity and superior spatial resolution. The exemplary system, method and computer-accessible medium, can further utilize QCL-coupled IR spectroscopy and microscopy procedures, which can utilize a broadly tunable light source that can facilitate selection of discrete frequencies; eliminating the need to acquire the entire spectra, and thereby speeding up the imaging process.

IR spectroscopy can be used in both organic and inorganic chemistry to uniquely identify different chemicals, even for the examination of structure and dynamics of large biomolecules, especially proteins. (See, e.g., Reference 71). Further, IR spectroscopy can be used for the examination of biofluids, such as urine, serum, or whole blood. (See, e.g., References 72 and 73). IR imaging can also be employed in cancer detection and biomedical diagnosis. The integration of the noninvasive nature of FTIR spectroscopy and microscopy and its ability in obtaining spatially resolved chemical and structural information can facilitate its use in clinical histopathology. Applications can include, for example, screening of biopsy tissues to obtain tissue types and disease states based on the chemical information. (See, e.g., References 74 and 75). QCL coupled IR microscope can also be used to analyze tissue microarrays with single wavelength chemical imaging, which further speed up the process. (See. e.g., Reference 76).

Previous IR imaging procedures were used for label-free imaging. Despite the popularity of label-free imaging, such procedures suffer from some limitations including the lack of chemical specificity and influences of high cellular background in the fingerprint region. Also for probing certain dynamic processes, including uptake and trafficking, label-free imaging may not be suitable.

In contrast to traditional label-free imaging procedures, the exemplary system, method, and computer-accessible medium, according to an exemplary embodiment of the present disclosure, can utilize biorthogonal vibrational tags, which can be incorporated into the whole IR imaging field to determine various biological processes. Exemplary tiny vibrational tags, which may also be used in Raman imaging procedures, can be utilized for imaging of a broad range of small metabolites with dynamic information. Thus, the exemplary system, method, and computer-accessible medium, according to an exemplary embodiment of the present disclosure can be used in conjunction with Raman imaging. The use of tags for IR imaging can expand the scope for biorthogonal chemical imaging. The exemplary system, method and computer-accessible medium, can be faster as compared to Raman imaging, while also having the capability of imaging much larger fields of view, which can be beneficial for commercial use.

Exemplary FTIR procedures can utilize a broadband source (e.g., a single light source) which can enable the sweeping to the cell-silent region. In contrast, QCLs have exemplary bandwidths of about 200 cm$^{-1}$, and generally needs several QCLs to fill the entire spectral range. An exemplary Spero microscope can be viable to span the fingerprint region (e.g., about 900-1800 cm$^{-1}$). In order to facilitate the generation of IR probes in the cell-silent window, three tunable QCL modules in the coverage of about 1150 cm$^{-1}$ to 1800 cm$^{-1}$ and another tunable QCL channel which can be optimized for about 2125 cm$^{-1}$, can be utilized. This can facilitate the performance of both label-free imaging in the fingerprint region as well as specific chemical biorthogonal imaging of the vibrational tags.

Exemplary Cell-Silent Spectral Region

Figure 19:
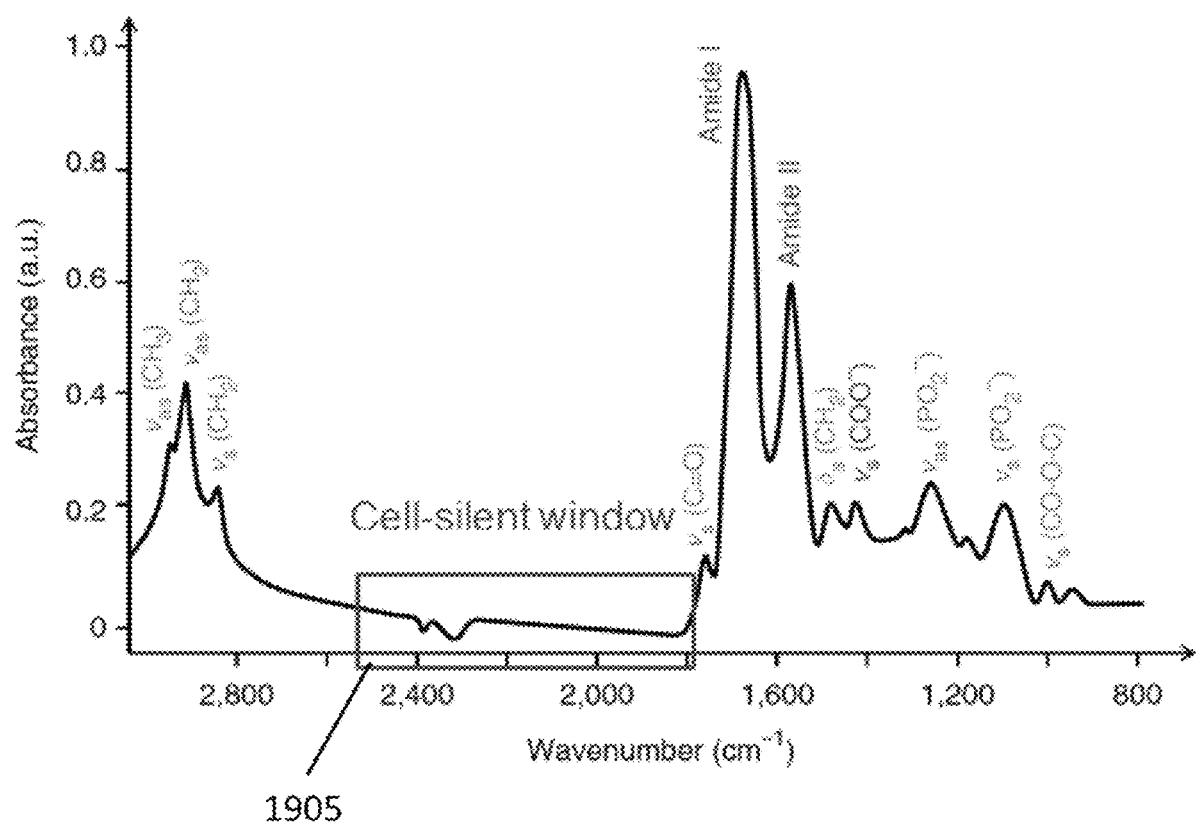
FIG. 19 is an exemplary graph illustrating absorbance vs. wavenumber according to an exemplary embodiment of the present disclosure.

FIG. 19 shows an exemplary graph illustrating absorbance vs. wavenumber according to an exemplary embodiment of the present disclosure. The "cell-silent spectral region" 1905, for example, 1800-2500 cm$^{-1}$, can be more suitable than other regions for label-free R imaging. This can be because, for example, no vibrational peaks likely exist in this region for intrinsic components in cell. Therefore, the crowded fingerprint region, which can bring high background noise to label-free IR imaging, can be avoided. Thus, the exemplary system, method, and computer-accessible medium according to an exemplary embodiment of the present disclosure, can label one or more particular molecules, and then image the molecules using IR imaging, for example, utilizing the cell silent window.

The exemplary tags used in conjunction with the exemplary system, method, and computer-accessible medium, can have specific frequency ranges within the silent window. For example, Azide has a frequency range of about 2100-2140 cm$^{-1}$ and an extinction coefficient of approximately 400 M$^{-1}$cm$^{-1}$. Nitrile has a frequency range of about 2200-2250 cm$^{-1}$ and an extinction coefficient of approximately 200 M$^{-1}$cm$^{-1}$. Carbon deuterium has a frequency range of about 2100-2400 cm$^{-1}$ and an extinction coefficient of approximately 5-10 M$^{-1}$cm$^{-1}$, Additionally, carbon 13 tags can be used. The exemplary compounds used to tag the molecules can be injected into a live subject or person. Alternatively, or in addition, the exemplary compounds can be ingested by the live subject.

The exemplary sample illumination time can depend on the signal level and the resolution utilized. For example, for abundant C-D vibrations, an about 2.0×2.0 mm$^2$ image area with about 4.25 µm pixel size may only need less than about 5 seconds for a particular band using Spero-QT. FT-IR imaging can sweep a full spectrum, which can take about 80 min to generate decent images.

The absorption of the infrared light can induce transitions between the vibrational energy levels. Spectral data and images can be acquired in transmission mode. Live tissue samples or paraffin fixed tissue samples can be mounted onto the IR transparent CaF$_2$ substrate. Background can be generated from a clean area of the sample. The absorption of the sample can result in the change of IR radiation, and the absorbance/background ratio of each pixel can be used to generate the image. For discrete-frequency imaging using Spero, the exemplary spectrum in a certain region can be acquired to find the peak position, and then a high-resolution image can be generated at the particular peak wavelength.

Biorthogonal chemical infrared imaging can provide a spatially resolved chemical identification of small metabolites in a quantitative manner. Compared to the label-free method, incorporation of small chemical tags can be beneficial for monitoring the uptake, synthesis, and degradation of certain biological molecules with high chemical specificity, like protein synthesis, glucose uptake and consumption, lipid metabolism, etc., especially in a complex sample with high heterogeneity. Drug metabolism can also be monitored and studied for certain drug molecules with intrinsic biorthogonal tags like C—F, nitrile bonds, or even with introduced small vibrational labels. Both spectral and spatial information can also facilitate a rational drug design. In contrast to prior IR imaging procedures, which can only produce images of a total lipid or protein, the exemplary system, method, and computer-accessible medium, according to an exemplary embodiment of the present disclosure, can produce images of newly synthesized lipid and proteins. Thus, the exemplary system, method, and computer-accessible medium according to an exemplary embodiment of the present disclosure can provide images of metabolic contrasts over different time periods.

The exemplary system, method, and computer-accessible medium according to an exemplary embodiment of the present disclosure can be used for biomedical imaging as well as pharmaceutical testing. The biomedical imaging for disease diagnosis can be called "spectral histopathology." For example, as a result of hypoxia, tumors generally have higher net uptake of glucose. Monitoring the glucose uptake with a labeled glucose analog (e.g., deuterated-glucose, fluorine-glucose) can facilitate differentiating between tumor and healthy tissues. This can be performed quickly, which can facilitate high throughput screening of biopsy tissues.

For pharmaceutical testing, the exemplary system, method and computer-accessible medium can be used for drug discovery and screening. Some intrinsic bonds of the drug and the small vibrational tag introduced to the drugs can facilitate the tracking of the drug molecules. For example, the exemplary system, method, and computer-accessible medium can be used as a screening platform, and can instruct the drug design with both chemical specificity and spatial information.

IR imaging can achieve a large filed-of-view ("FOV") (e.g., up to 2 mm depending on the size of FPA). This can also speed up the imaging of a particular area. For example, to image the mouse brain cortex, which can be a big unwrinkled surface with the size on the order of about 10 mm, a larger FOV can be beneficial to monitor the activity simultaneously in different regions. For live tissue cultures, an exemplary in vivo cultured tissue slice can be used, in which normal metabolites can be replaced by tagged metabolites in the culture medium. The live tissue can absorb up the tag molecules and incorporate them into the metabolism. For example, this can be performed using glucose or analogs of glucose.

Figure 20:
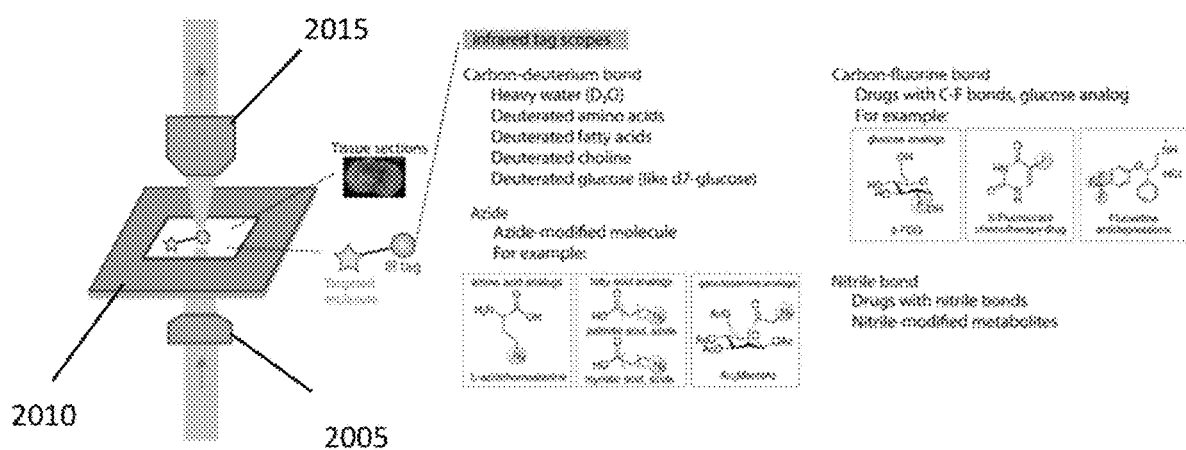
FIG. 20 is an exemplary diagram illustrating an exemplary microscope according to an exemplary embodiment of the present disclosure.

FIG. 20 shows an exemplary diagram illustrating an exemplary microscope according to an exemplary embodiment of the present disclosure. For example, as shown therein the IR tags can be attached to the targeted molecules, which can be placed on a bed 2010 and can form a specific chemical bond that vibrates in the cell silent region of the Raman Spectrum. These chemical bonds can include, for example, four different types: (i) a Carbon deuterium bond which can include heavy water, deuterated glucose, deuterated amino acids, deuterated fatty acids, deuterated choline, (ii) Azide modified molecules which can include amino acid analogs, fatty acids analogs, galactosamine analogs, (iii) Carbon-fluorine bonds which can include drugs with C—F bonds, glucose analog, and (iv) Nitride bonds which can include drugs with nitride bonds, nitride modified metabolites. Light can be generated user source 2005, which can then be received by receiver 2015.

Figure 21:
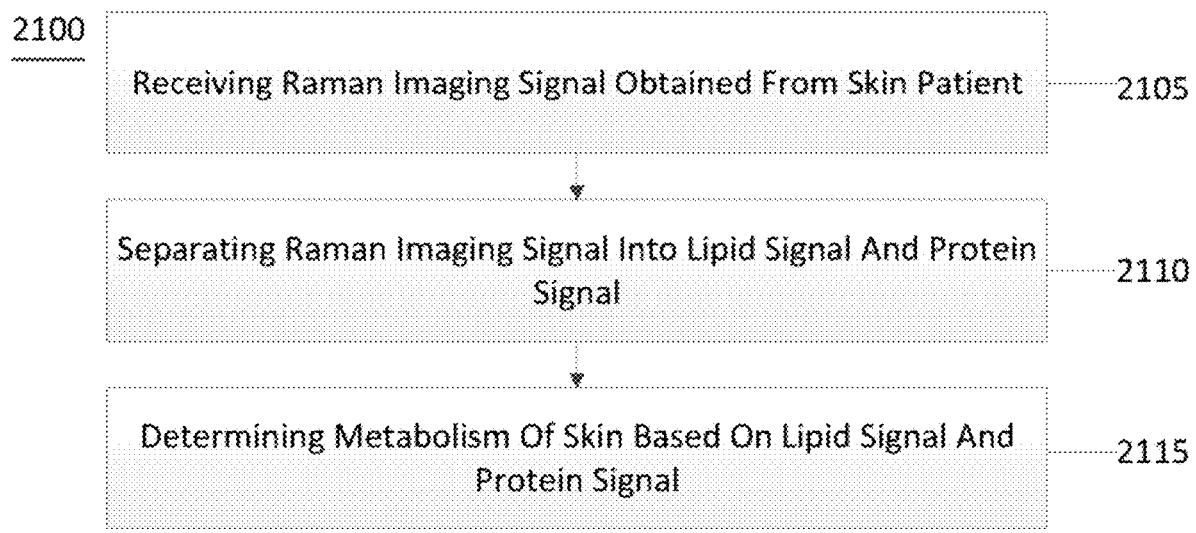
FIG. 21 is an exemplary flow diagram of an exemplary method for determining a metabolic activity of a skin of a patient according to an exemplary embodiment of the present disclosure.

FIG. 21 shows an exemplary flow diagram of an exemplary method 2100 for determining a metabolic activity of a skin of a patient according to an exemplary embodiment of the present disclosure. For example, at procedure 2105, a Raman imaging signal can be obtained from the skin of a patient. At procedure 2110, the Raman imaging signal can be separated into lipid signal and protein signal. At procedure 2115, the metabolic activity of the skin can be determined based on the lipid signal and the protein signal.

Figure 22:
FIG. 22 is an exemplary flow diagram of an exemplary method for determining information regarding a biological structure of at least one patient according to an exemplary embodiment of the present disclosure.

FIG. 22 shows an exemplary flow diagram of an exemplary method 2200 for determining information regarding a biological structure of at least one patient according to an exemplary embodiment of the present disclosure. For example, at procedure 2205, a drug can be administered to a patient. At procedure 2210, a vibrational probe can be administered to a patient. At procedure 2215, a biological structure of the patient can be imaged using a stimulated Raman scattering (SRS) imaging procedure. At procedure 2220, a SRS signal can be received from a biological structure of the patient. At procedure 2225, the SRS signal can be separated into a lipid signal and a protein signal. At procedure 2230, information can be determined based on the lipid signal and the protein signal.

Figure 23:
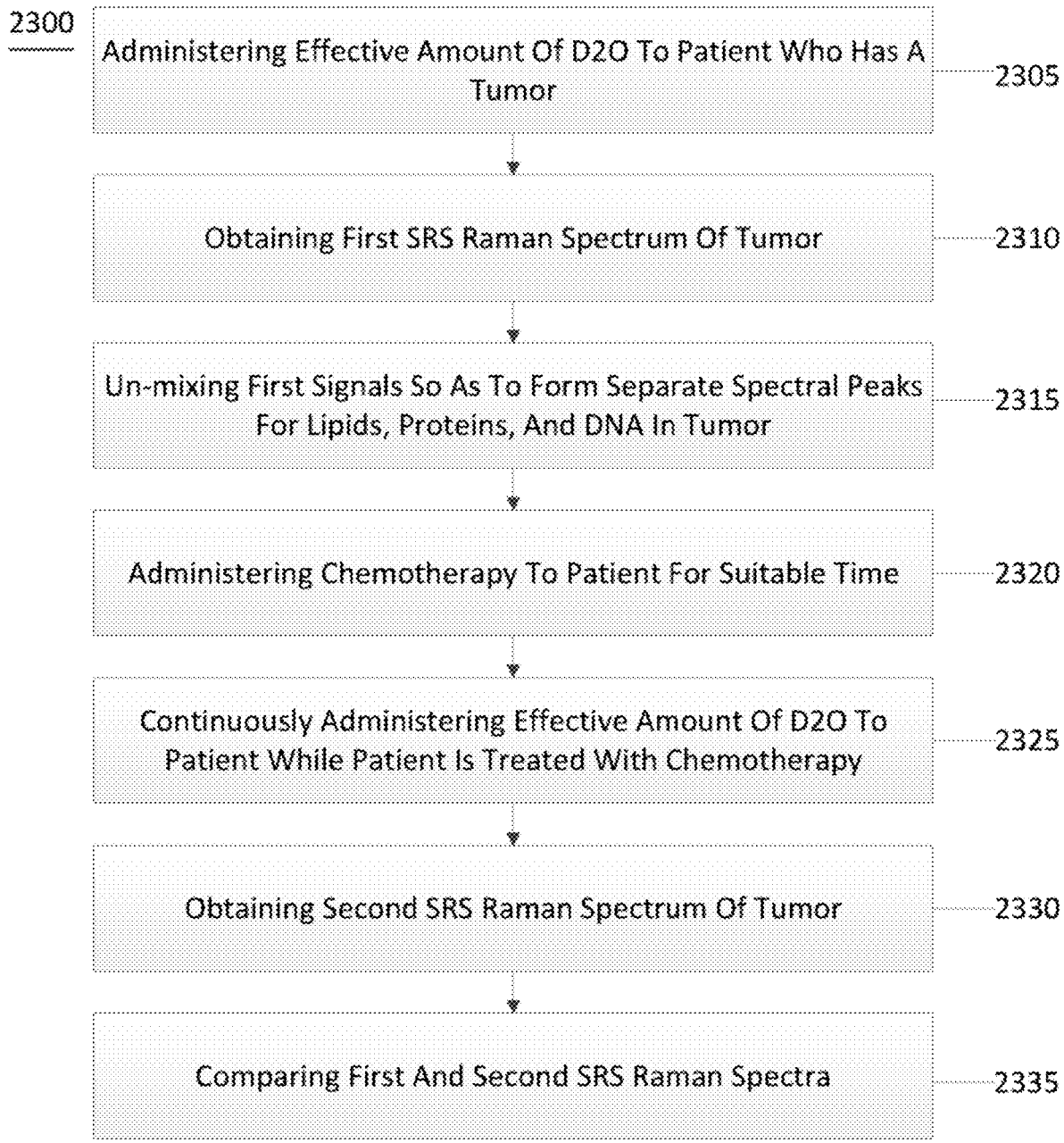
FIG. 23 is an exemplary flow diagram of an exemplary method for determining a metabolic activity of a skin of a patient according to an exemplary embodiment of the present disclosure.

FIG. 23 shows an exemplary flow diagram of an exemplary method 2300 for determining a metabolic activity of a skin of a patient according to an exemplary embodiment of the present disclosure. For example, at procedure 2305, an effective amount of $D_2O$ can be administered to a patient who has a tumor. At procedure 2310, first SRS Raman spectrum of the tumor can be obtained. At procedure 2315, the first signals can be unmixed so as to form separate spectral peaks for lipids, proteins, and DNA in the tumor. At procedure 2320, chemotherapy can be administered to the patient for a suitable time. At procedure 2325, effective amount of $D_2O$ can be continuously administered to the patient while the patient is treated with the chemotherapy. At procedure 2330, second SRS Raman spectrum of the tumor can be obtained. At procedure 2335, the first and second SRS Raman spectra can be compared.

Figure 24:
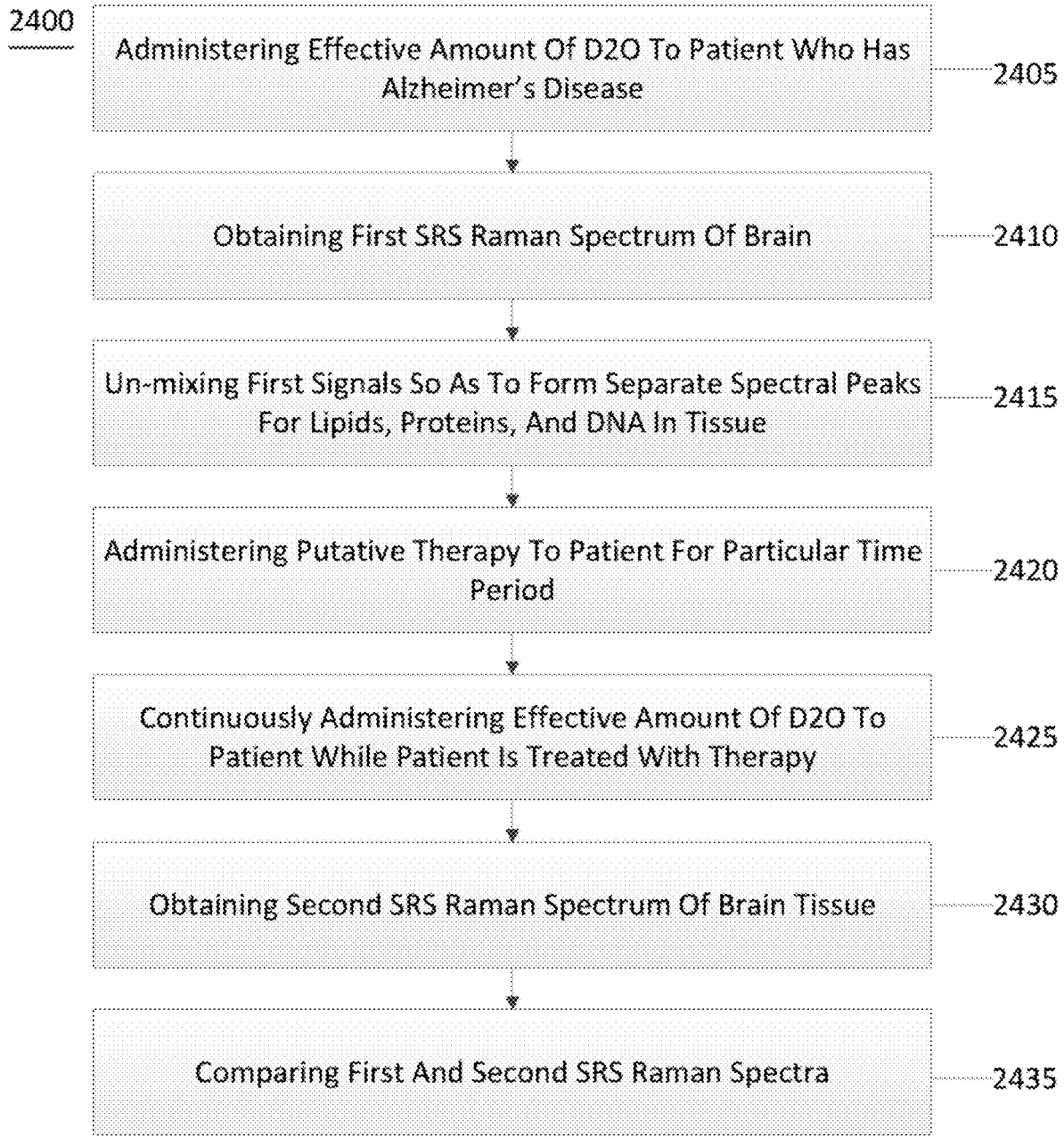
FIG. 24 is an exemplary flow diagram of an exemplary method for determining the efficacy of a putative therapy for Alzheimer's Disease according to an exemplary embodiment of the present disclosure.

FIG. 24 shows an exemplary flow diagram of an exemplary method 2400 for determining the efficacy of a putative therapy for Alzheimer's disease according to an exemplary embodiment of the present disclosure. For example, at procedure 2405, an effective amount of $D_2O$ can be administered to a patient who has Alzheimer's disease. At procedure 2410, first SRS Raman spectrum of the brain can be obtained. At procedure 2415, the first signals can be un-mixed so as to form separate spectral peaks for lipids, proteins, and DNA in the tissue. At procedure 2420, putative therapy can be administered to the patient for a particular time period. At procedure 2425, an effective amount of $D_2O$ can be continuously administered to the patient while the patient is treated with the therapy. At procedure 2430, second SRS Raman spectrum of the brain tissue can be obtained. At procedure 2435, the first and second SRS Raman spectra can be compared.

Figure 25:
FIG. 25 is an exemplary flow diagram of an exemplary method for determining the efficacy of a putative therapy for a metabolic disease according to an exemplary embodiment of the present disclosure.

FIG. 25 shows an exemplary flow diagram of an exemplary method 2500 for determining the efficacy of a putative therapy for a metabolic disease according to an exemplary embodiment of the present disclosure. For example, at procedure 2505, an effective amount of $D_2O$ can be administered to a patient who has a metabolic disease. At procedure 2510, first SRS Raman spectrum of a biological fluid comprising lipids can be obtained. At procedure 2515, the first signals can be un-mixed so as to form separate spectral peaks for lipids, proteins, and DNA in a biological sample. At procedure 2520, a putative therapy can be administered to the patient for a suitable time. At procedure 2525, an effective amount of $D_2O$ can be continuously administered to the patient while the patient is treated with the therapy. At procedure 2530, second SRS Raman spectrum of brain tissue can be obtained. At procedure 2535, the first and second SRS Raman spectra can be compared.

Figure 26:
FIG. 26 is an exemplary flow diagram of an exemplary method for determining the efficacy of an antimicrobial compound according to an exemplary embodiment of the present disclosure.

FIG. 26 shows an exemplary flow diagram of an exemplary method 2600 for determining the efficacy of an antimicrobial compound according to an exemplary embodiment of the present disclosure. For example, at procedure 2605, an effective amount of $D_2O$ can be administered to a patient who has a microbial infection. At procedure 2610, a sample of a biological fluid comprising a microbe responsible for a microbial infection can be obtained. At procedure 2615, second signals can be un-mixed so as to form separate spectral peaks for lipids, proteins, and DNA in a biological fluid. At procedure 2620, a putative antimicrobial therapy can be administered to the patient for a particular time. At procedure 2625, an effective amount of $D_2O$ can be continuously administered to the patient while the patient is treated with the therapy. At procedure 2630, a second sample of biological fluid can be obtained from the patient. At procedure 2635, second SRS Raman spectrum of the fluid can be obtained. At procedure 2640, the first and second SRS Raman spectra can be compared.

Figure 27:
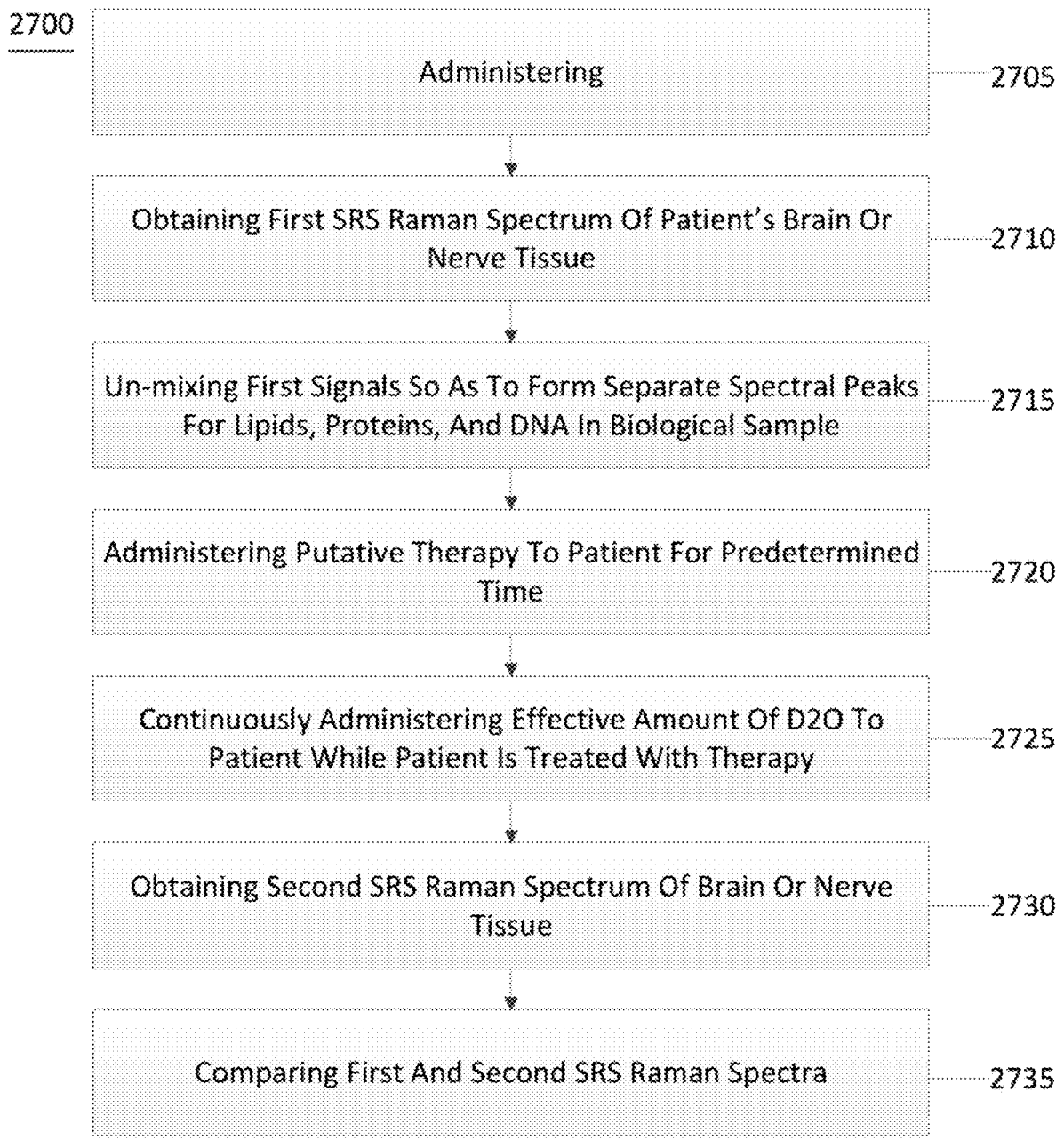
FIG. 27 is an exemplary flow diagram of an exemplary method for determining the efficacy of a putative therapy for multiple sclerosis according to an exemplary embodiment of the present disclosure.

FIG. 27 shows an exemplary flow diagram of an exemplary method 2700 for determining the efficacy of a putative therapy for multiple sclerosis according to an exemplary embodiment of the present disclosure. For example, at procedure 2705, an effective amount of $D_2O$ can be administered to a patient who has multiple sclerosis. At procedure 2710, first SRS Raman spectrum of the patient's brain or nerve tissue can be obtained. At procedure 2715, the first signals can be un-unmixed so as to form separate spectral peaks for lipids, proteins, and DNA in a biological sample. At procedure 2720, a putative therapy can be administered to the patient for a predetermined time. At procedure 2725, an effective amount of $D_2O$ can be continuously administered to the patient while the patient is treated with the therapy. At procedure 2730, second SRS Raman spectrum of brain or nerve tissue can be obtained. At procedure 2735, the first and second SRS Raman spectra can be compared.

Figure 28:
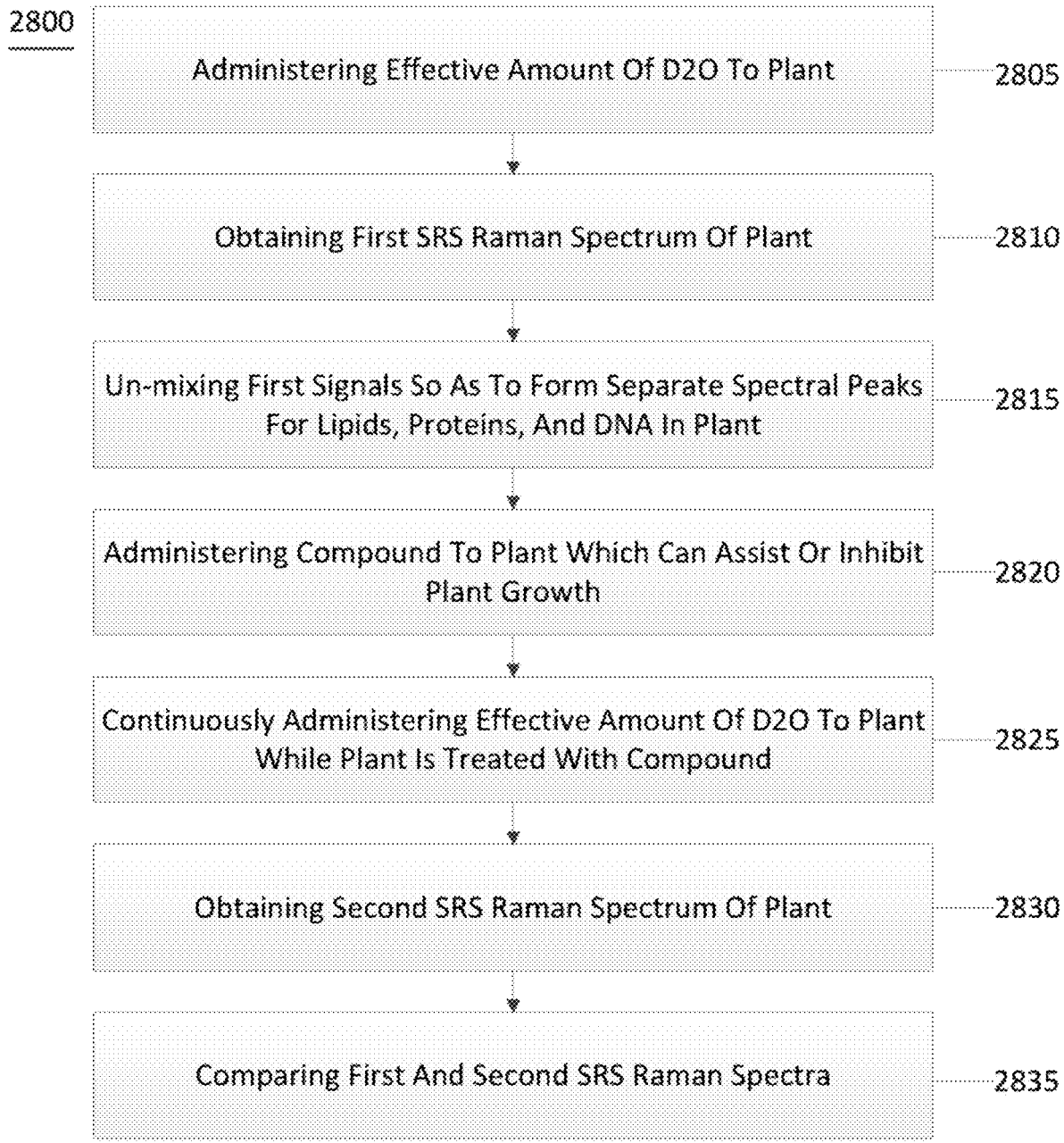
FIG. 28 is an exemplary flow diagram of an exemplary method 2300 for evaluating the effectiveness of a compound on a plant according to an exemplary embodiment of the present disclosure.

FIG. 28 shows an exemplary flow diagram of an exemplary method 2800 for evaluating the effectiveness of a compound on a plant according to an exemplary embodiment of the present disclosure. For example, at procedure 2805, an effective amount of $D_2O$ can be administered to the plant. At procedure 2810, first SRS Raman spectrum of the plant can be obtained. At procedure 2815, the first signals can be un-mixed so as to form separate spectral peaks for lipids, proteins, and DNA in the plant. At procedure 2820, a compound can be administered to the plant which can assist or inhibit plant growth. At procedure 2825, an effective amount of $D_2O$ can be continuously administered to the plant while the plant is treated with the compound. At procedure 2830, second SRS Raman spectrum of the plant can be obtained. At procedure 2835, the first and second SRS Raman spectra can be compared.

FIG. 29 shows an exemplary flow diagram of an exemplary method 2900 for monitoring plant growth or inhibition according to an exemplary embodiment of the present disclosure. For example, at procedure 2905, heavy water can be administered to the plants. At procedure 2910, sufficient time for the plant leaves to incorporate $D_2O$ into proteins and/or lipids in plant leaves can be facilitated. At procedure 2915, first SRS Raman spectrum of the plant leaves can be obtained in order to obtain baseline values for protein and/or lipid levels. At procedure 2920, a compound can be administered to the plant which may inhibit or promote plant growth. At procedure 2925, second SRS Raman spectrum of the plant leaves can be obtained in order to obtain subsequent values for protein and/or lipid levels.

Figure 30:
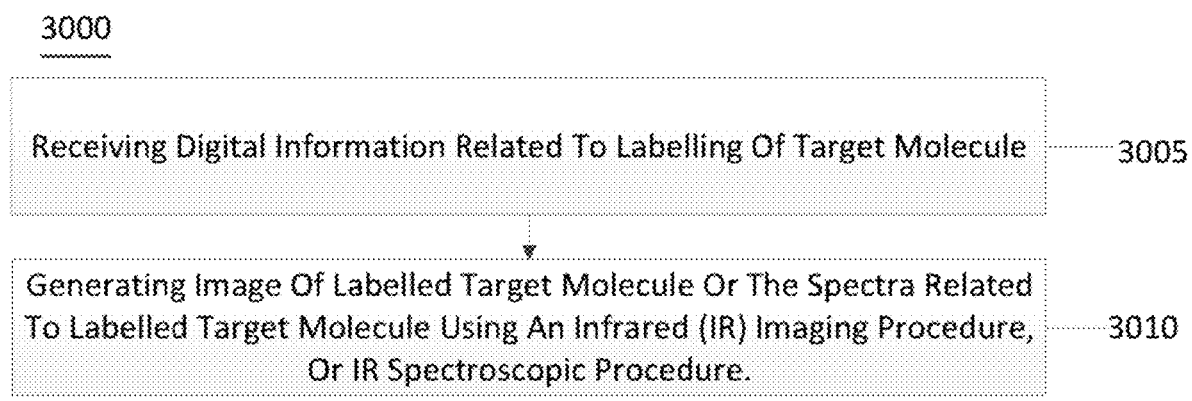
FIG. 30 is an exemplary flow diagram of an exemplary method for generating an image of a target molecule or a plurality of spectra related to the target molecule according to an exemplary embodiment of the present disclosure.

FIG. 30 shows an exemplary flow diagram of an exemplary method 3000 for generating an image of a target molecule or a plurality of spectra related to the target molecule according to an exemplary embodiment of the present disclosure. For example, at procedure 3005, digital information related to labelling of the target molecule can be received. At procedure 3010, the image of labelled target molecule or the spectra related to the labelled target molecule can be generated using an infrared (IR) imaging procedure or (ii) an IR spectroscopic procedure.

Figure 31:
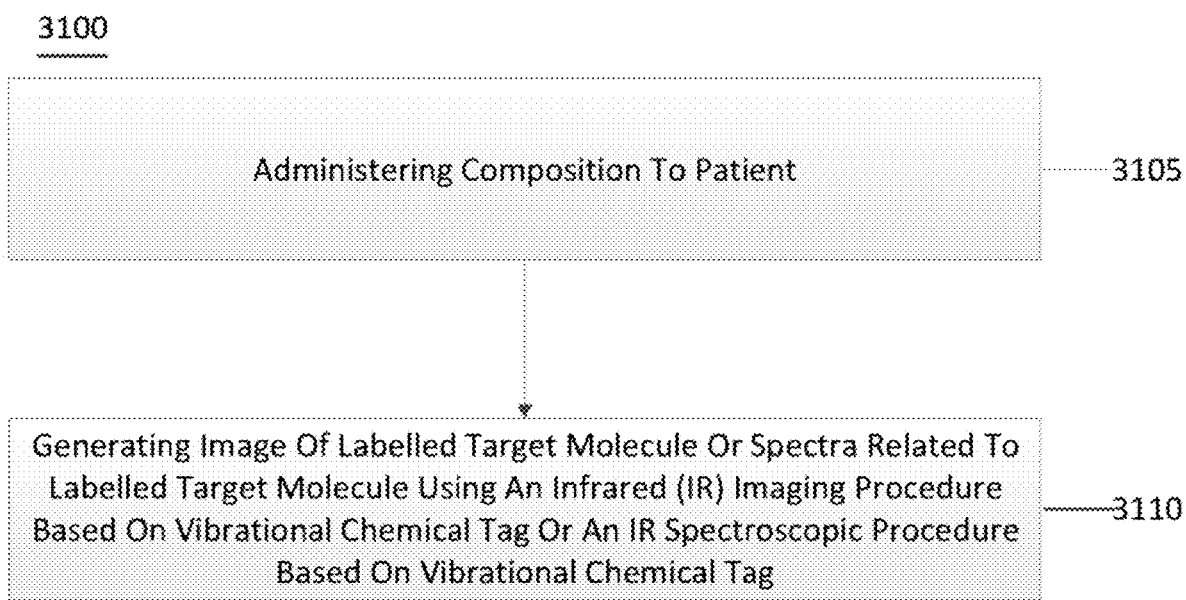
FIG. 31 is an exemplary flow diagram of an exemplary method for generating an image of a target molecule or a plurality of spectra related to the target molecule according to an exemplary embodiment of the present disclosure.

FIG. 31 shows an exemplary flow diagram of an exemplary method 3100 for generating an image of a target molecule or a plurality of spectra related to the target molecule according to an exemplary embodiment of the present disclosure. For example, at procedure 3105, a composition can be administered to a patient. At procedure 3110, an image of a labelled target molecule or spectra related to the labelled target molecule can be generated using an infrared (IR) imaging procedure based on the vibrational chemical tag or an IR spectroscopic procedure based on the vibrational chemical tag.

Figure 32:
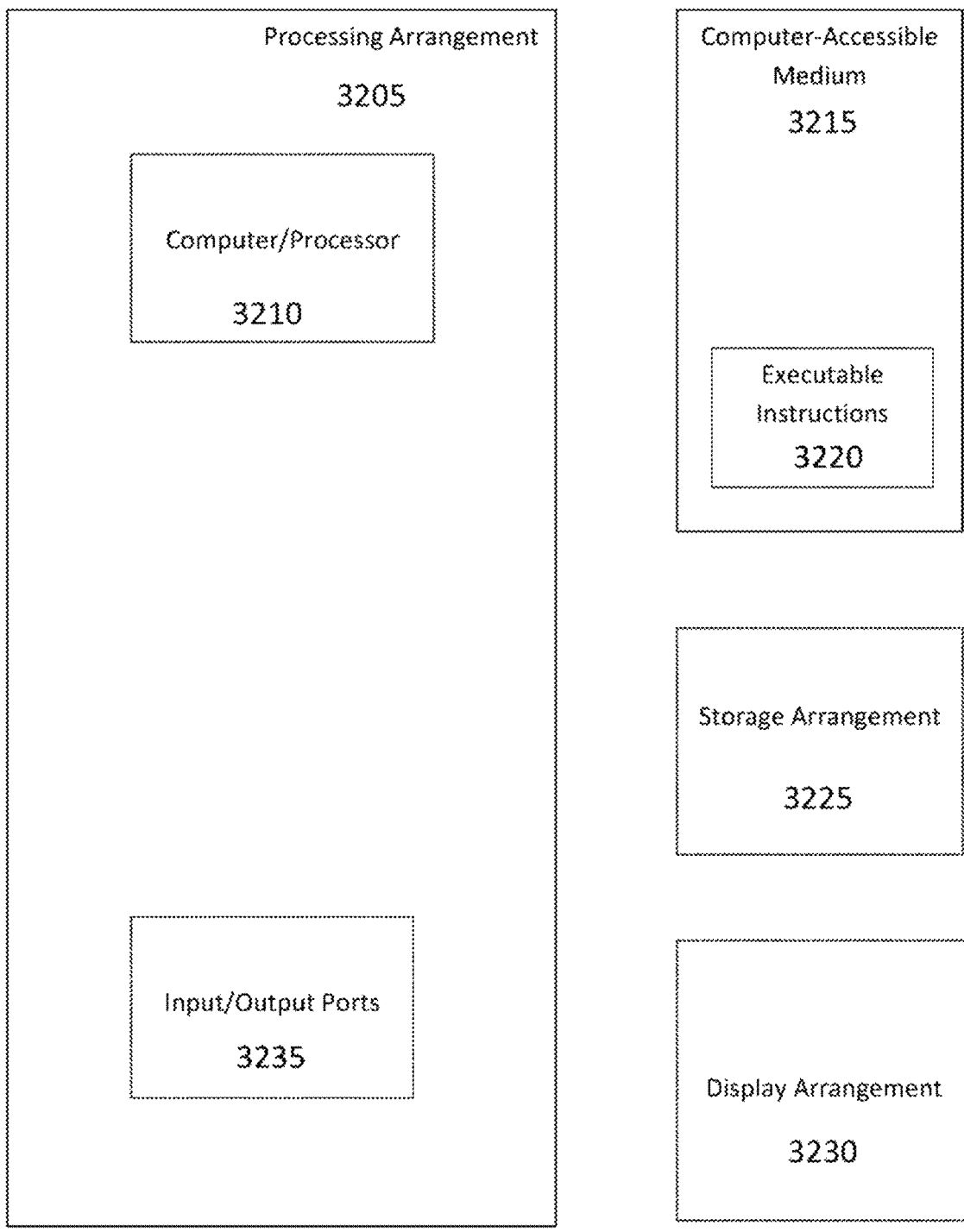
FIG. 32 is an illustration of an exemplary block diagram of an exemplary system in accordance with certain exemplary embodiments of the present disclosure.

FIG. 32 shows a block diagram of an exemplary embodiment of a system according to the present disclosure. For example, exemplary procedures in accordance with the present disclosure described herein can be performed by a processing arrangement and/or a computing arrangement (e.g., computer hardware arrangement or a hardware computing arrangement) 1905. Such processing/computing arrangement 1905 can be, for example entirely or a part of, or include, but not limited to, a computer/processor 1910 that can include, for example one or more microprocessors, and use instructions stored on a computer-accessible medium (e.g., RAM, ROM, hard drive, or other storage devices).

As shown in FIG. 32, for example, a computer-accessible medium 3215 (e.g., as described herein above, a storage device such as a hard disk, floppy disk, memory stick, CD-ROM, RAM. ROM, etc., or a collection thereof) can be provided (e.g., in communication with the processing arrangement 3205). The computer-accessible medium 3215 can contain executable instructions 3220 thereon. In addition or alternatively, a storage arrangement 3225 can be provided separately from the computer-accessible medium 3215, which can provide the instructions to the processing arrangement 3205 so as to configure the processing arrangement to execute certain exemplary procedures, processes, and methods, as described herein above, for example.

Further, the exemplary processing arrangement 3205 can be provided with or include an input/output ports 3235, which can include, for example a wired network, a wireless network, the internet, an intranet, a data collection probe, a sensor, etc. As shown in FIG. 32, the exemplary processing arrangement 3205 can be in communication with an exemplary display arrangement 3230, which, according to certain exemplary embodiments of the present disclosure, can be a touch-screen configured for inputting information to the processing arrangement in addition to outputting information from the processing arrangement, for example. Further, the exemplary display arrangement 3230 and/or a storage arrangement 3225 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following references are hereby incorporated by reference in their entireties:
1. Kim M M, Parolia A, Dunphy M P, Venneti S. Non-invasive metabolic imaging of brain tumours in the era of precision medicine. *Nat Rev Clin Oncol* 13, 725-739 (2016).
2. Musat N, Foster R, Vagner T, Adam B, Kuypers M M. Detecting metabolic activities in single cells, with emphasis on nanoSMS. *FEMS Microbiol Rev* 36.486-511 (2012).
3. Lechene C, et al. High-resolution quantitative imaging of mammalian and bacterial cells using stable isotope mass spectrometry. *J Biol* 5, 20 (2006).
4. Steinhauser M L. et al. Multi-isotope imaging mass spectrometry quantifies stem cell division and metabolism. *Nature* 481, 516-519 (2012).
5. Miyagi M, Kasumov T. Monitoring the synthesis ofbiomolecules using mass spectrometry. *Philos Trans A Math Phys Eng Sci* 374, (2016).

6. Previs S F, et al. New methodologies for studying lipid synthesis and turnover: looking backwards to enable moving forwards. *Biochim Biophys Acta* 1842, 402-413 (2014).
7. Foletta V C, et al. Analysis of Mammalian Cell Proliferation and Macromolecule Synthesis Using Deuterated Water and Gas Chromatography-Mass Spectrometry. *Metabolites* 6, (2016).
8. Kloehn J, Saunders E C, O'Callaghan S, Dagley M J, McConville M J. Characterization of metabolically quiescent *Leishmania* parasites in murine lesions using heavy water labeling. *PLoS Pathog* 11, e1004683 (2015).
9. Berry D, et al. Tracking heavy water ($D_2O$) incorporation for identifying and sorting active microbial cells. *Proc Natl Acad Sci USA* 112, E194-203 (2015).
10. Tao Y, et al. Metabolic-Activity-Based Assessment of Antimicrobial Effects by $D_2O$-Labeled Single-Cell Raman Microspectroscopy. *Anal Chem* 89, 4108-4115 (2017).
11. Freudiger C W, et al. Label-free biomedical imaging with high sensitivity by stimulated Raman scattering microscopy. *Science* 322, 1857-1861 (2008).
12. Min W, Freudiger C W, Lu S, Xie X S. Coherent nonlinear optical imaging: beyond fluorescence microscopy. *Annu Rev Phys Chem* 62, 507-530 (2011).
13. Cheng J X, Xie X S. Vibrational spectroscopic imaging of living systems: An emerging platform for biology and medicine. *Science* 350, aaa8870 (2015).
14. Wei L, Hu F, Chen Z, Shen Y, Zhang L, Min W. Live-Cell Bioorthogonal Chemical Imaging: Stimulated Raman Scattering Microscopy of Vibrational Probes. *Acc Chem Res* 49, 1494-1502 (2016).
15. Valencia M E, Aleman-Mateo H, Salazar G, Hernandez Triana M. Body composition by hydrometry (deuterium oxide dilution) and bioelectrical impedance in subjects aged >60 y from rural regions of Cuba, Chile and Mexico. *Int J Obes Relat Metab Disord* 27, 848-855 (2003).
16. Schoeller D A. Recent advances from application of doubly labeled water to measurement of human energy expenditure. *J Nutr* 129, 1765-1768 (1999).
17. Jones P J, Leatherdale S T. Stable isotopes in clinical research: safety reaffirmed. *Clin Sci (Lond)* 80, 277-280 (1991).
18. Guillermier C, et al. Imaging mass spectrometry demonstrates age-related decline in human adipose plasticity. *JCI Insight* 2, e90349 (2017).
19. Neese R A, et a$_L$. Measurement in vivo of proliferation rates of slow turnover cells by 2H2O labeling of the deoxyribose moiety of DNA. *Proc Nal Acad Sci* USA 99, 15345-15350 (2002).
20. Hodel A. Gebbers J O, Cottier H, Laissue J A. Effects of prolonged moderate body deuteration on proliferative activity in major cell renewal systems in mice. *Life Sci* 30, 1987-1996 (1982).
21. Peng S K, Ho K J, Taylor C B. Biologic effects of prolonged exposure to deuterium oxide. A behavioral, metabolic, and morphologic study. *Arch Pathol* 94, 81-89 (1972).
22. Lu F K, et al, Multicolor stimulated Raman scattering (SRS) microscopy. *Mol Phys* 110, 1927-1932 (2012).
23. Yu Z L. et al. Label-free chemical imaging in vitro: three-dimensional non-invasive microscopic observation of amphioxus notochord through stimulated Raman scattering (SRS). *Chemical Science* 3, 2646-2654 (2012).
24. Lu F K, et al. Label-free DNA imaging in vivo with stimulated Raman scattering microscopy. *Proc Nal Acad Sci USA* 112, 11624-11629 (2015).
25. Diem M, Polavarapu P L, Oboodi M, Nafie L A. Vibrational circular dichroism in amino acids and peptides. 4. Vibrational analysis, assignments, and solution-phase Raman spectra of deuterated isotopomers of alanine. *J Am Chem Soc* 104, 3329-3336 (1985).
26. Busch R, et al. Measurement of protein turnover rates by heavy water labeling of nonessential amino acids. *Biochim Biophys Acta* 1760, 730-744 (2006).
27. Lewis C A, et al. Tracing compartmentalized NADPH metabolism in the cytosol and mitochondria of mammalian cells. *Mol Cell* 55, 253-263 (2014).
28. Hu F, Lamprecht M R, Wei L, Morrison B, Min W. Bioorthogonal chemical imaging of metabolic activities in live mammalian hippocampal tissues with stimulated Raman scattering. *Sci Rep* 6, 39660 (2016).
29. Fu D, et al. In vivo metabolic fingerprinting of neutral lipids with hyperspectral stimulated Raman scattering microscopy. *J Am Chem Soc* 136, 8820-8828 (2014).
30. Shen Y, et al. Metabolic activity induces membrane phase separation in endoplasmic reticulum. *Proc Natl Acad Sci USA* 114, 13394-13399 (2017).
31. Yu Y, Mutlu A S, Liu H, Wang M C. High-throughput screens using photo-highlighting discover BMP signaling in mitochondrial lipid oxidation. *Nat Commun* 8, 865 (2017).
32. Perez C L, Van Gilst M R. A 13C isotope labeling strategy reveals the influence of insulin signaling on lipogenesis in *C. elegans*. *Cell Metab* 8, 266-274 (2008).
33. Cassada R C, Russell R L. The dauerlarva, a post-embryonic developmental variant of the nematode *Caenorhabditis elegans*. *Dev Biol* 46, 326-342 (1975).
34. Wang J, Kim S K, Global analysis of dauer gene expression in *Caenorhabditis elegans*. *Development* 130, 1621-1634 (2003).
35. Daemen S, vanZandvoort M A, Parekh S H, Hesselink M K. Microscopy tools for the investigation of intracellular lipid storage and dynamics. *Mol Metab* 5, 153-163 (2016).
36. Jung Y, Tam J. Jalian H R, Anderson R R, Evans C L. Longitudinal, 3D in vivo imaging of sebaceous glands by coherent anti-stokes Raman scattering microscopy: normal function and response to cryotherapy. *J Invest Dermatol* 135, 39-44 (2015).
37. Bercury K K, Macklin W B. Dynamics and mechanisms of CNS myelination. *Dev Cell* 32, 447-458 (2015).
38. Agmon A, Yang L T, O'Dowd D K, Jones E G. Organized growth of thalamocortical axons from the deep tier of terminations into layer IV of developing mouse barrel cortex. *J Neurosci* 13, 5365-5382 (1993).
39. Saely C H, Geiger K, Drexel H. Brown versus white adipose tissue: a mini-review. *Gerontology* 58, 15-23 (2012).
40. St-Onge M P, Gallagher D. Body composition changes with aging: the cause or the result of alterations in metabolic rate and macronutrient oxidation? *Nutrition* 26, 152-155 (2010).
41. Wei L. et al. Imaging complex protein metabolism in live organisms by stimulated Raman scattering microscopy with isotope labeling. *ACS Chem Biol* 10, 901-908 (2015).
42. Piez K A, Eagle H. The free amino acid pool of cultured human cells. *J Biol Chem* 231, 533-545 (1958).
43. Branicky R, Desjardins D, Liu J L, Hekimi S. Lipid transport and signaling in *Caenorhabditis elegans*. *Dev Dyn* 239, 1365-1377 (2010).

44. Herndon L A, et al. Stochastic and genetic factors influence tissue-specific decline in ageing C. elegans. Nature 419, 808-814 (2002).
45. Epstein J, Himmelhoch S. Gershon D. Studies on ageing in nematodes Ill. Electronmicroscopical studies on age-associated cellular damage. Mech Ageing Dev 1, 245-255 (1972).
46. Hagedorn M, Kleinhans F W, Artemov D, Pilatus U. Characterization of a major permeability barrier in the zebrafish embryo. Biol Reprod 59, 1240-1250 (1998).
47. Choi J, Dong L, Ahn J, Dao D, Hammerschmidt M, Chen I N. FoxHI negatively modulates flk1 gene expression and vascular formation in zebrafish. Dev Biol 304, 735-744 (2007).
48. Bertrand J Y, Traver D. Hematopoietic cell development in the zebrafish embryo. Curr Opin Hematol 16, 243-248 (2009).
49. Jin S W, Beis D, Mitchell T, Chen J N, Stainier D Y. Cellular and molecular analyses of vascular tube and lumen formation in zebrafish. Development 132, 5199-5209 (2005).
50. Ji M. et al. Rapid, label-free detection of brain tumors with stimulated Raman scattering microscopy. Sci Transl Med 5, 201ra119 (2013).
51. Sengupta D, Pratx G. Imaging metabolic heterogeneity in cancer. Mol Cancer 15, 4 (2016).
52. Li J, Cheng J X. Direct visualization of de novo lipogenesis in single living cells. Sci Rep 4, 6807 (2014).
53. Li J, et al. Lipid Desaturation Is a Metabolic Marker and Therapeutic Target of Ovarian Cancer Stem Cells. Cell Stem Cell 20, 303-314 e305 (2017).
54. Belanger M, Allaman I, Magistretti P J. Brain energy metabolism: focus on astrocyte-neuron metabolic cooperation. Cell Metab 14, 724-738 (2011).
55. Steinhauser M L, Guillermier C, Wang M, Lechene C P. Quantifying cell division with deuterated water and multi-isotope imaging mass spectrometry (MIMS). Surf Interface Anal 46, 161-164 (2014).
56. Louie K B, et al. Mass spectrometry imaging for in situ kinetic histochemistry. Sci Rep 3, 1656(2013).
57. Gemperline E, Chen B, Li L. Challenges and recent advances in mass spectrometric imaging of neurotransmitters. Bioanalysis 6, 525-540 (2014).
58. Saar B G, Johnston R S, Freudiger C W, Xie X S, Seibel F. J. Coherent Raman scanning fiber endoscopy. Opt Let 36, 2396-2398 (2011).
59. Chen X, et al. Volumetric chemical imaging by stimulated Raman projection microscopy and tomography. Nat Commun 8, 15117 (2017).
60. Saar B G, Freudiger C W, Reichman J, Stanley C M, Holtom G R, Xie X S. Video-rate molecular imaging in vivw with stimulated Raman scattering. Science 330, 1368-1370 (2010).
61. Brenner S. The genetics of Caenorhabditis elegans. Genetics 77, 71-94 (1974).
62. Westerfield M. The zebrafish book. A guide for the laboratory use of zebrafish (Danio rerio). 4th ed. Univ. of Oregon Press (2000).
63. Rodriguez-Contreras A, Shi L, Fu B M. A method to make a craniotomy on the ventral skull of neonate rodents. J Vis Exp, (2014).
64. Eguchi K. et al. Saturated fatty acid and TLR signaling link beta cell dysfunction and islet inflammation. Cell Metab 15, 518-533 (2012).
65. Ujike T, Tominaga Y. Raman spectral analysis of liquid ammonia and aqueous solution of ammonia. J Raman Spectrose 33, 485-493 (2002).
66. Hubbard E J, Greenstein D. Introduction to the germ line. WormBook, 1-4 (2005).
67. I. W. Levin, R. Bhargava, FOURIER TRANSFORM INFRARED VIBRATIONAL SPECTROSCOPIC IMAGING: Integrating Microscopy and Molecular Recognition. Annual Review of Physical Chemistry 56, 429-474 (2005).
68. C. J. Hirschmugl, K. M. Gough, Fourier Transform Infrared Spectrochemical Imaging: Review of Design and Applications with a Focal Plane Array and Multiple Beam Synchrotron Radiation Source. Applied Spectroscopy 66, 475-491 (2012).
69. M. J. Nasse et al., High-resolution Fourier-transform infrared chemical imaging with multiple synchrotron beams. Nat Meth 8, 413416 (2011).
70. J. Faist et al., Quantum Cascade Laser. Science 264, 553-556 (1994).
71. H. Kim, M. Cho, Infrared Probes for Studying the Structure and Dynamics of Biomolecules. Chemical Reviews 113, 5817-5847 (2013).
72. K. Gajjar et al., Fourier-transform infrared spectroscopy coupled with a classification machine for the analysis of blood plasma or serum: a novel diagnostic approach for ovarian cancer. Analyst 138, 3917-3926 (2013).
73. J. Ollesch et al., FTIR spectroscopy of biofluids revisited: an automated approach to spectral biomarker identification. Analyst 138, 4092-4102 (2013).
74. D. C. Fernandez, R. Bhargava, S. M. Hewitt, I. W. Levin, Infrared spectroscopic imaging for histopathologic recognition. Nat Biotech 23, 469-474 (2005).
75. E. Gazi et al., Applications of Fourier transform infrared microspectroscopy in studies of benign prostate and prostate cancer. A pilot study. The Journal of Pathology 201, 99-108 (2003).
76. P. Bassan, M. J. Weida, J. Rowlette, P. Gardner, Large scale infrared imaging of tissue micro arrays (TMAs) using a tunable Quantum Cascade Laser (QCL) based microscope. Analyst 139, 3856-3859 (2014).
77. Matthaus C, Bird B, Miljkovic M, Chernenko T, Romeo M, Diem M. Infrared and Raman microscopy in cell biology. Methods Cell Biol. 2008: 89: pp. 275-308.
78. Hu F, Lamprecht M R. Wei L, Morrison B, Min W. Bioorthogonal chemical imaging of metabolic activities in live mammalian hippocampal tissues with stimulated Raman scattering. Sci Rep. 2016 December; 6: pp. 39660.

What is claimed is:

1. A non-transitory computer-accessible medium having stored thereon computer-executable instructions for determining a metabolic activity of a skin or biological sample of at least one patient who has been administered or consumed $D_2O$, wherein, when a computing arrangement executes the instructions, the computing arrangement is configured to perform procedures comprising:

applying monochromatic light via two-laser excitation comprising a pump and a Stokes laser to the skin or biological sample of the at least one patient, said skin or biological sample comprising administered or consumed $D_2O$, so as to effect stimulated Raman scattering;

receiving a Raman imaging signal comprising at least about 2135 $cm^{-1}$, about 2185 $cm^{-1}$, and, optionally, about 2210 $cm^{-1}$, obtained from the skin or biological sample of the at least one patient;

separating the Raman imaging signal into at least a lipid signal and a protein signal;

normalizing said a lipid signal and a protein signal to a pure lipid and pure protein signal, respectively, and determining the metabolic activity of the skin or biological sample based on the normalized lipid signal and the normalized protein signal.

2. The computer-accessible medium of claim 1, wherein the computing arrangement is further configured to generate at least one volumetric image of at least one portion of the skin or biological sample using at least one quantum cascaded laser based on the metabolic activity.

3. A system for determining a metabolic activity of a skin or biological sample of at least one patient, comprising: a hardware computing arrangement configured to:

apply monochromatic light via two-laser excitation comprising a pump and a Stokes laser to the skin or biological sample of the at least one patient, said skin or biological sample comprising administered or consumed $D_2O$, so as to effect stimulated Raman scattering;

receive a Raman imaging signal comprising at least about 2135 $cm^{-1}$, about 2185 $cm^{-1}$, and, optionally, about 2210 $cm^{-1}$, obtained from the skin or biological sample of the at least one patient;

separate the Raman imaging signal into at least a lipid signal and a protein signal;

normalize said a lipid signal and a protein signal to a pure lipid and pure protein signal, respectively, and determine the metabolic activity of the skin or biological sample based on the normalized lipid signal and the normalized protein signal.

4. The system of claim 3, wherein the hardware computing arrangement is further configured to generate at least one volumetric image of at least one portion of the skin or biological sample using at least one quantum cascaded laser based on the metabolic activity.

5. A method for determining information regarding a biological structure of at least one patient, comprising:

administering or having administered $D_2O$ or a $D_2O$-containing composition to the at least one patient which affects the biological structure of the patient;

apply monochromatic light via two-laser excitation comprising a pump and a Stokes laser to the skin or biological sample of the at least one patient, said skin or biological sample comprising administered $D_2O$, so as to effect stimulated Raman scattering (SRS);

receiving a SRS signal from the biological structure of the at least patient said signal comprising at least about 2135 $cm^{-1}$, about 2185 $cm^{-1}$, and, optionally, about 2210 $cm^{-1}$;

separating the SRS signal into a lipid signal and a protein signal; and determining the information based on the lipid signal and the protein signal.

6. The method of claim 5, wherein the imaging of the biological structure is performed using a handheld SRS device.

7. The method of claim 5, wherein the biological structure is at least one of (i) skin of the at least one patient, (ii) skin cells of the at least one patient, or (iii) a bodily fluid of the at least one patient.

8. The method of claim 5, wherein the biological structure includes at least one of (i) blood or (ii) plasma.

9. The method of claim 5, further comprising administering at least one drug to the at least one patient, wherein the information includes an efficacy of the at least one drug on the biological structure.

10. The method of claim 5, wherein the determining of the information comprises generating at least one volumetric image of at least one portion of the biological structure using at least one quantum cascaded laser.

* * * * *